US012790389B2

(12) United States Patent
Kim et al.

(10) Patent No.: US 12,790,389 B2
(45) Date of Patent: Nov. 10, 2026

(54) BINDING MOLECULE AND USE THEREOF

(71) Applicant: Good T Cells, Inc., Seoul (KR)

(72) Inventors: Jung Ho Kim, Seoul (KR); Beom Seok Kim, Seoul (KR)

(73) Assignee: GOOD T CELLS, INC., Seoul (KR)

( * ) Notice: Subject to any disclaimer, the term of this patent is extended or adjusted under 35 U.S.C. 154(b) by 549 days.

(21) Appl. No.: 18/263,210

(22) PCT Filed: Jan. 27, 2022

(86) PCT No.: PCT/KR2022/001498

§ 371 (c)(1),
(2) Date: Jul. 27, 2023

(87) PCT Pub. No.: WO2022/164231

PCT Pub. Date: Aug. 4, 2022

(65) Prior Publication Data

US 2024/0301050 A1 Sep. 12, 2024

(30) Foreign Application Priority Data

Jan. 27, 2021 (KR) ........................ 10-2021-0011845

(51) Int. Cl.

| | |
|---|---|
| ***C07K 16/28*** | (2006.01) |
| ***A61K 39/00*** | (2006.01) |
| ***A61K 47/68*** | (2017.01) |
| ***A61P 25/28*** | (2006.01) |
| ***C07K 14/705*** | (2006.01) |
| ***G01N 33/68*** | (2006.01) |

(52) U.S. Cl.

CPC .............. *C07K 16/28* (2013.01); *A61K 39/00* (2013.01); *A61K 47/6849* (2017.08); *A61P 25/28* (2018.01); *C07K 14/7051* (2013.01); *G01N 33/6896* (2013.01); *A61K 2039/505* (2013.01); *C07K 2317/24* (2013.01); *C07K 2319/00* (2013.01); *G01N 2800/2821* (2013.01)

(58) Field of Classification Search

None

See application file for complete search history.

(56) References Cited

U.S. PATENT DOCUMENTS

| | | | |
|---|---|---|---|
| 2020/0048343 | A1 | 2/2020 | Kim |
| 2020/0399354 | A1 | 12/2020 | Sentman et al. |
| 2021/0347849 | A1 | 11/2021 | Kim |
| 2022/0213186 | A1 | 7/2022 | Kim |
| 2022/0275081 | A1 | 9/2022 | Kim |

OTHER PUBLICATIONS

GenBank, "immunoglobulin lambda light chain variable region, partial [*Homo sapiens*]," Accession No. CAG17619.1, Accession Date Jul. 26, 2016.

International Search Report (translation) and Written Opinion (machine translation) in International Patent Application No. PCT/KR2022/001498, dated May 9, 2022.

Vogel et al., A Highly Conserved Interspecies VH in the Human Genome, J. Mol. Biol. (2004) 341: 477-489.

*Primary Examiner* — Nelson B Moseley, II
*Assistant Examiner* — James Ryland Melchior
(74) *Attorney, Agent, or Firm* — McDonnell Boehnen Hulbert & Berghoff LLP

(57) ABSTRACT

The present invention relates to a novel binding molecule with excellent preventive, ameliorative or therapeutic effects on a brain and nervous system disease and uses thereof. The binding molecule provided in the present invention can effectively prevent or treat brain and nervous system diseases, particularly neurodegenerative diseases or neuroinflammatory diseases.

20 Claims, 14 Drawing Sheets

Specification includes a Sequence Listing.

| Gene | Fold Change | Reference |
|---|---|---|
| GPR83 | 29.5 | J. Immunol. 2006 |
| Nrp1 | 23.7 | Eur. J. Immunol. 2004 |
| Lag3 | 3.1 | Immunity. 2003 |
| Ikzf4 | 4.2 | Science. 2009 |

| | Mice strain | Mice No. | Test article | Dosing regimen | | | Note |
|---|---|---|---|---|---|---|---|
| | | | | Dose | Frequency | Route | |
| G1 | WT | 12 | Vehicle | - | - | | WT Ctrl |
| G2 | 5xFAD | 10 | Vehicle | - | - | | Tg Ctrl |
| G3 | | 8 | Glatiramer acetate | 100 ug | BIW+QW x 3 wks | SC | Immune modulator (random polymer composed of four AA of MBP) |
| G4 | | 10 | GTC110-04 | 10 mpk | BIW x 4 wks | IV | anti-Lrig1 antibody |
| G5 | | 10 | GTC310-01 | 10 mpk | BIW x 3 wks | IV | anti-Lrig1 antibody |

Biweekly for 2 months

| | Group | Number |
|---|---|---|
| WT | Vehicle | 7 |
| 5xFAD(Female) | Vehicle | 6 |
| | GTC310-01 | 6 |
| 6xTg(Female) | Vehicle | 7 |
| | GTC310-01 | 8 |

BINDING MOLECULE AND USE THEREOF

CROSS-REFERENCE TO RELATED APPLICATIONS

This application is a U.S. National Stage entry of International Patent Application no. PCT/KR2022/001498, filed Jan. 27, 2022, which claims the benefit of priority of Korean Patent Application no. 10-2021-0011845, filed Jan. 27, 2021.

TECHNICAL FIELD

The present invention relates to a novel binding molecule with excellent preventive, ameliorative or therapeutic effects on a brain and nervous system disease and uses thereof.

Sequence Listing Statement

The instant application contains an electronic Sequence Listing that has been submitted electronically and is hereby incorporated by reference in its entirety. The Sequence Listing was created on Apr. 27, 2026, is named "23-1079-WO-US_ST25" and is 81,797 bytes in size.

BACKGROUND ART

In degenerative brain and nervous system diseases such as stroke, dementia, and Alzheimer's disease, deterioration in memory, attention, cognitive ability, emotion regulation, and the like is observed, which results from death of neuronal cells and atrophy of nerve branches. Nerve branch elongation in neuronal cells leads to increased neuroplasticity, and thus plays an important role in memory and learning functions of neural circuitry. Therefore, it is predicted that active ingredients, which promote nerve branch elongation and nerve regeneration in neuronal cells, have the potential to be developed as new therapeutic agents for degenerative brain and nervous system diseases.

As the aging population rapidly increases, the incidence of degenerative brain and nervous system diseases is also on the rise. Despite innovative advances in medicine, prophylactic and therapeutic methods for degenerative brain and nervous system diseases are not yet clearly established, and no drugs have been found which have a decisive effect. Currently, therapeutic agents and treatment methods for degenerative brain and nervous system diseases are being developed; however, they often exhibit side effects and toxicity due to long-term use, and only have an effect of alleviating symptoms rather than treating the disease. Therefore, there is an urgent need to develop a material capable of achieving treatment while having decreased side effects and toxicity.

Technical Problem

An object of the present invention is to provide a binding molecule that has excellent binding ability to the Lrig-1 protein present on the surface of regulatory T cells (Treg) and is excellent in preventing, ameliorating, or treating a brain and nervous system disease.

Another object of the present invention is to provide a nucleic acid molecule encoding said binding molecule according to the present invention.

Another object of the present invention is to provide an expression vector into which the nucleic acid molecule according to the present invention is inserted.

Another object of the present invention is to provide a host cell line transfected with the expression vector according to the present invention.

Another object of the present invention is to provide an antibody-drug conjugate according to the present invention.

Another object of the present invention is to provide a composition for preventing, ameliorating or treating a brain and nervous system disease comprising the binding molecule according to the present invention.

Another object of the present invention is to provide a pharmaceutical composition for preventing or treating a brain and nervous system disease comprising the antibody-drug conjugate according to the present invention as an active ingredient.

Another object of the present invention is to provide a pharmaceutical composition for preventing or treating a brain and nervous system disease comprising the chimeric antigen receptor (CAR) according to the present invention as an active ingredient.

Another object of the present invention is to provide a diagnostic composition and kit for diagnosing a brain and nervous system disease comprising the binding molecule according to the present invention, and a method for providing information for diagnosing a brain and nervous system disease.

Another object of the present invention is to provide a method for preventing or treating a brain and nervous system disease characterized by the binding molecule, antibody or fragment thereof, antibody-drug conjugate (ADC), or chimeric antigen receptor (CAR) according to the present invention.

However, the technical problem to be achieved by the present invention is not limited to the above-mentioned problems, and other problems that are not mentioned will be clearly understood by a skilled person in the art from the following description.

Solution to Problem

According to an embodiment of the present invention, there is provided a binding molecule that specifically binds to leucine-rich and immunoglobulin-like domains 1 (Lrig-1) protein present on the surface of regulatory T cells (Treg cells).

As used herein, the term "binding molecule" refers to a variable domain comprising an intact immunoglobulin that includes a monoclonal antibody, such as a chimeric, humanized, or human monoclonal antibody, or an immunoglobulin that binds to an antigen, for example, an immunoglobulin fragment that competes with intact immunoglobulins for binding to monomeric HA or trimeric HA of influenza A virus. Regardless of the structure, an antigen-binding fragment binds to the same antigen recognized by intact immunoglobulins. The antigen-binding fragment may include a peptide or polypeptide which contains, out of the amino acid sequence of the binding molecule, an amino acid sequence of two or more contiguous residues, 20 or more contiguous amino acid residues, 25 or more contiguous amino acid residues, 30 or more contiguous amino acid residues, 35 or more contiguous amino acid residues, 40 or more contiguous amino acid residues, 50 or more contiguous amino acid residues, 60 or more contiguous amino acid residues, 70 or more contiguous amino acid residues, 80 or more contiguous amino acid residues, 90 or more contiguous amino acid residues, 100 or more contiguous amino acid residues, 125 or more contiguous amino acid residues, 150 or more contiguous amino acid residues, 175 or more contiguous amino acid residues, 200 or more contiguous amino acid residues, or 250 or more contiguous amino acid residues. The term “antigen-binding fragment”, in particular, includes Fab, F(ab'), F(ab') 2, Fv, dAb, Fd, complementarity determining region (CDR) fragments, single-chain antibodies (scFvs), bivalent single-chain antibodies, single-chain phage antibodies, unibodies, diabodies, triabodies, tetrabodies, polypeptides containing one or more fragments of immunoglobulin which is sufficient for a particular antigen to bind to the polypeptide, and the like. The fragment may be produced synthetically or by enzymatic or chemical digestion of a complete immunoglobulin, or may be produced by genetic engineering methods using recombinant DNA techniques. Production methods are well known in the art.

In the present invention, the “Lrig-1 protein” is a transmembrane protein consisting of 1091 amino acids present on the surface of regulatory T cells, and is composed of leucine-rich repeats (LRRs) and three immunoglobulin-like domains on the extracellular or lumen side, a cell transmembrane sequence, and a cytoplasmic tail portion. The LRIG gene family includes LRIG1, LRIG2, and LRIG3, and the amino acids therebetween are highly conserved. The LRIGI gene is highly expressed in normal skin and can be expressed in basal and hair follicle cells to regulate proliferation of epithelial stem cells. Therefore, the LRIGI gene plays an important role in maintaining homeostasis of the epidermis, and its absence may develop psoriasis or skin cancer. It has been reported that in a case where chromosome 3p14.3 portion in which LRIGI is located is cut off, there is a possibility of developing into cancer cells. In fact, it was identified that expression of LRIG1 is greatly decreased in renal cell carcinoma and cutaneous squamous cell carcinoma. Recently, it has been also found that Lrig-1 is expressed in only about 20 to 30% of cancers. On the other hand, for the purpose of the present invention, the Lrig-1 protein may be, but is not limited to, a protein present in humans or mice.

In the present invention, the Lrig-1 protein may be, but is not limited to, a human-derived polypeptide represented by SEQ ID NO: 1 or a mouse-derived polypeptide represented by SEQ ID NO: 3.

In addition, in the present invention, the Lrig-1 protein represented by SEQ ID NO: 1 may be encoded by a polynucleotide represented by SEQ ID NO: 2, but is not limited thereto.

In addition, in the present invention, the Lrig-1 protein represented by SEQ ID NO: 3 may be encoded by a polynucleotide represented by SEQ ID NO: 4, but is not limited thereto.

In the present invention, the binding molecule may be a binding molecule, comprising:

a heavy chain variable region that contains a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7; and a light chain variable region that contains a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

In the present invention, the binding molecule may be a binding molecule, comprising a heavy chain variable region consisting of the amino acid sequence represented by SEQ ID NO: 11; and a light chain variable region consisting of the amino acid sequence represented by SEQ ID NO: 12.

In the present invention, the binding molecule may be a binding molecule, comprising:

a heavy chain variable region that contains a heavy chain CDR1 encoded by the nucleotide sequence represented by SEQ ID NO: 13, a heavy chain CDR2 encoded by the nucleotide sequence represented by SEQ ID NO: 14, and a heavy chain CDR3 encoded by the nucleotide sequence represented by SEQ ID NO: 15; and a light chain variable region that contains a light chain CDR1 encoded by the nucleotide sequence represented by SEQ ID NO: 16, a light chain CDR2 encoded by the nucleotide sequence represented by SEQ ID NO: 17, and a light chain CDR3 encoded by the nucleotide sequence represented by SEQ ID NO: 18.

In the present invention, the binding molecule may be binding molecule, comprising:

a heavy chain variable region encoded by the nucleotide sequence represented by SEQ ID NO: 19; and a light chain variable region encoded by the nucleotide sequence represented by SEQ ID NO: 20.

In the present invention, the binding molecule may further comprise a fragment crystallization (Fc) region or a constant region. Here, the Fc region may be an Fc region of an IgA, IgD, IgE, IgM, IgG1, IgG2, IgG3, or IgG4 antibody, or may be derived therefrom. Alternatively, the Fc region may be a hybrid Fc region.

In the present invention, the Fc region may be an Fc region of a mammalian-derived IgA, IgD, IgE, IgM, IgG1, IgG2, IgG3, or IgG4 antibody, and may preferably be an Fc region of a human-derived IgA, IgD, IgE, IgM, IgG1, IgG2, IgG3, or IgG4 antibody. However, the Fc region is not limited thereto.

As an example of the present invention, the constant region may be a mouse-derived IgG2a constant region represented by SEQ ID NO: 21, but is not limited thereto.

As an example of the present invention, the constant region may be a mouse-derived immunoglobulin kappa constant region represented by SEQ ID NO: 22, but is not limited thereto.

As an example of the present invention, the constant region may be a human-derived IgG1 constant region represented by SEQ ID NO: 23 or 24, but is not limited thereto.

As an example of the present invention, the constant region may be a human-derived immunoglobulin kappa constant region represented by SEQ ID NO: 25 or 26, but is not limited thereto.

As an example of the present invention, the constant region may be a human-derived IgG2 constant region represented by SEQ ID NO: 27, but is not limited thereto.

As an example of the present invention, the constant region may be a human-derived IgG3 constant region represented by SEQ ID NO: 28, but is not limited thereto.

As an example of the present invention, the constant region may be a human-derived IgG4 constant region represented by SEQ ID NO: 29, but is not limited thereto.

As an example of the present invention, the constant region may be a constant region represented by SEQ ID NO: 30, but is not limited thereto.

As an example of the present invention, the constant region may be a constant region represented by SEQ ID NO: 31, but is not limited thereto.

As an example of the present invention, the Fc region may be a human-derived immunoglobulin lambda constant region, but is not limited thereto.

In the present invention, the "hybrid Fc" may be derived from a combination of human IgG subclasses or a combination of human IgD and IgG. In a case where the hybrid Fc binds to a biologically active molecule, polypeptide, or the like, the hybrid Fc has effects of not only increasing a serum half-life of the biologically active molecule, but also increasing an expression level of the polypeptide when a nucleotide sequence encoding the Fc-polypeptide fusion protein is expressed.

As an example of the present invention, the hybrid Fc region may be hybrid Fc represented by SEQ ID NO: 32, but is not limited thereto.

In the binding molecule of the present invention, the Fc or constant region may be linked, via a linker, to the variable region. Here, the linker may be linked to the C-terminus of the Fc or constant region, and the N-terminus of the binding molecule of the present invention may be linked to the linker. However, the present invention is not limited thereto.

In the present invention, the "linker" may contain a sequence that can be cleaved by an enzyme that is overexpressed in a tissue or cell having a target disease. In a case where the linker may be cleaved by the overexpressed enzyme as described above, it is possible to effectively prevent activity of a polypeptide from decreasing due to the Fc or constant region. In the present invention, an example of the linker may be preferably a peptide linker consisting of 33 amino acids located in the $282^{nd}$ to $314^{th}$ portion of human albumin which is most abundantly present in the blood, and more preferably a peptide linker consisting of 13 amino acids located in the $292^{nd}$ to $304^{th}$ portion of the human albumin. Such portions are portions which are mostly exposed to the outside in three-dimensional structure, and thus have a minimum possibility of inducing an immune response in the body. However, the linker is not limited thereto.

The binding molecule of the present invention may further comprise a heavy chain constant region consisting of an amino acid sequence selected from the group consisting of SEQ ID NOs: 21, 23, 24, 27, 28, 29, 30, and 32.

The binding molecule of the present invention may further comprise a light chain constant region consisting of the amino acid sequence represented by SEQ ID NO: 22, 25, 26, and 31.

The binding molecule of the present invention may further comprise:

- a heavy chain constant region consisting of the amino acid sequence represented by SEQ ID NO: 21; and
- a light chain constant region consisting of the amino acid sequence represented by SEQ ID NO: 22.

The binding molecule of the present invention may further comprise:

- a heavy chain constant region represented by an amino acid sequence represented by SEQ ID NO: 23, 24, 27, 28, 29, and 30; and
- a light chain constant region represented by an amino acid sequence represented by SEQ ID NO: 25, 26, and 31.

The binding molecule of the present invention may further comprise:

- a heavy chain constant region consisting of the amino acid sequence represented by SEQ ID NO: 24; and
- a light chain constant region consisting of the amino acid sequence represented by SEQ ID NO: 26.

The binding molecule of the present invention may further comprise:

- a heavy chain constant region consisting of the amino acid sequence represented by SEQ ID NO: 30; and
- a light chain constant region consisting of the amino acid sequence represented by SEQ ID NO: 31.

The binding molecule of the present invention may further comprise:

- a heavy chain constant region consisting of the amino acid sequence represented by SEQ ID NO: 32.

The binding molecule of the present invention may further comprise:

- a heavy chain constant region encoded by the nucleotide sequence represented by SEQ ID NO: 33 or 35; and
- a light chain constant region encoded by the nucleotide sequence represented by SEQ ID NO: 34 or 36.

The binding molecule of the present invention may be a binding molecule comprising a heavy chain consisting of the amino acid sequence represented by SEQ ID NO: 37 or 38 and a light chain consisting of the amino acid sequence represented by SEQ ID NO: 39 or 40.

The binding molecule of the present invention may be a binding molecule comprising a heavy chain consisting of the amino acid sequence represented by SEQ ID NO: 37 and a light chain consisting of the amino acid sequence represented by SEQ ID NO: 39.

The binding molecule of the present invention may be a binding molecule comprising a heavy chain consisting of the amino acid sequence represented by SEQ ID NO: 38 and a light chain consisting of the amino acid sequence represented by SEQ ID NO: 40.

The binding molecule of the present invention may be a binding molecule comprising a heavy chain encoded by the nucleotide sequence represented by SEQ ID NO: 41 or 43 and a light chain encoded by the nucleotide sequence represented by SEQ ID NO: 42 or 44.

The binding molecule of the present invention may be a binding molecule comprising a heavy chain encoded by the nucleotide sequence represented by SEQ ID NO: 41 and a light chain encoded by the nucleotide sequence represented by SEQ ID NO: 42.

The binding molecule of the present invention may be a binding molecule comprising a heavy chain encoded by the nucleotide sequence represented by SEQ ID NO: 43 and a light chain encoded by the nucleotide sequence represented by SEQ ID NO: 44.

The binding molecule of the present invention is characterized by being an antibody or a fragment thereof, but is not limited thereto. The antibody includes all of a monoclonal antibody, a full-length antibody, or an antibody fragment which is a portion of an antibody, has the ability to bind to Lrig-1 protein, and can compete with the binding molecule of the present invention in binding to an epitope on Lrig-1.

As used herein, the term "antibody" refers to a protein molecule which serves as a receptor that specifically recognizes an antigen, including an immunoglobulin molecule that is immunologically reactive with a particular antigen. For the purpose of the present invention, the antigen may be Lrig-1 protein present on the surface of regulatory T cells. Preferably, the antibody may specifically recognize the leucine-rich region or immunoglobulin-like domain of the Lrig-1 protein, but is not limited thereto.

In the present invention, the "immunoglobulin" has a heavy chain and a light chain, and each of the heavy chain and the light chain comprises a constant region and a variable region. The variable region of each of the light chain and the heavy chain contains three hypervariable regions called complementarity determining regions (hereinafter referred to as "CDRs") and four framework regions.

The CDRs primarily serve to bind to an epitope on an antigen. The CDRs of each chain are typically referred to as CDR1, CDR2, and CDR3 sequentially starting from the N-terminus, and are also distinguished by the chain where particular CDRs are located.

In addition, as used herein, the term "monoclonal antibody" refers to an antibody molecule of a single molecular composition which is obtained from substantially the same antibody population, and exhibits single binding specificity and affinity for a particular epitope.

In the present invention, the "full-length antibody" has a structure with two full-length light chains and two full-length heavy chains in which each light chain is linked to a heavy chain by a disulfide bond, and includes IgA, IgD, IgE, IgM, and IgG. The IgG includes, as subtypes thereof, IgG1, IgG2, IgG3, and IgG4.

In addition, as used herein, the term "antigen fragment" refers to a fragment that retains an antigen-binding function, and includes Fab, Fab', F(ab') 2, Fv, and the like. The Fab has a structure with variable regions of light and heavy chains, a constant region of the light chain, and a first constant region (CH1 domain) of the heavy chain, and has one antigen-binding site. In addition, Fab' is different from Fab in that Fab' has a hinge region containing at least one cysteine residue at the C-terminus of the heavy chain CH1 domain. F(ab') 2 antibodies are produced with cysteine residues at the hinge region of Fab' forming a disulfide bond. Fv (variable fragment) refers to the smallest antibody fragment having only a heavy chain variable region and a light chain variable region. Double-chain Fv (dsFv) is configured to be such that a heavy chain variable region and a light chain variable region are linked to each other by a disulfide bond, and single-chain Fv (scFv) is configured to be such that a heavy chain variable region and a light chain variable region are covalently linked to each other, in general, via a peptide linker. The antibody fragment may be obtained as Fab or F(ab') 2 fragment in a case where a proteolytic enzyme, for example, papain or pepsin is used, and may be produced through a genetic recombinant technique.

In addition, in the present invention, the antibody may be, but is not limited to, a chimeric antibody, a humanized antibody, a bivalent, bispecific molecule, a minibody, a domain antibody, a bispecific antibody, an antibody mimetic, a unibody, a diabody, a triabody, or a tetrabody, or a fragment thereof. In the present invention, the "chimeric antibody" is an antibody which is obtained by recombination of a variable region of a mouse antibody and a constant region of a human antibody, and has a greatly improved immune response as compared with the mouse antibody.

In addition, as used herein, the term "humanized antibody" refers to an antibody obtained by modifying a protein sequence of an antibody derived from a non-human species so that the protein sequence is similar to an antibody variant naturally produced in humans. For example, the humanized antibody may be prepared as follows. Mouse-derived CDRs may be recombined with a human antibody-derived FR to prepare a humanized variable region, and the humanized variable region may be recombined with a constant region of a preferred human antibody to prepare a humanized antibody.

In the present invention, the binding molecule may be provided as a bispecific antibody or a bispecific antigen-binding fragment which is capable of binding to Lrig-1 protein and also binding to another protein.

In the present invention, the bispecific antibody and the bispecific antigen-binding fragment may comprise the binding molecule according to the present invention. As an example of the present invention, the bispecific antibody and the bispecific antigen-binding fragment comprise an antigen-binding domain capable of binding to Lrig-1 protein, wherein the antigen-binding domain capable of binding to Lrig-1 protein may comprise or consist of the binding molecule according to the present invention.

The bispecific antibody and the bispecific antigen-binding fragment provided in the present invention comprise an antigen-binding domain, which is a binding molecule capable of binding to Lrig-1 protein according to the present invention, and an antigen-binding domain capable of binding to another target protein. Here, the antigen-binding domain capable of binding another target protein may be an antigen-binding domain capable of binding to a protein other than Lrig-1 protein, for example, but not limited to, PD-1 or a cell surface receptor. However, the antigen-binding domain is not limited thereto.

The bispecific antibody and the bispecific antigen-binding fragment according to the present invention may be provided in any suitable format. For example, the bispecific antibody or the bispecific antigen-binding fragment may be a bispecific antibody conjugate (for example, IgG2, F(ab') 2, or CovX-body), a bispecific IgG or IgG-like molecule (for example, IgG, scFv4-Ig, IgG-scFv, scFv-IgG, DVD-Ig, IgG-sVD, sVD-IgG, or 2 in 1-IgG, mAb2, or Tandemab common LC), an asymmetric bispecific IgG or IgG-like molecule (for example, kih IgG, kih IgG common LC, CrossMab, kih IgG-scFab, mAb-Fv, charge pair, or SEED-body), a small bispecific antibody molecule (for example, diabody (Db), dsDb, DART, scDb, tandAb, tandem scFv (taFv), tandem dAb/VHH, triple body, triple head, Fab-scFv, or F(ab') 2-scFv2), a bispecific Fc and CH3 fusion protein (for example, taFv-Fc, di-diabody, scDb-CH3, scFv-Fc-scFv, HCAb-VHH, scFv-kih-Fc, or scFv-kih-CH3), or a bispecific fusion protein (for example, scFv2-albumin, scDb-albumin, taFv-toxin, DNL-Fab3, DNL-Fab4-IgG, DNL-Fab4-IgG-cytokine 2). The bispecific antibody and the bispecific antigen-binding fragment according to the invention may be designed and prepared by those skilled in the art.

A method for producing the bispecific antibody in the present invention comprises forming a reducing disulfide or non-reducing thioether bond, and chemical crosslinking of an antibody or antibody fragment. For example, N-succinimidyl-3-(-2-pyridyldithio)-propionate (SPDP) may be used, for example, for chemically crosslinking a Fab fragment through an SH-group at the hinge region, to generate a disulfide-linked bispecific F (ab) 2 heterodimer.

In addition, an alternative method for producing the bispecific antibody in the present invention comprises fusing an antibody-producing hybridoma with, for example, polyethylene glycol, to produce quadroma cells capable of secreting bispecific antibodies.

The bispecific antibody and the bispecific antigen-binding fragment according to the invention may also be, for example, recombinantly produced by expression from a nucleic acid construct that encodes a polypeptide for an antigen-binding molecule.

For example, a DNA construct that contains a sequence encoding light and heavy chain variable domains for two antigen-binding domains (that is, light and heavy chain variable domains for an antigen-binding domain capable of binding to PD-1, and light and heavy chain variable domains for an antigen-binding domain capable of binding to another target protein), and a sequence encoding a suitable linker or dimerization domain between the antigen-binding domains may be prepared by molecular cloning techniques. Subsequently, a recombinant bispecific antibody may be produced by expression of the construct (for example, in vitro) in a suitable host cell (for example, a mammalian host cell), and then the expressed recombinant bispecific antibody may be optionally purified.

Antibodies may be produced by an affinity maturation process in which a modified antibody with improved affinity for an antigen as compared with an unmodified parent antibody is produced. An affinity matured antibody may be produced by a procedure known in the art.

In addition, the binding molecule provided in the present invention may include a variant of the amino acid sequence as long as the variant can specifically bind to Lrig-1 protein. For example, in order to improve binding affinity and/or other biological properties of an antibody, modifications may be made to an amino acid sequence of the antibody. Such modifications include, for example, deletions, insertions, and/or substitutions of amino acid sequence residues of the antibody.

Such amino acid variations are made based on relative similarity of amino acid side chain substituents such as hydrophobicity, hydrophilicity, charge, and size. According to analysis on sizes, shapes, and types of amino acid side chain substituents, it can be seen that arginine, lysine, and histidine are all positively charged residues; alanine, glycine, and serine have similar sizes; and phenylalanine, tryptophan, and tyrosine have similar shapes. Thus, based on these considerations, it can be said that arginine, lysine, and histidine; alanine, glycine, and serine; and phenylalanine, tryptophan, and tyrosine are biologically functional equivalents.

In introducing variations, the hydropathic index of amino acids may be considered. Each amino acid has been assigned hydropathic index depending on its hydrophobicity and charge: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The hydropathic amino acid index is very important in conferring the interactive biological function on a protein. It is known that substitution with an amino acid having similar hydropathic index allows a protein to retain similar biological activity. In a case where variations are introduced with reference to the hydropathic index, substitutions are made between amino acids that exhibit a hydropathic index difference of preferably within +2, more preferably within +1, and even more preferably within +0.5.

Meanwhile, it is also well known that substitutions between amino acids having similar hydrophilicity values result in proteins with equivalent biological activity. As disclosed in U.S. Pat. No. 4,554,101, respective amino acid residues have been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In a case where variations are introduced with reference to the hydrophilicity values, substitutions may be made between amino acids that exhibit a hydrophilicity value difference of preferably within +2, more preferably within +1, and even more preferably within =0.5.

Amino acid exchanges in proteins which do not entirely alter activity of a molecule are known in the art. The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Gln/Glu.

Given the above-described variations with biologically equivalent activity, it is interpreted that the binding molecule of the present invention also includes sequences that exhibit substantial identity with the sequences listed in the Sequence Listing.

As used herein, the term "substantial identity" refers to a sequence showing at least 61% homology, more preferably 70% homology, even more preferably 80% homology, and most preferably 90% homology when the sequence of the present invention is aligned with any other sequence so that they maximally correspond to each other, and the aligned sequence is analyzed by using an algorithm typically used in the art. Alignment methods for comparison of sequences are known in the art. NCBI Basic Local Alignment Search Tool (BLAST) is accessible from the National Center for Biological Information (NBCI), or the like, and may be used in conjunction with sequencing programs, such as blastp, blasm, blastx, tblastn, and tblastx, on the internet. BLAST is accessible at http://www.ncbi.nlm.nih.gov/BLAST/. Sequence homology comparison methods using this program can be identified online (http://www.ncbi.nlm.nih.gov/BLAST/blast_help.html).

In the present invention, the binding molecule, preferably the antibody, may be produced by a conventional method for producing an antibody, and may be produced by affinity maturation.

As used herein, the term "affinity maturation" refers to a process in which antibodies having increased affinity for an antigen are produced by activated B cells in the course of an immune response. For the purpose of the present invention, the affinity maturation allows antibodies or antibody fragments to be produced due to affinity maturation based on the principles of mutation and selection, in the same process that occurs in nature.

The binding molecule, preferably the antibody, provided in the present invention can effectively prevent, ameliorate, or treat brain and nervous system diseases, in particular, neurodegenerative diseases or neuroinflammatory diseases.

According to another embodiment of the present invention, there is provided a nucleic acid molecule encoding the binding molecule provided in the present invention.

The nucleic acid molecule of the present invention includes all nucleic acid molecules obtained by translating the amino acid sequences of the binding molecules provided in the present invention to polynucleotide sequences, as known to those skilled in the art. Therefore, various polynucleotide sequences may be prepared by an open reading frame (ORF), and all of these polynucleotide sequences are also included in the nucleic acid molecule of the present invention.

The nucleic acid molecule of the present invention may comprise a heavy chain encoded by the nucleotide sequence represented by SEQ ID NO: 41 or 43 and a light chain encoded by the nucleotide sequence represented by SEQ ID NO: 42 or 44.

The nucleic acid molecule of the present invention may comprise a heavy chain encoded by the nucleotide sequence represented by SEQ ID NO: 41 and a light chain encoded by the nucleotide sequence represented by SEQ ID NO: 42.

The nucleic acid molecule of the present invention may comprise a heavy chain encoded by the nucleotide sequence represented by SEQ ID NO: 43 and a light chain encoded by the nucleotide sequence represented by SEQ ID NO: 44.

According to another embodiment of the present invention, there is provided an expression vector into which the isolated nucleic acid molecule provided in the present invention is inserted.

In the present invention, the "vector" is a nucleic acid molecule capable of transporting another nucleic acid linked thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form of vector.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Quu, T-even, T2, T3, T7; plant viruses. Any expression vector known, to those skilled in the art, as expression vectors can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to another embodiment of the present invention, there is provided a host cell line transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium*; fungal cells such as yeast cells and *Pichia pastoris*; insect cells such as *Drosophila* and *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell line is available.

According to another embodiment of the present invention, there is provided an antibody-drug conjugate (ADC) comprising the antibody provided in the present invention and a drug.

As used herein, the term "antibody-drug conjugate (ADC)" refers to a form in which the drug and the antibody are chemically linked to each other without degrading biological activity of the antibody and the drug. In the present invention, the antibody-drug conjugate denotes a form in which the drug is bound to an amino acid residue at the N-terminus of the heavy and/or light chain of the antibody, specifically, a form in which the drug is bound to an α-amine group at the N-terminus of the heavy and/or light chain of the antibody.

In the present invention, examples of the reactive group capable of reacting and crosslinking with the α-amine group are not particularly limited in terms of type as long as the reactive group can react and crosslink with an α-amine group at the N-terminus of a heavy or light chain of an antibody. The reactive group includes all types of groups known in the art which react with an amine group. The reactive group may, for example, be any one of isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester, but is not limited thereto.

As used herein, the term "drug" may mean any substance having a certain biological activity for a cell, which is a concept including DNA, RNA, or a peptide. The drug may be in a form which contains a reactive group capable of reacting and crosslinking with an α-amine group, and also includes a form which contains a reactive group capable of reacting and crosslinking with an α-amine group and to which a linker is linked.

According to another embodiment of the present invention, there is provided a pharmaceutical composition for preventing or treating a brain and nervous system disease comprising, as an active ingredient, a chimeric antigen receptor (CAR) comprising an antigen-specific binding domain, a linking domain and a CD3 zeta (ζ) signaling domain.

As used herein, the term "chimeric antigen receptor" or "CAR" refers to an engineered receptor comprising an extracellular antigen binding domain and an intracellular signaling domain. Although the most common type of CAR comprises a single chain variable fragment (scFv) derived from a monoclonal antibody fused to the transmembrane and intracellular domains of a T cell co-receptor, such as the CD3 zeta (ζ) chain, the present invention is not limited to these domains. Rather, the "chimeric antigen receptor" or "CAR" as used herein refers to any receptor engineered to express any intracellular signaling molecule and any extracellular antigen binding domain fused or linked thereto. In the present invention, the binding domain may comprise a single chain variable fragment (scFv) capable of specifically recognizing the Lrig-1 protein. In the present invention, the term "single chain variable fragment" or "scFv" refers to a fusion protein of a variable heavy chain (VH) and a variable light chain (VL) of an antibody by a peptide linker between VL and VH.

In addition, in the present invention, the VH domain and the VL domain may be connected through a flexible linker. In the present invention, the flexible linker may be a glycine/serine linker of about 10 to 30 amino acids (e.g., 30, 25, 20, 19, 18, 17, 16, 15, 14, 13, 12, 11, 10, 9, 8, 7, 6, or 5 amino acids), preferably 15 amino acids in length. In the present invention, the linker length can act as an important determining site for chimeric antigen receptors, so a linker shorter than the above range can increase affinity, but can also cause intracellular multimer formation to impair CAR expression, while linkers longer than this range may reduce antigen affinity by moving the VL and VH CDRs farther apart in proximity.

The chimeric antigen receptor of the present invention may further comprise at least one of a hinge region (or spacer) and a signaling domain. In the present invention, the hinge region is a region connecting antigen-binding domain and the transmembrane domain, and is also called a "spacer," and has the purpose of extending the antigen-binding domain from the T cell membrane or the NK cell membrane. In the present invention, the hinge region can be obtained from any suitable sequence from any genus, including, for example, human or parts thereof, or may include CD8, CD28, 4-1BB, OX40, all or part of the CD3 zeta (5) chain, T cell receptor α or β chain, CD28, CD38, CD45, CD4, CD5, CD8, CD9, CD16, CD22, CD33, CD37, CD64, CD80, CD86, CD134, CD137, ICOS, CD154, functional derivatives thereof, or combinations thereof commonly used in the art, but is not limited thereto. In addition, the hinge region may comprise one selected from immunoglobulins (e.g., IgG1, IgG2, IgG3, IgG4, and IgD) without being limited to immunoglobulins, but is not limited thereto.

In the present invention, the signaling domain refers to a part of a chimeric antigen receptor found or engineered to be found inside a T cell. The signaling domain may or may not comprise a transmembrane that serves to fix the chimeric antigen receptor in the plasma membrane of T cells. The transmembrane domain and the signaling domain may be derived from the same protein (e.g., CD3 zeta (ζ) molecule), or the transmembrane domain and the signaling domain may be derived from different proteins (e.g., transmembrane domain of CD28 and intracellular signaling domain of CD3 zeta (ζ) molecule, or vice versa).

In the present invention, the transmembrane domain comprises, for example, T cell receptor α or β chain, all or part of the CD3 zeta (ζ) chain, CD28, CD3ε, CD45, CD4, CD5, CD8, CD9, CD16, CD22, CD33, CD37, CD64, CD80, CD86, CD134, CD137, ICOS, CD154, functional derivatives thereof, or combinations thereof, but is not limited thereto. The costimulatory domain may comprise 4-1BB (CD137), OX40, CD27, CD28, CD30, CD40, PD-1, CD2, CD7, CD258, natural killer group 2 member C (NKG2C), natural killer group 2 member (NKG2D), B7-H3, CD83, ICAM-1, ligands that bind to LFA-1 (CD11a/CD18) or ICOS, active fragments thereof, functional derivatives thereof, or a functional signaling domain derived from a polypeptide comprising a combination thereof, but is not limited thereto.

In the present invention, the signaling domain may comprise a functional signaling domain derived from polypeptides comprising all or part of CD3 zeta (ζ), common FcR gamma (FcER1G), FcgammaRIIIa, FcRbeta (Fc epsilon lip), CD3gamma, CD3delta, CD3 epsilon, CD79a, CD79b, DNAX-activating protein 10 (DAP10), DNAX-activating protein 12 (DAP12), an active fragment thereof, a functional derivative thereof, or a combination thereof, but is not limited thereto, and such signaling domains are known in the art.

According to one embodiment of the present invention, in the chimeric antigen receptor (CAR) comprising an antigen-specific binding domain, a linking domain and a CD3 zeta (¿) signaling domain, there is provided a chimeric antigen receptor wherein the specific binding domain is a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

In the present invention, the drug may include any drug regardless of type as long as the drug can treat brain and nervous system diseases, in particular, neurodegenerative diseases or neuroinflammatory diseases.

According to another embodiment of the present invention, the present invention relates to a composition for preventing, ameliorating, or treating a brain and nervous system disease comprising the binding molecule, nucleic acid molecule, expression vector, host cell line, or antibody-drug conjugate (ADC) of the present invention as an active ingredient.

The brain and nervous system disease to be prevented, ameliorated, or treated by the composition provided in the present invention may be a neurodegenerative disease or neuroinflammatory disease.

In the present invention, the "neurodegenerative disease" may refer to a disease caused by decreased function or loss of neurons, and the "neuroinflammatory disease" may refer to a disease caused by excessive inflammatory responses in the nervous system. As a specific example, the neurodegenerative disease or neuroinflammatory disease in the present invention may be selected from, but is not limited to, the group consisting of stroke, dementia, Alzheimer's disease, Parkinson's disease, Huntington's disease, Niemann-Pick disease, multiple sclerosis, prion disease, Creutzfeldt-Jakob disease, frontotemporal dementia, dementia with Lewy bodies, amyotrophic lateral sclerosis, paraneoplastic syndrome, cortical degeneration syndrome, multiple system atrophy, progressive supranuclear palsy, nervous system autoimmune disease, spinocerebellar ataxia, inflammatory and neuropathic pain, cerebrovascular disease, spinal cord injury, and tauopathy.

In addition, the composition provided in the present invention may be used as a pharmaceutical composition or a food composition. However, the present invention is not limited thereto.

In the present invention, the "prevention" may include, without limitation, any act of blocking symptoms caused by a neurodegenerative disease or neuroinflammatory disease, or suppressing or delaying the symptoms, using the composition of the present invention.

In the present invention, the "treatment" or "amelioration" may include, without limitation, any act capable of ameliorating or beneficially altering symptoms caused by a neurodegenerative disease or neuroinflammatory disease, using the composition of the present invention.

In the present invention, the pharmaceutical composition may be characterized by being in the form of capsules, tablets, granules, injections, ointments, powders, or beverages, and the pharmaceutical composition may be characterized by being targeted to humans.

The pharmaceutical composition of the present invention may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition according to the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

In the present invention, the "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, frequency of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

The food composition that includes the composition of the present invention may be prepared in the form of various foods, for example, beverages, gums, tea, vitamin complexes, powders, granules, tablets, capsules, confections, rice cakes, bread, and the like. The food composition of the present invention is composed of a plant extract having little toxicity and side effects, and thus can be used without worries in a case of being ingested for a long time for preventive purposes.

When the composition of the present invention is included in the food composition, it may be added in an amount corresponding to a rate of 0.1% to 50% of the total weight.

Here, in a case where the food composition is prepared in the form of beverages, there is no particular limitation except that the beverage contains the food composition at an indicated proportion, and the beverage may contain various flavoring agents, natural carbohydrates, or the like as additional ingredients, similarly to conventional beverages. That is, examples of the natural carbohydrates may include monosaccharides such as glucose, disaccharides such as fructose, polysaccharides such as sucrose, conventional sugars such as dextrin and cyclodextrin, and sugar alcohol such as xylitol, sorbitol, and erythritol. Examples of the flavoring agents may include natural flavoring agents (thaumatin, *stevia* extracts (such as rebaudioside A), glycyrrhizin, and the like) and synthetic flavoring agents (saccharin, aspartame, and the like).

In addition, the food composition of the present invention may contain various nutrients, vitamins, minerals (electrolytes), flavorings such as synthetic flavorings and natural flavorings, colorants, pectic acid and salts thereof, alginic acid and salts thereof, organic acids, protective colloidal thickeners, pH adjusting agents, stabilizers, preservatives, glycerin, alcohol, carbonizing agents used in carbonated beverages, and the like.

These ingredients may be used individually or in combination. A proportion of such additives is not so important, and is generally selected from the range of 0.1 to about 50 parts by weight per 100 parts by weight of the composition of the present invention.

According to still yet another embodiment of the present invention, there is provided a method for preventing, ameliorating, or treating a brain and nervous system disease, comprising a step of administering, to an individual in need thereof, the binding molecule provided in the present invention; a nucleic acid molecule encoding the binding molecule; an expression vector into which the nucleic acid molecule is inserted; a host cell line transfected with the expression vector; or the antibody-drug conjugate (ADC) provided in the present invention.

In the present invention, the "individual" is an individual suspected of developing a brain and nervous system disease, and the individual suspected of developing a brain and nervous system disease means a mammal, such as mice and domestic animals, including humans, who has developed or is likely to develop the disease in question. However, any individual, who is treatable with the active substance provided in the present invention, is included therein without limitation.

The brain and nervous system disease treated by the method of the present invention may be a neurodegenerative disease or neuroinflammatory disease. As a specific example, the neurodegenerative disease or neuroinflammatory disease in the present invention may be selected from, but is not limited to, the group consisting of stroke, dementia, Alzheimer's disease, Parkinson's disease, Huntington's disease, Niemann-Pick disease, multiple sclerosis, prion disease, Creutzfeldt-Jakob disease, frontotemporal dementia, dementia with Lewy bodies, amyotrophic lateral sclerosis, paraneoplastic syndrome, cortical degeneration syndrome, multiple system atrophy, progressive supranuclear palsy, nervous system autoimmune disease, spinocerebellar ataxia, inflammatory and neuropathic pain, cerebrovascular disease, spinal cord injury, and tauopathy.

The method of the present invention may comprise a step of administering, in a pharmaceutically effective amount, the binding molecule provided in the present invention; a nucleic acid molecule encoding the binding molecule; an expression vector into which the nucleic acid molecule is inserted; a host cell line transfected with the expression vector; or the antibody-drug conjugate (ADC) provided in the present invention.

An appropriate total daily amount used may be determined by an attending physician or veterinarian within the scope of sound medical judgment, and administration may be made once or several times. However, for the purposes of the present invention, a specific therapeutically effective amount for a particular patient is preferably applied differently depending on various factors, including type and degree of reaction to be achieved, the specific composition comprising the active ingredient, including whether other agents are used therewith as the case may be, the patient's age, body weight, general health status, sex, and diet, frequency of administration, route of administration, secretion rate of the composition comprising the active ingredient, duration of treatment, and drugs used simultaneously or in combination with the specific composition, and similar factors well known in the medical field.

Meanwhile, the method for preventing or treating a brain and nervous system disease may be, but is not limited to, a combination therapy that further comprises a step of administering a compound or substance having therapeutic activity against one or more diseases.

In the present invention, the "combination" should be understood to represent simultaneous, individual, or sequential administration. In a case where the administration is made in a sequential or individual manner, the second component should be administered at intervals such that beneficial effects of the combination are not lost.

In the present invention, the dosage of the binding molecule or the antibody-drug conjugate may be, but is not limited to, about 0.0001 μg to 500 mg per kg of patient's body weight.

According to another embodiment of the present invention, there is provided a diagnostic composition for an immune-related disease comprising an agent for measuring the expression level of the Lrig-1 protein or its extracellular domain or a gene encoding the Lrig-1 protein present on the surface of a T cell using the binding molecule of the present invention.

The T cells of the present invention may be regulatory T cells.

The diagnostic composition of the present invention may comprise, for example, an agent that measures the expression level of the Lrig-1 protein or its extracellular domain or a gene encoding the Lrig-1 protein present on the surface of an activated regulatory T cell, that is, regulatory T cells with activated suppression of effector T cells, but is not limited thereto.

The diagnostic composition of the present invention may further comprise a protein, more than one selected from the group consisting of CD25, TIGIT, LAG3, CTLA-4, GITR, OX40, ICOS, PD-1, TIM-3, CCR4, FR4, CD15s, PI-16, and Lrig-1 proteins present on the surface of T cells, and an agent for measuring the expression level of a gene encoding the same. As such, when the expression level of various proteins or genes encoding such is further measured on the surface of T cells, a significant synergistic effect can be achieved in diagnosing the target disease compared to measuring the Lrig-1 protein or its extracellular domain or gene encoding it alone.

Although the agent measuring the expression level of the Lrig-1 protein or its extracellular domains of the present invention, and the expression level of more than one protein selected from the group consisting of CD25, TIGIT, LAG3, CTLA-4, GITR, OX40, ICOS, PD-1, TIM-3, CCR4, FR4, CD15s, PI-16, and Lrig-1 protein are not particularly limited, it may comprise, for example, at least one selected from the group consisting of an antibody, oligopeptide, ligand, peptide nucleic acid (PNA), and aptamer that specifically binds to the protein.

The agent measuring the expression level of the gene encoding the Lrig-1 protein of the present invention (in other words, LAIR1) or the gene encoding the extracellular domain of the Lrig-1 protein, and a gene encoding more than one protein selected from the group consisting of CD25, TIGIT, LAG3, CTLA-4, GITR, OX40, ICOS, PD-1, TIM-3, CCR4, FR4, CD15s, PI-16, and Lrig-1 may comprise at least one selected from the group consisting of a primer, probe, LNA, and antisense nucleotides that specifically bind to the gene.

As used herein, the term "primer" refers to a fragment that recognizes a target gene sequence, and consists of a forward and reverse primer pair, but preferably provides analysis results with specificity and sensitivity. High specificity can be imparted when the primers amplify the target gene sequence containing complementary primary binding sites while not causing non-specific amplification because the nucleic acid sequence of the primer is inconsistent with the non-target sequence present in the sample.

As used herein, the term "probe" refers to a substance that can specifically bind to a target substance to be detected in a sample, and a substance that can specifically confirm the presence of a target substance in a sample through binding. Given probes are commonly used in the art, the type of probe is not limited, but preferably can be peptide nucleic acid (PNA), locked nucleic acid (LNA), peptide, polypeptide, protein, RNA, or DNA, with PNA being the most preferred. More specifically, the probe is a biomaterial that includes those derived from or similar to those from living organisms or those manufactured in vitro, for example, enzymes, proteins, antibodies, microorganisms, animal and plant cells and organs, nerve cells, DNA, and RNA. DNA may comprise cDNA, genomic DNA and oligonucleotides, while RNA may comprise genomic RNA, mRNA, oligonucleotides, while proteins may comprise antibodies, antigens, enzymes, peptides, and the like.

According to another embodiment of the present invention, there is provided a diagnostic composition for a brain and nervous system disease, comprising the binding molecule provided in the present invention.

In the present invention, the kit may be, but is not limited to, an RT-PCR kit, a DNA chip kit, an ELISA kit, a protein chip kit, a rapid kit, or a multiple reaction monitoring (MRM) kit.

The diagnostic kit of the present invention may further include one or more other component compositions, solutions, or devices suitable for assay methods. For example, the diagnostic kit of the present invention may further include essential elements required for performing reverse transcription polymerase reaction. The kit for reverse transcription polymerase reaction includes a pair of primers specific for a gene encoding a marker protein. The primer pair is a nucleotide having a sequence specific to a nucleic acid sequence of the gene, and may have a length of about 7 bp to 50 bp, or about 10 bp to 30 bp. The kit may also include a primer pair specific for a nucleic acid sequence of a control gene. In addition to those mentioned above, the kit for reverse transcription polymerase reaction may include test tubes or other suitable containers, reaction buffers (with varying pH and magnesium concentrations), deoxynucleotides (dNTPs), enzymes such as Taq-polymerase and reverse transcriptase, DNase and RNase inhibitors, DEPC-treated water, sterilized water, and the like.

In addition, the diagnostic kit of the present invention may include essential elements required for performing a DNA chip assay. The DNA chip kit may include a substrate to which a cDNA or oligonucleotide corresponding to a gene or a fragment thereof is attached; reagents, agents, and enzymes for preparing a fluorescence-labeled probe; and the like. The substrate may also contain a cDNA or oligonucleotide corresponding to a control gene or a fragment thereof.

In addition, the diagnostic kit of the present invention may include essential elements required for performing ELISA. The ELISA kit includes an antibody specific for the marker protein. The antibodies are antibodies with high specificity and affinity for the marker protein and little cross-reactivity with other proteins, and include monoclonal antibodies, polyclonal antibodies, or recombinant antibodies. The ELISA kit may also include an antibody specific for a control protein. In addition to those mentioned above, the ELISA kit may include reagents capable of detecting bound antibodies, for example, labeled secondary antibodies, chromophores, enzymes (which are, for example, conjugated with an antibody) and substrates thereof, and other substances capable of binding to antibodies.

According to another embodiment of the present invention, the present invention relates to a method for providing information on diagnosis of an immune-related disease comprising a step of measuring the expression level of Lrig-1 protein or extracellular domain thereof present on the surface of T cells in a biological sample isolated from a target subject using the binding molecule of the present invention, or the expression level of a gene encoding such.

The T cells of the present invention may be regulatory T cells.

The step of measuring the expression level of the present invention may be to further measure the expression levels of a protein, more than one selected from the group consisting of CD25, TIGIT, LAG3, CTLA-4, GITR, OX40, ICOS, PD-1, TIM-3, CCR4, FR4, CD15s, PI-16, and Lrig-1 proteins present on the surface of T cells, or the expression levels of a gene encoding the same. As such, when the expression level of various proteins or genes encoding such is further measured on the surface of T cells, a significant synergistic effect can be achieved in diagnosing the target disease compared to measuring the Lrig-1 protein or the gene encoding it alone.

In the present invention, the "target individual" refers to an individual for whom it is uncertain whether the disease has developed and who has a high probability of developing the disease.

In the present invention, the "biological sample" may refer to any material, biological fluid, tissue or cell obtained or derived from an individual, and can comprise, for example, whole blood, leukocytes, peripheral blood mononuclear cells, buffy coat, plasma, serum, sputum, tears, mucus, nasal washes, nasal aspirates, breath, urine, semen, saliva, peritoneal washings, pelvic fluids, cystic fluid, meningeal fluid, amniotic fluid, glandular fluid, pancreatic fluid, lymph fluid, pleural fluid, nipple aspirate, bronchial aspirate, synovial fluid, joint aspirate, organ secretions, cells, cell extracts, or cerebrospinal fluid, but is not limited thereto.

The Lrig-1 protein or extracellular domain thereof of the present invention may be expressed on the cell surface of T cells, in particular, regulatory T cells, for example, activated regulatory T cells, that is the cell surface of activated regulatory T cells with activated suppressive ability of effector T cells.

In the present invention, examples of the method for measuring or comparatively analyzing the expression level of the Lrig-1 protein, extracellular domain thereof, and more than one protein selected from the group consisting of CD25, TIGIT, LAG3, CTLA-4, GITR, OX40, ICOS, PD-1, TIM-3, CCR4, FR4, CD15s, PI-16 and Lrig-1 include, but are not limited to, protein chip assay, immunoassay, ligand binding assay, matrix assisted laser desorption/ionization time of flight mass spectrometry (MALDI-TOF), sulface enhanced laser desorption/ionization time of flight mass spectrometry (SELDI-TOF), radioimmunoassay, radial immunodiffusion, ouchterlony immunodiffusion, rocket immunoelectrophoresis, immunohistochemical staining, complement fixation assay, two-dimensional electrophoresis, liquid chromatography-mass spectrometry (LC-MS), liquid chromatography-mass spectrometry/mass spectrometry (LC-MS/MS), Western blotting, and enzyme linked immunosorbent assay (ELISA).

The analysis method for measuring the expression level of a gene in order to confirm the presence and expression level of genes encoding the Lrig-1 protein or its extracellular domain, and more than one protein selected from the group consisting of CD25, TIGIT, LAG3, CTLA-4, GITR, OX40, ICOS, PD-1, TIM-3, CCR4, FR4, CD15s, PI-16 and Lrig-1 may be, but is not limited to, reverse transcription polymerase reaction (RT-PCR), competitive RT-PCR, real-time RT-PCR, RNase protection assay (RPA), Northern blotting or DNA chip.

In the present invention, the method may comprise a step of predicting that the target individual has a high probability of developing an immune-related disease in a case where the expression level of Lrig-1 protein or its extracellular domain, or the gene encoding it measured in the biological sample of the target subject is decreased compared to the normal control.

In the present invention, the method may comprise a step of predicting that the target individual has a high probability of developing an immune-related disease in a case where the expression level of more than one protein selected from the group consisting of CD25, TIGIT, LAG3, CTLA-4, GITR, OX40, ICOS, PD-1, TIM-3, CCR4, FR4, CD15s, PI-16 and Lrig-1 proteins, or where the expression level of the genes encoding such proteins is changed (increased or decreased) compared to the normal control.

In the present invention, the method may comprise a step of predicting that the target individual has a high probability of developing an immune-related disease in a case where the expression level of Lrig-1 protein or the gene encoding it is decreased compared to a normal control.

Furthermore, in the case of predicting or diagnosing that an immune-related disease is highly likely to occur by measuring the expression level of Lrig-1 protein or its extracellular domain or the gene encoding it, the method may further comprise a step of administering a drug for the disease to the individual.

According to one embodiment of the present invention, there is provided a binding molecule comprising a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

According to one embodiment of the present invention, there is provided a binding molecule comprising a heavy chain variable region comprising a heavy chain CDR1 encoded by the nucleotide sequence represented by SEQ ID NO: 13, a heavy chain CDR2 encoded by the nucleotide sequence represented by SEQ ID NO: 14, and a heavy chain CDR3 encoded by the nucleotide sequence represented by SEQ ID NO: 15, and a light chain variable region comprising a light chain CDR1 encoded by the nucleotide sequence represented by SEQ ID NO: 16, a light chain CDR2 encoded by the nucleotide sequence represented by SEQ ID NO: 17, and a light chain CDR3 encoded by the nucleotide sequence represented by SEQ ID NO: 18.

According to one embodiment of the present invention, there is provided a binding molecule comprising a heavy chain variable region consisting of the amino acid sequence represented by SEQ ID NO: 11, and a light chain variable region consisting of the amino acid sequence represented by SEQ ID NO: 12.

According to one embodiment of the present invention, there is provided a binding molecule comprising a heavy chain variable region encoded by the nucleotide sequence represented by SEQ ID NO: 19, and a light chain variable region encoded by the nucleotide sequence represented by SEQ ID NO: 20.

According to one embodiment of the present invention, there is provided a binding molecule that further comprises a fragment crystallization region (Fc region) or a constant region.

According to one embodiment of the present invention, there is provided a binding molecule wherein the Fc region is an Fc region of an IgA, IgD, IgE, IgM, IgG1, IgG2, IgG3 or IgG4, or a hybrid Fc.

According to one embodiment of the present invention, there is provided a binding molecule that further comprises a heavy chain constant region consisting of an amino acid sequence selected from the group consisting of SEQ ID NO: 21, 23, 24, 27, 28, 29, 30 and 32.

According to one embodiment of the present invention, there is provided a binding molecule that further comprises a light chain constant region consisting of an amino acid sequence selected from the group consisting of SEQ ID NO: 22, 25, 26, and 31.

According to one embodiment of the present invention, there is provided a binding molecule that further comprises a heavy chain constant region encoded by the nucleotide sequence represented by SEQ ID NO: 33 or 35, and a light chain constant region encoded by the nucleotide sequence represented by SEQ ID NO: 34 or 36.

According to one embodiment of the present invention, there is provided a binding molecule that comprises a heavy chain consisting of the amino acid sequence represented by SEQ ID NO: 37 or 38, and a light chain consisting of the amino acid sequence represented by SEQ ID NO: 39 or 40.

According to one embodiment of the present invention, there is provided a binding molecule that comprises a heavy chain consisting of the amino acid sequence represented by SEQ ID NO: 37, and a light chain consisting of the amino acid sequence represented by SEQ ID NO: 39.

According to one embodiment of the present invention, there is provided a binding molecule that comprises a heavy chain consisting of the amino acid sequence represented by SEQ ID NO: 38 and a light chain consisting of the amino acid sequence represented by SEQ ID NO: 40.

According to one embodiment of the present invention, there is provided a binding molecule that comprises a heavy chain encoded by the nucleotide sequence represented by SEQ ID NO: 41 or 43, and a light chain encoded by the nucleotide sequence represented by SEQ ID NO: 42 or 44.

According to one embodiment of the present invention, there is provided a binding molecule that comprises a heavy chain encoded by the nucleotide sequence represented by SEQ ID NO: 41, and a light chain encoded by the nucleotide sequence represented by SEQ ID NO: 42.

According to one embodiment of the present invention, there is provided a binding molecule that comprises a heavy chain encoded by the nucleotide sequence represented by SEQ ID NO: 43 and a light chain encoded by the nucleotide sequence represented by SEQ ID NO: 44.

According to one embodiment of the present invention, the binding molecule provides a binding molecule that is an antibody or a fragment thereof.

According to one embodiment of the present invention, there is provided a binding fragment wherein the antibody is a chimeric antibody, a humanized antibody, a bivalent, bispecific molecule, a minibody, a domain antibody, a bispecific antibody, an antibody mimic, an unibody, a diabody, a triabody, a tetrabody, or fragments thereof.

According to one embodiment of the present invention, a nucleic acid molecule encoding the binding molecule is provided.

According to one embodiment of the present invention, an expression vector into which the nucleic acid molecule is inserted is provided.

According to one embodiment of the present invention, a host cell line transfected with the expression vector is provided.

According to one embodiment of the present invention, there is provided an antibody-drug conjugate (ADC) that comprises an antibody that comprises a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10, and a drug.

According to one embodiment of the present invention, there is provided a pharmaceutical composition for preventing or treating a brain and nervous system disease comprising the binding molecule of the present invention as an active ingredient.

According to one embodiment of the present invention, there is provided a pharmaceutical composition wherein the brain and nervous system disease is a neurodegenerative disease or a neuroinflammatory disease.

According to one embodiment of the present invention, there is provided a pharmaceutical composition wherein the neurodegenerative disease or neuroinflammatory disease is at least one selected from the group consisting of stroke, dementia, Alzheimer's disease, Parkinson's disease, Huntington's disease, Niemann-Pick disease, multiple sclerosis, prion disease, Creutzfeldt-Jakob disease, frontotemporal dementia, dementia with Lewy bodies, amyotrophic lateral sclerosis, paraneoplastic syndrome, cortical degeneration syndrome, multiple system atrophy, progressive supranuclear palsy, nervous system autoimmune disease, spinocerebellar ataxia, inflammatory and neuropathic pain, cerebrovascular disease, spinal cord injury, and tauopathy.

According to one embodiment of the present invention, in a chimeric antigen receptor (CAR) comprising an antigen-specific binding domain, a linking domain and a CD3 zeta (2) signaling domain, there is provided a chimeric antigen receptor wherein the specific binding domain is a heavy chain variable region comprising a heavy chain CDRI consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

According to one embodiment of the present invention, there is provided a pharmaceutical composition for preventing or treating a brain and nervous system disease comprising the chimeric antigen receptor as an active ingredient.

According to one embodiment of the present invention, there is provided a diagnostic composition for a brain and nervous system disease comprising the binding molecule of the present invention.

According to one embodiment of the present invention, there is provided a diagnostic composition for a brain and nervous system disease comprising the composition of the present invention.

According to one embodiment of the present invention, there is provided a method for providing information for diagnosing a brain and nervous system disease comprising the step of measuring the expression level of Lrig-1 protein on the surface of T cells in a biological sample isolated from a target subject using the binding molecule of the present invention.

According to another embodiment of the present invention, there is provided a method for preventing or treating a brain and nervous system disease characterized by a binding molecule comprising a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

According to one embodiment of the present invention, the binding molecule is an antibody or a fragment thereof, and there is provided a method for preventing or treating a brain and nervous system disease wherein the antibody is characteristically a chimeric antibody, a humanized antibody, a bivalent, a bispecific molecule, a minibody, a domain antibody, a bispecific antibody, an antibody mimic, an unibody, a diabody, a triabody, a tetrabody, or fragments thereof.

According to another embodiment of the present invention, there is provided a method for preventing or treating a brain and nervous system disease characterized by an antibody-drug conjugate comprising an antibody that comprises a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10, and a drug.

According to one embodiment of the present invention, in a chimeric antigen receptor (CAR) comprising an antigen-specific binding domain, a linking domain and a CD3 zeta (5) signaling domain, there is provided a method for preventing or treating a brain and nervous system disease characterized by a chimera antigen receptor, wherein the specific binding domain is a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

Advantageous Effects of Invention

The binding molecule provided in the present invention can specifically prevent, ameliorate, or treat brain and nervous system diseases such as various neurodegenerative or neuroinflammatory diseases.

BEST DESCRIPTION FOR IMPLEMENTING THE INVENTION

According to one embodiment of the present invention, there is provided a binding molecule comprising a heavy chain variable region comprising a heavy chain CDR1 consisting of the amino acid sequence represented by SEQ ID NO: 5, a heavy chain CDR2 consisting of the amino acid sequence represented by SEQ ID NO: 6, and a heavy chain CDR3 consisting of the amino acid sequence represented by SEQ ID NO: 7, and a light chain variable region comprising a light chain CDR1 consisting of the amino acid sequence represented by SEQ ID NO: 8, a light chain CDR2 consisting of the amino acid sequence represented by SEQ ID NO: 9, and a light chain CDR3 consisting of the amino acid sequence represented by SEQ ID NO: 10.

DETAILED DESCRIPTION OF INVENTION

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

[Preparation Example] T Cell Subset Cell Culture

In order to identify whether the Lrig-1 protein is expressed only in regulatory T cells (Treg), the subsets of T cells, Th0, Th1, Th2, Th17, and iTreg, were prepared. The iTreg refers to cells whose differentiation has been artificially induced in a medium containing the following composition, unlike nTreg which has been naturally isolated.

The subsets of the T cells were induced to differentiate into respective cells by first isolating naive T cells obtained from the spleen of mice, causing RPMI1640 (Invitrogen Gibco, Grand Island, NY) nutrient medium that contains 10% fetal bovine serum (FBS; HyClone, Logan, UT) to further contain the respective ingredients of Table 1 below, and performing 72-hour incubation in an incubator at 37° C., 5% $CO_2$.

TABLE 1

| Differentiated cell | Composition |
|---|---|
| Th0 | anti-CD3, anti-CD28 |
| Th1 | IL-12, anti-IL-4 antibody |
| Th2 | IL-4, anti-IFNβ |
| Th17 | IL-6, TGFβ, anti-IFNβ, anti-IL-4 |
| iTreg | IL-2, TGFβ |

[Example 1] Structural Analysis of Lrig-1

A three-dimensional steric structure of the extracellular domain of the Lrig-1 protein was predicted to produce antibodies specific for the Lrig-1 protein, a surface protein of regulatory T cells.

First, in order to predict base sequences of epitopes (epitopes), tools of Uniprot (http://www.uniprot.org) and RCSB Protein Data Bank (http://www.rcsb.org/pdb) were used to predict a three-dimensional steric structure of the extracellular domain (ECD) of the Lrig-1 protein so that the structure of ECD is identified. Then, the results are illustrated in FIGS. 1 and 2.

Figure 1:
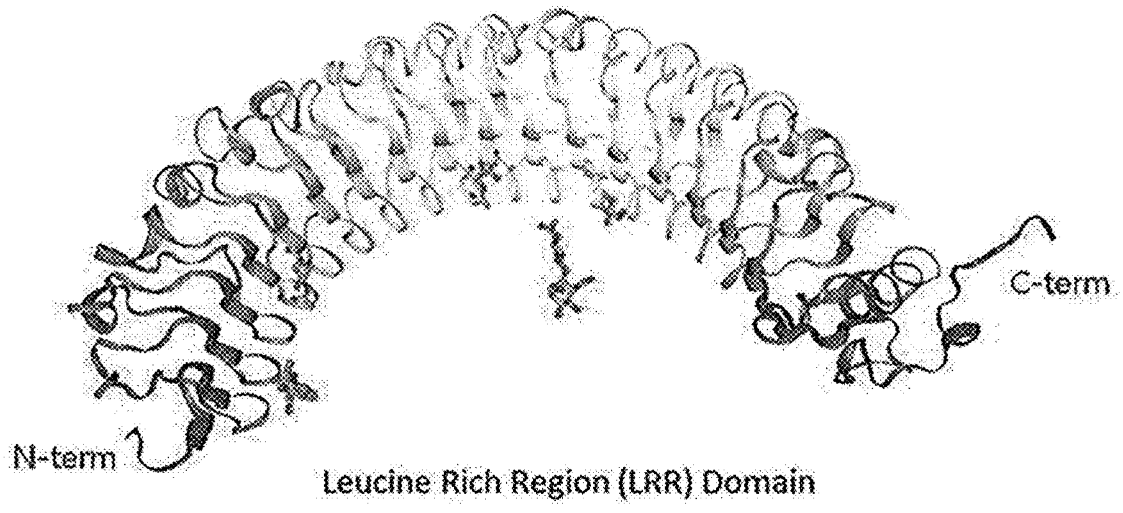
FIG. 1 illustrates a structure of the Lrig-1 protein according to an embodiment of the present invention.

As illustrated in FIG. 1, a total of 15 leucine-rich regions of LRR1 to LRR15 existed in the Lrig-LRR domain (amino acid sequence at positions 41 to 494) in the extracellular domain of the Lrig-1 protein. Each of the LRR domains is composed of 23 to 27 amino acids, with 3 to 5 leucine being present.

Figure 2:
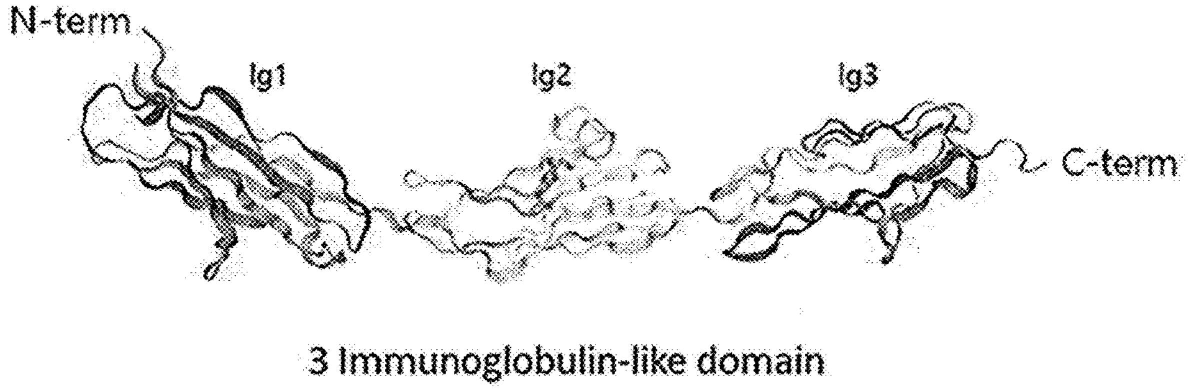
FIG. 2 illustrates a structure of the Lrig-1 protein according to an embodiment of the present invention.

In addition, as illustrated in FIG. 2, three immunoglobulin-like domains exist in amino acid sequences at positions 494 to 781 of the Lrig-1 protein in the extracellular domain of the Lrig-1 protein.

[Example 2] Prediction of Lrig-1 Epitope Amino Acid Sequence

Prediction of the above base sequence was performed using Ellipro server (http://tools.iedb.org/ellipro/) which is an epitope prediction software based on a structure of the Lrig-1 protein. The Ellipro search engine was used because it corresponds to a search engine known to be the most reliable among the existing algorithms for predicting an epitope.

The extracellular domain analyzed in Example 1 was entered into the epitope prediction software, and a total of 22 contiguous epitope amino acid sequences were predicted, and a total of 8 discontinuous epitope amino acid sequences were predicted.

[Production Examples 1 and 2] Production of Monoclonal Antibodies Specific to Lrig-1 Protein Antibodies specific for the Lrig-1 protein according to the present invention were produced. The present antibodies were not produced by specifying a certain epitope, but were produced as antibodies capable of binding to any site on the Lrig-1 protein.

In order to produce the antibodies, cells expressing the Lrig-1 protein were produced. More specifically, a DNA fragment corresponding to SEQ ID NO: 2 and pcDNA (hygro) were cleaved with a cleavage enzyme, incubated at 37° C., and ligated to produce pcDNA into which a DNA sequence of the Lrig-1 protein is inserted. The thus produced pcDNA into which SEQ ID NO: 2 is inserted was introduced, through transfection, into T cells, so that the Lrig-1 protein is allowed to be expressed on the surface of the T cells.

Light and heavy chain amino acid sequences capable of binding to Lrig-1 expressed on the cell surface were selected from the Human scFv library.

The selected heavy and light chain amino acid sequences were fused with the heavy chain constant region represented by SEQ ID NO: 24 or 30 and the light chain constant region represented by SEQ ID NO: 26 or 31, respectively, to produce monoclonal antibodies. The sequences of the monoclonal antibodies are shown in Table 2 below.

TABLE 2

| Classification | Clone | Location | Amino acid sequence | Sequence information |
|---|---|---|---|---|
| Production Example 1 | GTC310-01 mouse antibody | Heavy chain | EVQLLESGGGLVQPGGSLRLSCAASG FTFS NYAMS WVRQAPGKGLEWVS VISHGGGSTYYADSVKG RFTISRDNSKNTLYLQMNSLRAEDTA VYYCAR VISNCHLGVCYYSNGMDV WGQGTLVTVSSAKTTAPSVYPLAPVC GDTTGSSVTLGCLVKGYFPEPVTLTW NSGSLSSGVHTFPAVLQSDLYTLSSSV TVTSSTWPSQSITCNVAHPASSTKVD KKIEPRGPTIKPCPPCKCPAPNLLGGPS VFIFPPKIKDVLMISLSPIVTCVVVDVS EDDPDVQISWFVNNVEVHTAQTQTH REDYNSTLRVVSALPIQHQDWMSGK EFKCKVNNKDLPAPIERTISKPKGSVR APQVYVLPPPEEEMTKKQVTLTCMV TDFMPEDIYVEWTNNGKTELNYKNT EPVLDSDGSYFMYSKLRVEKKNWVE RNSYSCSVVHEGLHNHHTTKSFSRTP GK | SEQ ID NO: 37 |
| | | Light chain | QLVLTQPPSVSAAPGQRVSISC SGSSSNIGDNYVS WYQQVPGSAPKLLIY DNNKRPS GIPDRFSASKSGTSATLGITGLQTGDE ADYYCAT WDGSLSAGRV FGGGTKLTVL RADAAPTVSIFPPSSEQLTSGGASVVC FLNNFYPKDINVKWKIDGSERQNGVL NSWTDQDSKDSTYSMSSTLTLTKDEY ERHNSYTCEATHKTSTSPIVKSFNRNE C | SEQ ID NO: 39 |
| Production Example 2 | GTC310-01 humanized antibody | Heavy chain | EVQLLESGGGLVQPGGSLRLSCAASG FTFS NYAMS WVRQAPGKGLEWVS VISHGGGSTYYADSVKG RFTISRDNSKNTLYLQMNSLRAEDTA VYYCAR VISNCHLGVCYYSNGMDV WGQGTLVTVSSASTKGPSVFPLAPSS KSTSGGTAALGCLVKDYFPEPVTVSW | SEQ ID NO: 38 |

TABLE 2-continued

| Classification | Clone | Location | Amino acid sequence | Sequence information |
|---|---|---|---|---|
| | | | NSGALTSGVHTFPAVLQSSGLYSLSSV VTVPSSSLGTQTYICNVNHKPSNTKV DKKVEPKSCDKTHTCPPCPAPELLGG PSVFLFPPKPKDTLMISRTPEVTCVVV DVSHEDPEVKFNWYVDGVEVHNAKT KPREEQYNSTYRVVSVLTVLHQDWL NGKEYKCKVSNKALPAPIEKTISKAK GQPREPQVYTLPPSREEMTKNQVSLT CLVKGFYPSDIAVEWESNGQPENNYK TTPPVLDSDGSFFLYSKLTVDKSRWQ QGNVFSCSVMHEALHNHYTQKSLSLS PGK | |
| | | Light chain | QLVLTQPPSVSAAPGQRVSISC SGSSSNIGDNYVS WYQQVPGSAPKLLIY DNNKRPS GIPDRFSASKSGTSATLGITGLQTGDE ADYYCAT WDGSLSAGRV FGGGTKLTVL RTVAAPSVFIFPPSDEQLKSGTASVVC LLNNFYPREAKVQWKVDNALQSGNS QESVTEQDSKDSTYSLSSTLTLSKADY EKHKVYACEVTHQGLSSPVTKSFNRG EC | SEQ ID NO: 40 |

[Example 3] Identification of Specific Expression of Lrig-1 mRNA in Regulatory T Cells Verification was made of whether the Lrig-1 protein can act as a biomarker specific for regulatory T cells.

For the verification, $CD4^+$ T cells were isolated using magnet-activated cell sorting (MACS), through CD4 beads, from the spleen of mice. Subsequently, regulatory T ($CD4^+CD25^+T$) cells and non-regulatory T ($CD4^+CD25^-$ T) cells were isolated with a fluorescence-activated cell sorter (FACS) using a CD25 antibody. For the respective cells and the cells differentiated in Preparation Example 1, mRNA was extracted using Trizol, and gDNA was removed from genomic RNA using gDNA extraction kit (Qiagen) according to the protocol provided by the manufacturer. The gDNA-removed mRNA was synthesized into cDNA through the BDsprint cDNA Synthesis Kit (Clonetech).

Real-time polymerase chain reaction (RT PCR) was performed to quantitatively identify an expression level of Lrig-1 mRNA in the cDNA.

The real-time polymerase chain reaction was performed with primers shown in Table 3 below using SYBR Green (Molecular Probes) by the protocol provided by the manufacturer under conditions of 40 cycles consisting of 95° C. for 3 minutes, 61° C. for 15 seconds, 72° C. for 30 seconds, a relative gene expression level was calculated using the ΔCT method, and normalized using HPRT. The results are illustrated in FIGS. 3 to 6.

TABLE 3

| Primer | Sequence | Sequence Information |
|---|---|---|
| Mouse Lrig-1 | Forward 5'-GAC GGA ATT CAG TGA GGA GAA CCT-3' | SEQ ID NO: 45 |
| | Reverse 5'-CAA CTG GTA GTG GCA GCT TGT AGG-3' | SEQ ID NO: 49 |
| Mouse Lrig-2 | forward 5'-TCA CAA GGA ACA TTG TCT GAA CCA-3' | SEQ ID NO: 47 |
| | reverse 5'-GCC TGA TCT AAC ACA TCC TCC TCA-3' | SEQ ID NO: 48 |
| Mouse Lrig-3 | forward 5'-CAG CAC CTT GAG CTG AAC AGA AAC-3' | SEQ ID NO: 49 |
| | reverse 5'-CCA GCC TTT GGT AAT CTC GGT TAG-3' | SEQ ID NO: 50 |
| Mouse FOXP3 | forward 5'-CTT TCA CCT ATC CCA CCC TTA TCC-3' | SEQ ID NO: 51 |
| | reverse 5'-ATT CAT CTA CGG TCC ACA CTG CTC-3' | SEQ ID NO: 52 |
| ACTG1 | forward 5'-GGC GTC ATG GTG GGC ATG GG-3' | SEQ ID NO: 43 |
| | reverse 5'-ATG GCG TGG GGA AGG GCG TA-3' | SEQ ID NO: 54 |

Figure 3:
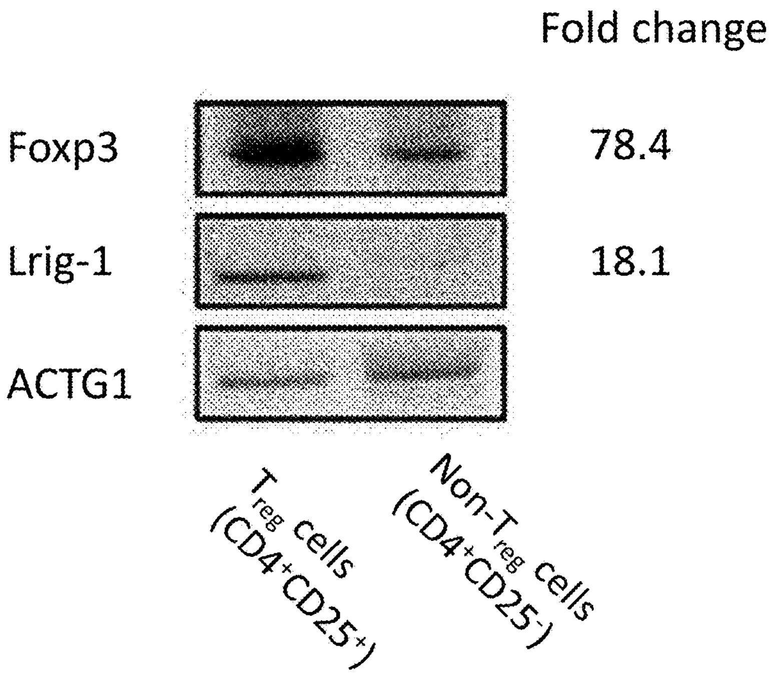
FIG. 3 illustrates an expression level of Lrig-1 mRNA according to an embodiment of the present invention.
Figure 4:
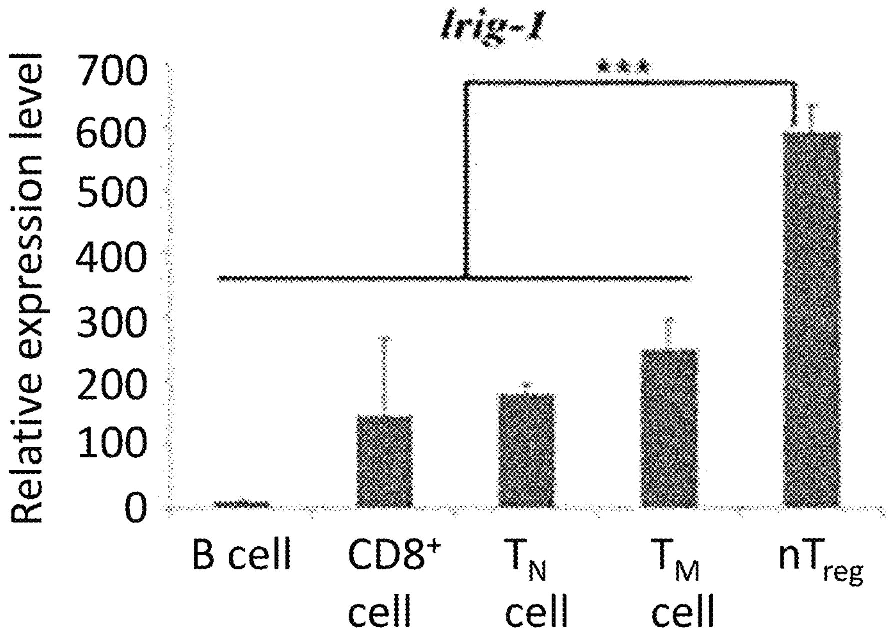
FIG. 4 illustrates an expression level of Lrig-1 mRNA according to an embodiment of the present invention.
Figure 5:
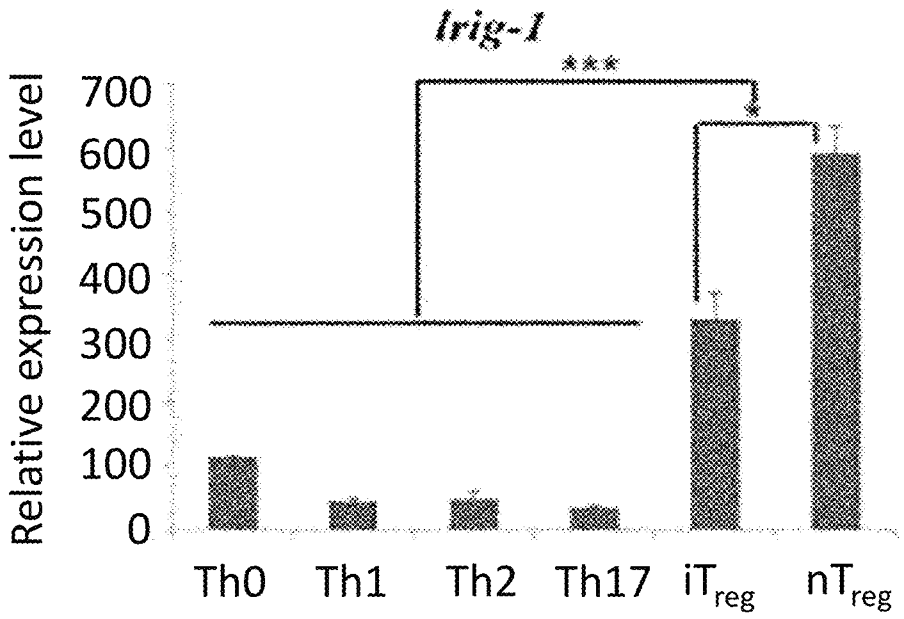
FIG. 5 illustrates an expression level of Lrig-1 mRNA according to an embodiment of the present invention.
Figure 6:
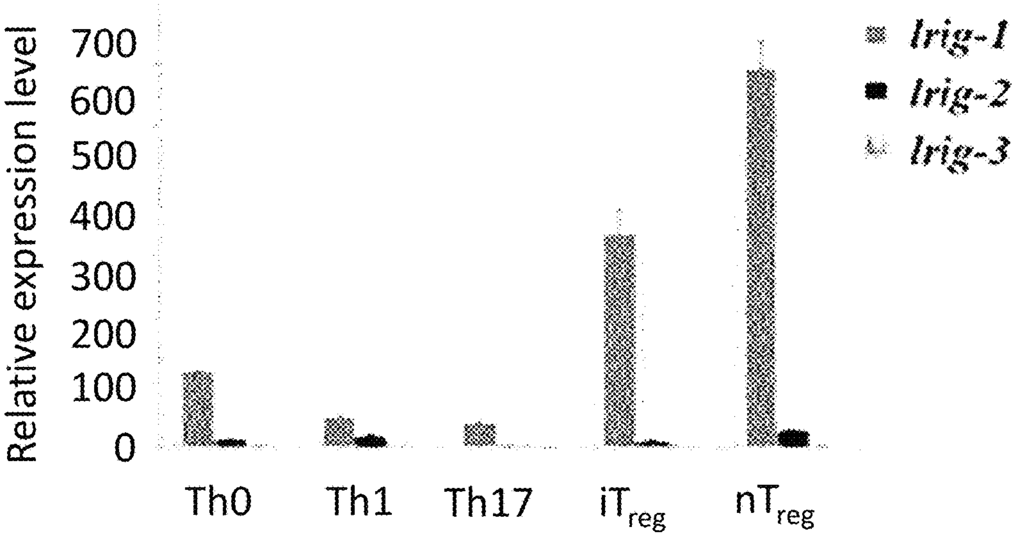
FIG. 6 illustrates expression levels of Lrig-1, Lrig-2, and Lrig-3 mRNAs according to an embodiment of the present invention.

As illustrated in FIG. 3, it can be seen that the expression of Lrig-1 in regulatory T ($CD4^+CD25^+T$) cells is 18.1 times higher than non-regulatory T ($CD4^+CD25^-T$) cells. This was about 10 times higher expression level than Lag3 and Ikzf4, which are previously known markers for regulatory T cells. In addition, as illustrated in FIGS. 4 and 5, the expression of Lrig-1 mRNA was remarkably high in regulatory T cells as compared with other types of immune cells, and in particular, was remarkably high in naturally isolated regulatory T cells (nTreg) as compared with induced regulatory T cells (iTreg cells). In addition, as illustrated in FIG. 6, expression of Lrig-1 was the highest among Lrig-1, Lrig-2, and Lrig-3 which correspond to the Lrig family.

From the above results, it can be seen that the Lrig-1 protein according to the present invention is specifically expressed in regulatory T cells, in particular, naturally-occurring regulatory T cells.

[Example 4] Identification of Specific Expression of Lrig-1 Protein in Regulatory T Cells It was identified whether the Lrig-1 protein expressed from Lrig-1 mRNA is specifically expressed only in regulatory T cells.

Using FOXP3-RFP-knocked-in mice, the FOXP3-RFP obtained by coupling red fluorescence protein (RFP) to FOXP3 promoter, a transcription factor specific for regulatory T cells, $CD4^+$ T cells were isolated using magnet-activated cell sorting (MACS), through CD4 beads, from the spleen of the mice. Subsequently, using RFP protein, regulatory T ($CD4^+RFP^+T$) cells and non-regulatory T ($CD4^+ RFP^-T$) cells were obtained by performing isolation through a fluorescence-activated cell sorter (FACS). The respective cells were stained with the purchased Lrig-1 antibody and a negative control was stained with an isotype-matched control antibody, to measure an expression level of Lrig-1 with the fluorescence-activated cell sorter. The results are illustrated in FIG. 7.

Figure 7:
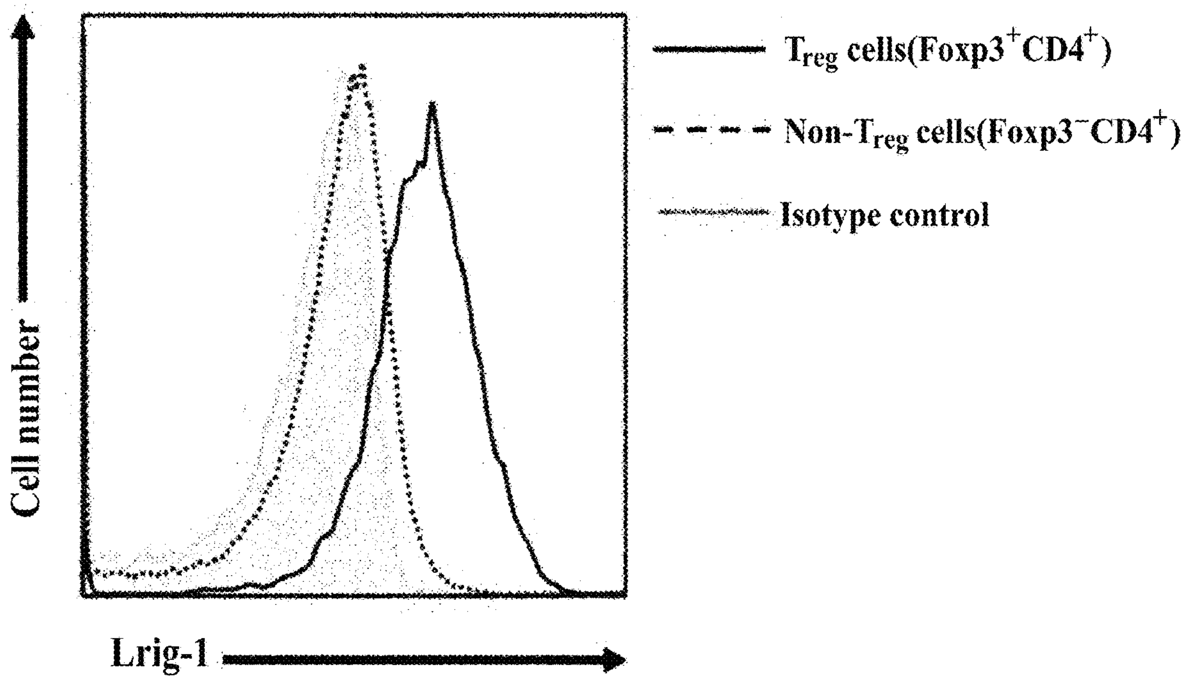
FIG. 7 illustrates results obtained by comparing expression levels of Lrig-1 protein in regulatory T cells and non-regulated T cells according to an embodiment of the present invention.

As illustrated in FIG. 7, the non-regulatory T cells indicated by a dotted line showed almost the same expression level of Lrig-1 as the negative control, whereas there were a large number of cells with high expression level of Lrig-1 in the regulatory T cells.

From the above results, it can be seen that the Lrig-1 protein according to the present invention is specifically expressed in regulatory T cells.

[Example 5] Identification of Specific Expression of Lrig-1 Protein on Surface of Regulatory T Cells From the viewpoint that in order to be a target of cell therapy, the Lrig-1 protein must be expressed on the surface of regulatory T cells, which in turn allows a more effective target therapy, it was identified whether the Lrig-1 protein is expressed on the surface of the regulatory T cells.

The respective differentiated T cell subsets of Preparation Example 1 were stained with anti-CD4-APC and anti-Lrig-1-PE antibodies, and expression levels of Lrig-1 were measured at the respective cell surfaces using a fluorescence-activated cell sorter (FACS). The results are illustrated in FIG. 8.

Figure 8:
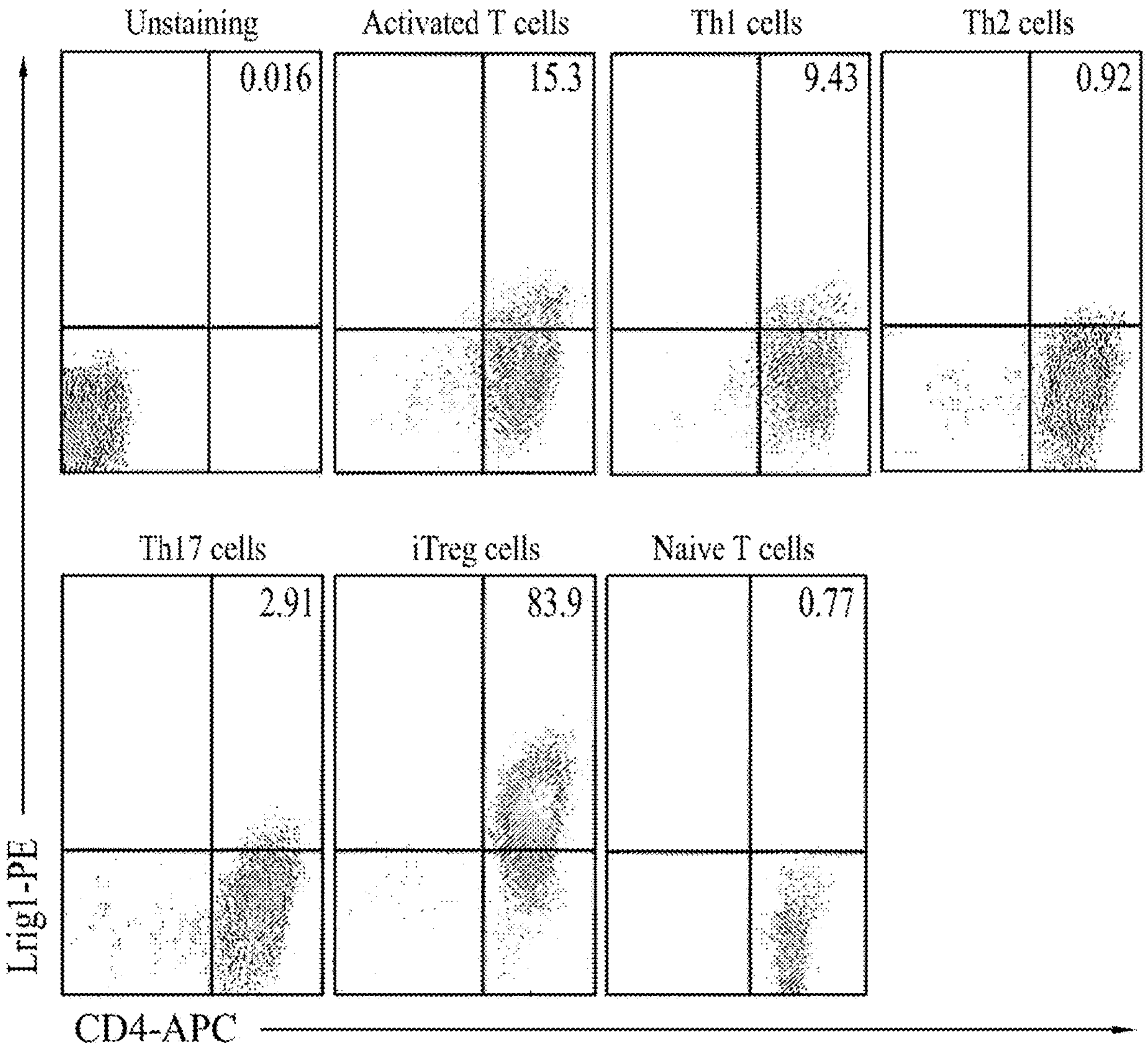
FIG. 8 illustrates expression level of the Lrig-1 protein on the surface of regulatory T cells according to an embodiment of the present invention.

As illustrated in FIG. 8, Lrig-1 was expressed in an amount of 0.77 to 15.3 in activated T cells, Th1 cells, Th2 cells, Th17 cells, and naive T cells, whereas Lrig-1 was expressed as high as 83.9 in differentiation-induced T cells (iTreg cells).

From the above results, it can be seen that the Lrig-1 protein according to the present invention is not only specifically expressed in regulatory T (Treg) cells, but also is, in particular, expressed at a higher level on the surface of the Treg cells.

Figure 9:
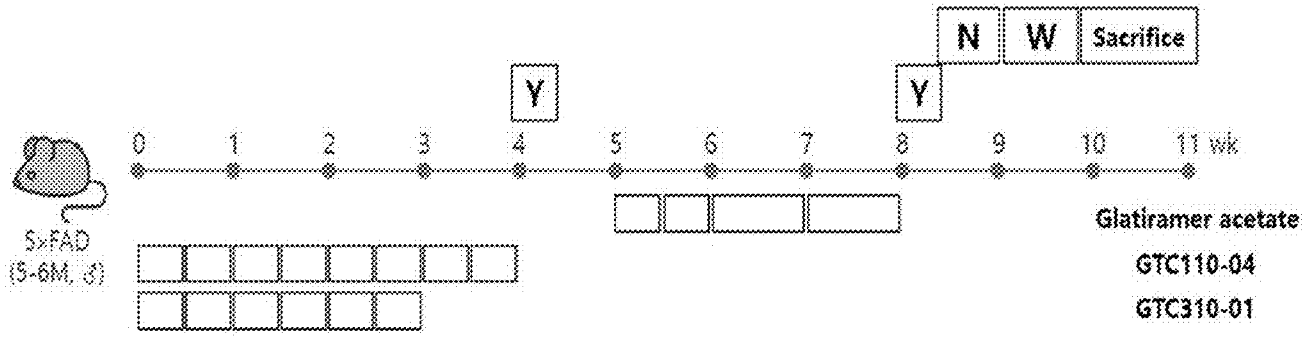
FIG. 9 illustrates an experimental design for identifying therapeutic effects of monoclonal antibodies on Alzheimer's, according to an embodiment of the present invention.

[Example 6] Evaluation of Therapeutic Ability of Antibody According to Present Invention Against Alzheimer's Disease-5×FAD Mice In order to evaluate the therapeutic ability of the antibody according to the present invention against Alzheimer's disease, groups were designed as shown in FIG. 9. Specifically, 5- to 6-month-old male 5×FAD mice with induced Alzheimer's disease were intravenously injected with GTC310-01 mouse antibody at an amount of 10 mpk each for 3 weeks. However, glatiramer acetate (GA, Copaxone®) was subcutaneously injected at an amount of 100 μg for 3 weeks, or the H6 antibody (GTC110-04) shown in Table 4 was intravenously injected in an amount of 10 mpk for 4 weeks as a positive control.

TABLE 4

| Clone | Location | Amino Acid Sequence |
|---|---|---|
| H6 antibody (GTC110-04) | Heavy chain | EVQLLESGGGLVQPGGSLRLSCAASGFTFSNYAMSWVRQAPGKG LEWVSVISHGGGSTYYADSVKGRFTISRDNSKNTLYLQMNSLRA EDTAVYYCARVISNCHLGVCYYSNGMDVWGQGTLVTVSSTTAPS VYPLAPVCGDTTGSSVTLGCLVKGYFPEPVTLTWNSGSLSSGVH TFPAVLQSDLYTLSSSVTVTSSTWPSQSITCNVAHPASSTKVDK KIEPRGPTIKPCPPCKCPAPNLLGGPSVFIFPPKIKDVLMISLS PIVTCVVVDVSEDDPDVQISWFVNNVEVHTAQTQTHREDYNSTL RVVSALPIQHQDWMSGKEFKCKVNNKDLPAPIERTISKPKGSVR APQVYVLPPPEEEMTKKQVTLTCMVTDFMPEDIYVEWTNNGKTE LNYKNTEPVLDSDGSYFMYSKLRVEKKNWVERNSYSCSVVHEGL HNHHTTKSFSRTPGK (SEQ ID NO: 55) |
| | Light chain | QSVLTQPPSASGTPGQRVTISCSGSSSNIGNNDVYWYQQLPGTA PKLLIYSDSQRPSGVPDRFSGSKSGTSASLAISGLRSEDEADYY CGTWDYSLSGYVFGGGTKLTVLRTVAAPTVSIFPPSSEQLTSGG ASVVCFLNNFYPKDINVKWKIDGSERQNGVLNSWTDQDSKDSTY SMSSTLTLTKDEYERHNSYTCEATHKTSTSPIVKSFNRNEC (SEQ ID NO: 56) |

1. Amyloid-β Plaque Reducing Effect

Figure 10:
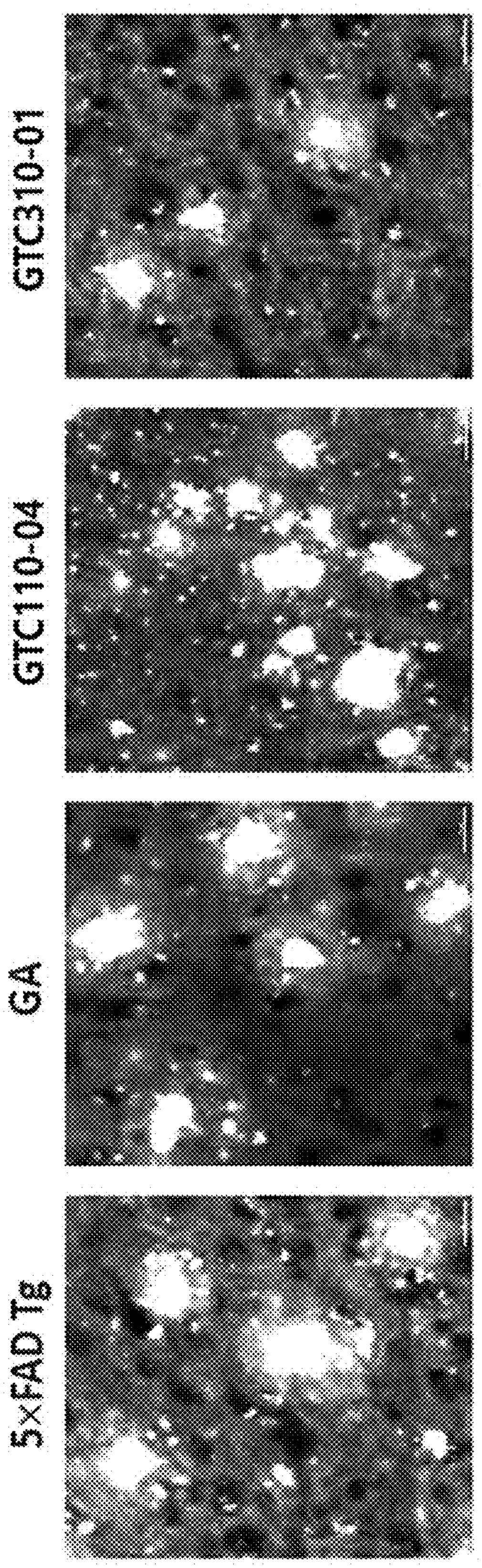
FIG. 10 illustrates a photograph of results obtained with a fluorescence microscope by staining the brain cortex and hippocampal tissue of the mouse with Thioflavin S (ThS) obtained after each treatment of Alzheimer's-induced mice with the monoclonal antibody according to an embodiment of the present invention.

For immunohistological analysis, the above-treated mice were euthanized, and the cortex and hippocampus tissues were obtained and fixed in 4% paraformaldehyde (pH 7.4) for 16 hours. The fixed cortex and hippocampus tissues were immersed in 30% sucrose for cryoprotection and sliced to a thickness of 35 μm. To visualize Aβ plauqes, the sliced brain sections were stained with thioflavin S (ThS) for 7 minutes. Thioflavin S was purchased from Sigma-Aldrich (catalog number T-1892). Thioflavin S (ThS) at 500 μM was dissolved in 50% ethanol. After successive washes with 100%, 95% and 70% ethanol, the sections were transferred to PBS. Relatively thick free-floating brain slices were incubated with goat anti-GFAP antibody for 7 days at 4° C. for immunofluorescence. Then, the sections were incubated overnight at 4° C. with Alexa Fluor 594-conjugated donkey anti-goat IgG (1:200, Abcam, ab150132). Nuclear counterstaining was performed using 4'6'-damiino-2-phenylindole dihydrochloride hydrate (DAPI, 1 mg/mL, 1:2000, Sigma). Images were taken with a Leica DM2500 fluorescence microscope, and the results are shown in FIG. 10. Additionally, the ThS+ area ratio (%) relative to normal mice was calculated using the ImageJ software program, and the results are shown in FIG. 11.

Figure 11:
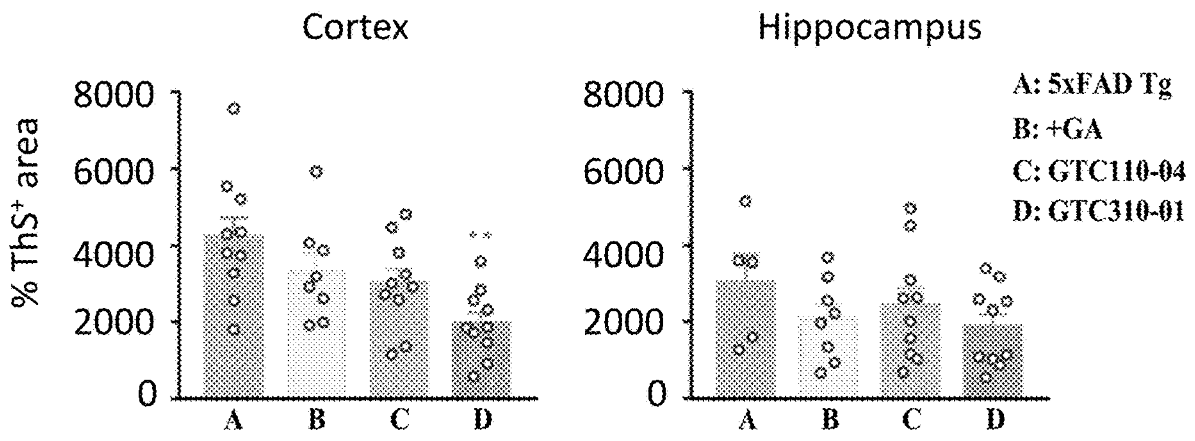
FIG. 11 illustrates a graph showing the results of calculating the ThS+ area ratio (%) relative to normal mice after staining the brain cortex and hippocampal tissue of the mouse with Thioflavin S (ThS) obtained after each treatment of Alzheimer's-induced mice with the monoclonal antibody according to an embodiment of the present invention.

As shown in FIGS. 10 and 11, although the ThS+ area significantly increased in Alzheimer's-induced mice, when the GTC310-01 antibody according to the present invention was administered, the ThS+ area was significantly reduced, especially in the cortex, thus showing that the effect of reducing amyloid-β plaques was excellent.

2. Y-Maze Test

For the Y-maze test, a Y-shaped maze was used which had three identical arms having a length of 40 cm (with a 15-cm high wall) at an angle of 120 degrees from each other. This experiment was a behavioral experiment using the rodent's instinctive exploring habit and was based on the fact that there is a high possibility of exploring a new area. The higher the degree that the test animal remembered the arm it had just explored and tried not to enter the same arm, the higher the animal's memory level. An exploring time of 8 minutes was given to each individual, and the final results were expressed as spontaneous alteration (%) values in FIG. 12. The spontaneous alteration (%) value was calculated by Expression 1. Here, behavioral patterns were analyzed using SMART VIDEO TRACKING Software (Panlab, USA).

$$\text{Spontaneous alteration}(\%) = \frac{\text{number of triplet}}{\text{total arm entry} - 2} \quad \text{[Equation 1]}$$

Figure 12:
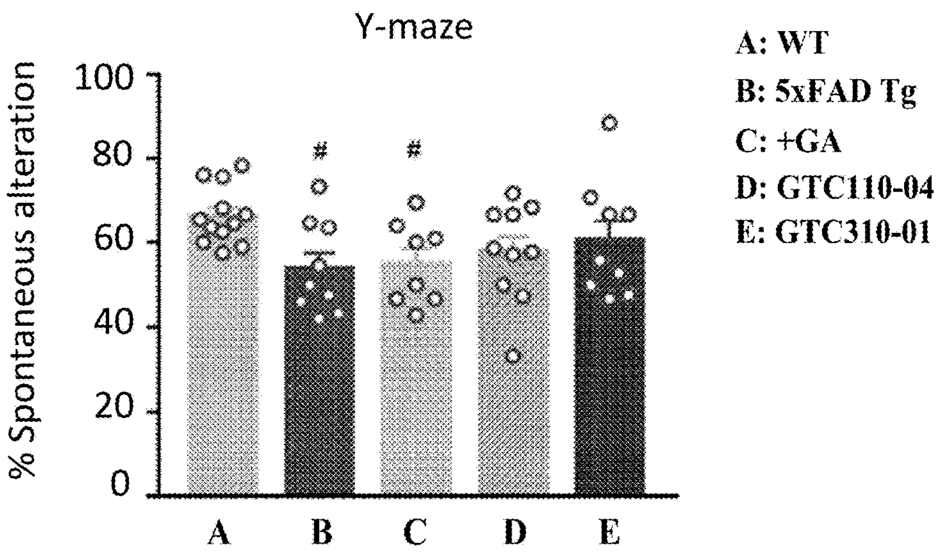
FIG. 12 illustrates a graph showing changes in spontaneous alternation (%) values as a result of Y-maze test after each treatment of Alzheimer's-induced mice with the monoclonal antibody according to an embodiment of the present invention.

As shown in FIG. 12, in this experiment for measuring the relative frequency at which the test animal perceives the surrounding clues and sequentially enters the maze, it was found that in the case where the mice with induced Alzheimer's disease were administered with the GTC310-01 antibody according to the present invention, the mice had a spontaneous alteration value at a level similar to that of a normal control.

3. Novel Object Recognition

The novel object recognition test was performed to evaluate memory using two different objects in a 40 cm×40 cm acrylic cage. After causing the test animal to acclimatize to the inside of the acrylic cage, two objects were placed at certain locations and the animal was allowed to perceive the objects freely. Then, the time for exploring each object was measured. 24-hour delay was given to each individual, and only one object was changed to another at the same location. Here, in a case where the animal perceives the changed object as a novel object and spends a longer exploring time, it may be determined that the animal has better memory. In a case where the animal does not remember the objects that it explored 24 hours before, the animal fails to distinguish between the novel object and the old object, and thus there is a possibility that the animal explores equally both objects. The animal was allowed to explore freely for a total of 10 minutes, and the result was expressed as a preference index (which equals novel object exploring time/total exploring time) in FIG. 13. Here, the analysis was performed using SMART VIDEO TRACKING Software (Panlab, USA).

Figure 13:
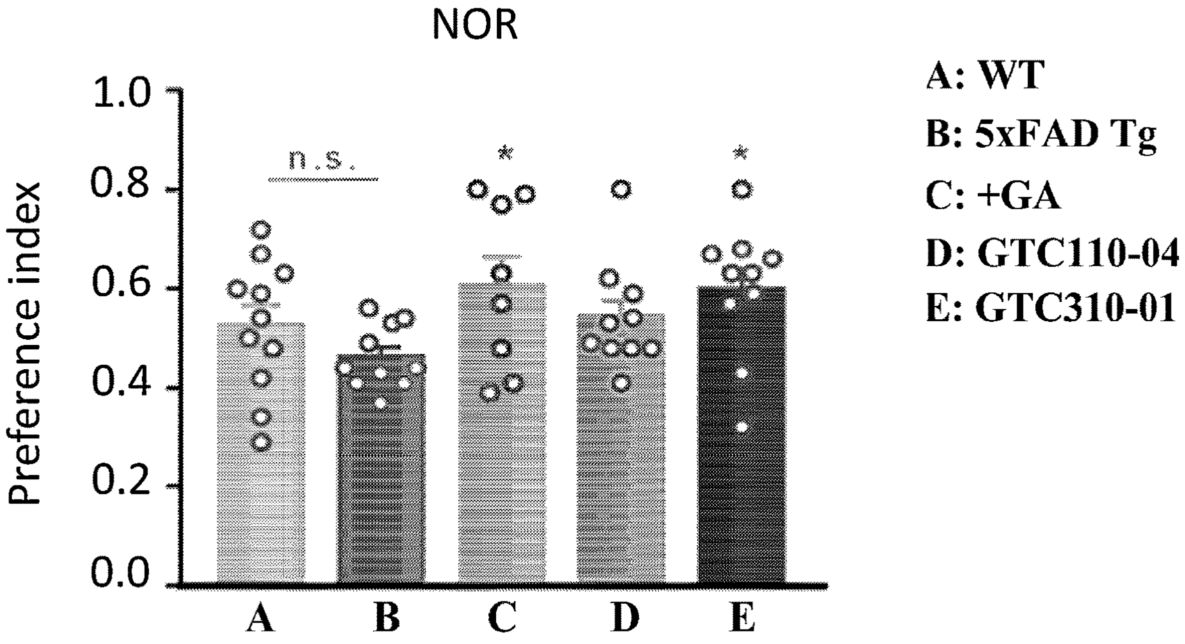
FIG. 13 illustrates a graph showing changes in preference values as a result of a novel object recognition experiment after each treatment of Alzheimer's-induced mice with the monoclonal antibody according to an embodiment of the present invention.

As shown in FIG. 13, the preference index for a new object was lower in the mice with induced Alzheimer's disease compared with the normal control. However, when the GTC310-01 antibody according to the present invention was administered, the preference value was higher than that of the normal control.

4. Water Maze Test

Figure 14:
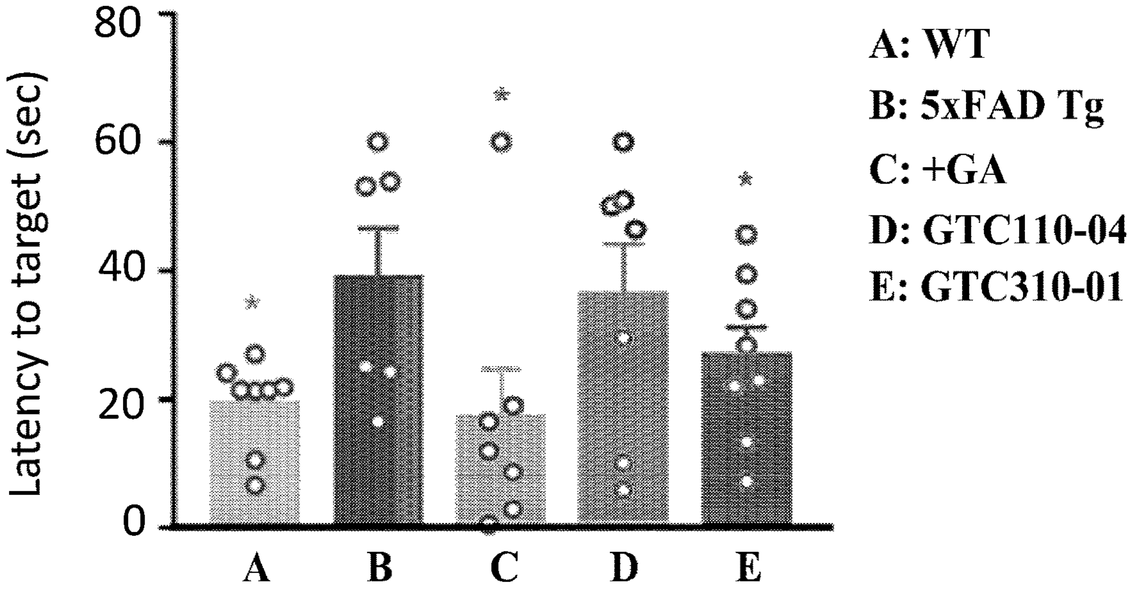
FIG. 14 illustrates a graph showing changes in the time taken to reach the position of the platform as a result of the water maze experiment after each treatment of Alzheimer's-induced mice with the monoclonal antibody according to an embodiment of the present invention.
Figure 15:
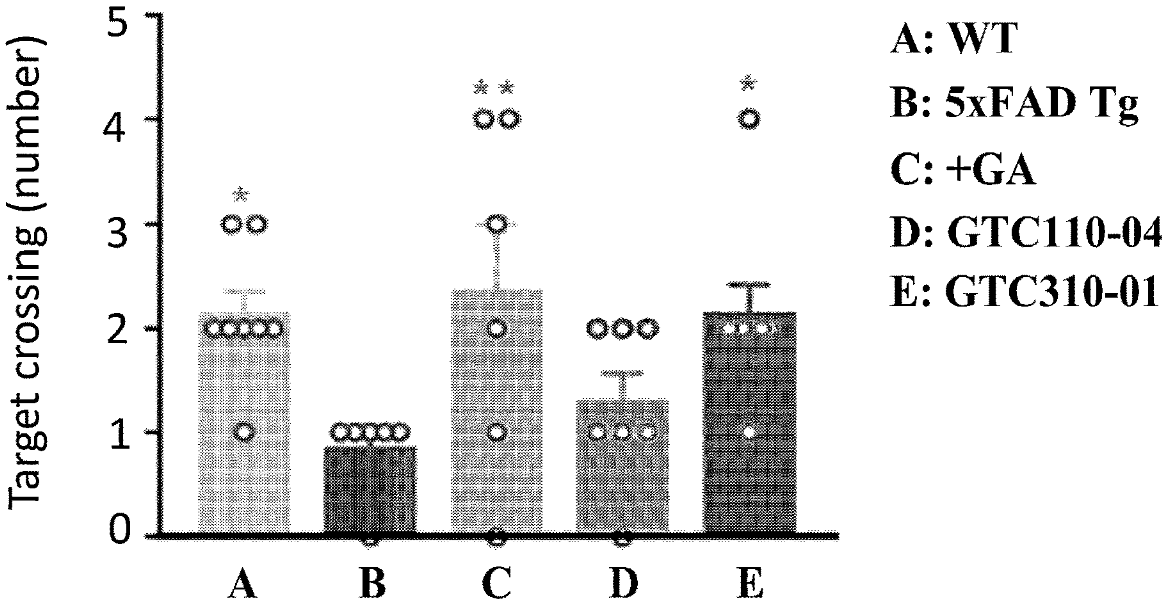
FIG. 15 illustrates a graph showing changes in the number of times the Alzheimer's-induced mice passed the target as a result of the water maze experiment after each treatment of Alzheimer's-induced mice with the monoclonal antibody according to an embodiment of the present invention.
Figure 16:
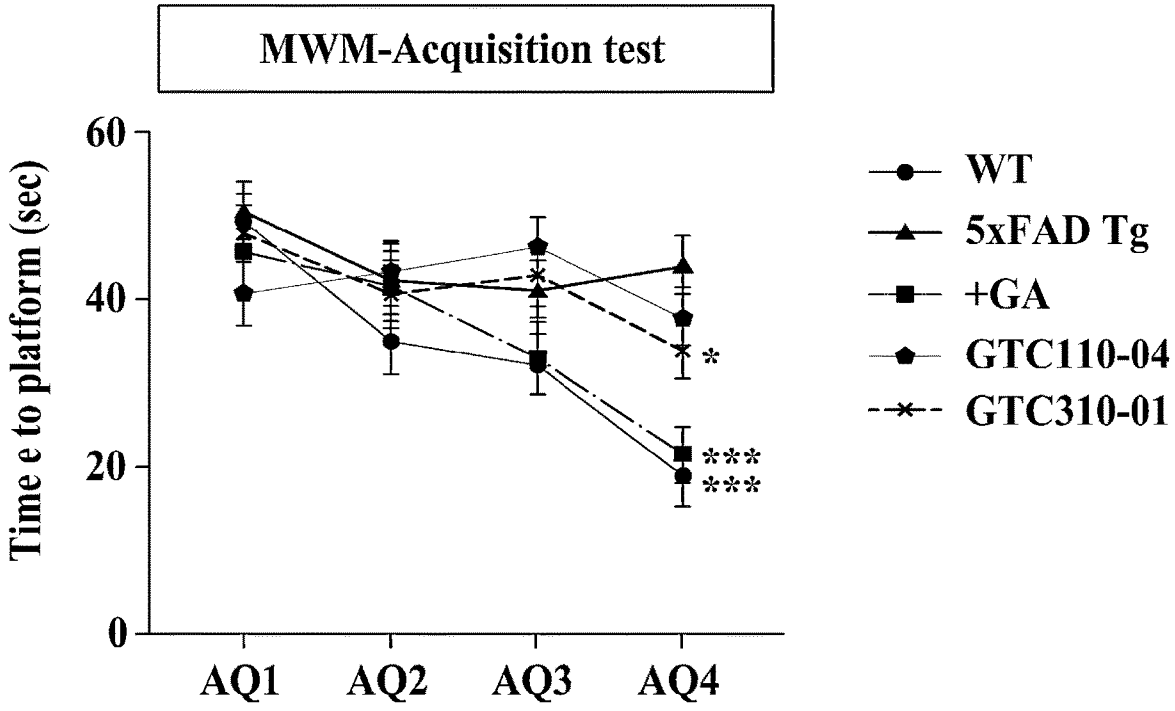
FIG. 16 illustrates a graph showing calculated changes in the time taken to reach the position of the platform during the water maze experiment after each treatment of Alzheimer's-induced mice with the monoclonal antibody according to an embodiment of the present invention.

The water maze test was conducted based on the method devised by Morris. A stainless-steel pool (90 cm in diameter, 50 cm in height) was filled with water (22±1° C.) so that the height of the water surface was 30 cm. A hidden platform (5 cm in diameter) was placed 1 cm below the water surface. On day 1 of evaluation, 3 to 4 training sessions were allowed. A total swimming time per individual was set to 60 seconds; and the individual, who found the platform within 60 seconds, was allowed to stay on the platform for 10 seconds to induce memory. The individual, who was unable to find the platform even after 60 seconds, was manually guided to the platform and allowed to stay on the platform for 10 seconds, wherein the time to escape was set to 60 seconds. On day 6 after the training, a probe test was conducted to calculate spatial perception (time taken to reach the location of the platform (latency to target, sec)) and the number of times it crossed the target (target crossing numbers, number), the results of which are shown in FIGS. 14 and 15, and an acquisition test was conducted to calculate the time taken to reach the platform (time to platform, sec), the result of which is shown in FIG. 16. The analysis was performed using SMART VIDEO TRACKING Software (Panlab, USA). In interpreting the results, the individual included in the exclusion criteria was set as an individual who moves around a specific area without exploration through swimming.

As shown in FIGS. 14 to 16, when the GTC310-01 antibody according to the present invention was administered, the number of times it crossed the target increased significantly, and the time taken to reach the platform significantly decreased.

Through these experiments, it was found that the antibody according to the present invention had a prophylactic, ameliorating, or therapeutic effect on brain and nervous system diseases.

Figure 17:
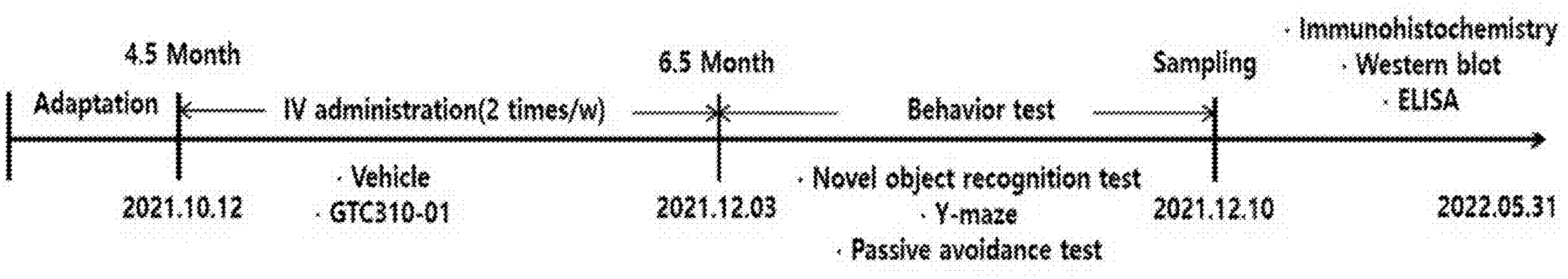
FIG. 17 illustrates an experimental design of Alzheimer's-induced 5×FAD mice and 6×Tg mice for identifying therapeutic effects of monoclonal antibodies on Alzheimer's, according to an embodiment of the present invention.

[Example 7] Evaluation of Therapeutic Effect of Antibodies According to the Present Invention for Alzheimer's—6×Tg Mice In order to evaluate the therapeutic ability of the antibody according to the present invention against Alzheimer's disease, groups were designed as shown in FIG. 17. Specifically, female 5×FAD mice with induced Alzheimer's disease and female 6×Tg mice with induced Alzheimer's disease that underwent an adaptation period of 4.5 months were intravenously injected with GTC310-01 mouse antibody of Preparation Example 1 at an amount of 10 mpk for 2 months. However, glatiramer acetate (GA, Copaxone®) was intravenously injected at an amount of 100 μg for 2 months as a positive control. After 2 months, the Y-maze test, novel object recognition experiment, and passive avoidance test were conducted.

1. Characteristics of 6×Tg Mice

Although the 5×FAD mice is widely used as an Alzheimer's-induced model, thee 6×Tg mice used in the following experiment is a mouse model in which not only amyloid-β (Aβ42) but also tau protein (MAPT) is mutated and accumulated, and thus is a model that is closer to a human disease model than the 5×FAD mouse, thus making it an ideal animal model for neurological diseases including Alzheimer's.

2. Y-Maze Test

For the Y-maze test, a Y-shaped maze was used which had three identical arms having a length of 40 cm (with a 15-cm high wall) at an angle of 120 degrees from each other. This experiment was a behavioral experiment using the rodent's instinctive exploring habit and was based on the fact that there is a high possibility of exploring a new area. The higher the degree that the test animal remembered the arm it had just explored and tried not to enter the same arm, the higher the animal's memory level. An exploring time of 8 minutes was given to each individual, and the final results were expressed as spontaneous alteration (%) values in FIG. 20. The spontaneous alteration (%) value was calculated by Expression 1. Here, behavioral patterns were analyzed using SMART VIDEO TRACKING Software (Panlab, USA).

$$\text{Spontaneous alteration}\,(\%) = \frac{\text{number of triplet}}{\text{total arm entry} - 2} \qquad \text{[Equation 1]}$$

Figure 18:
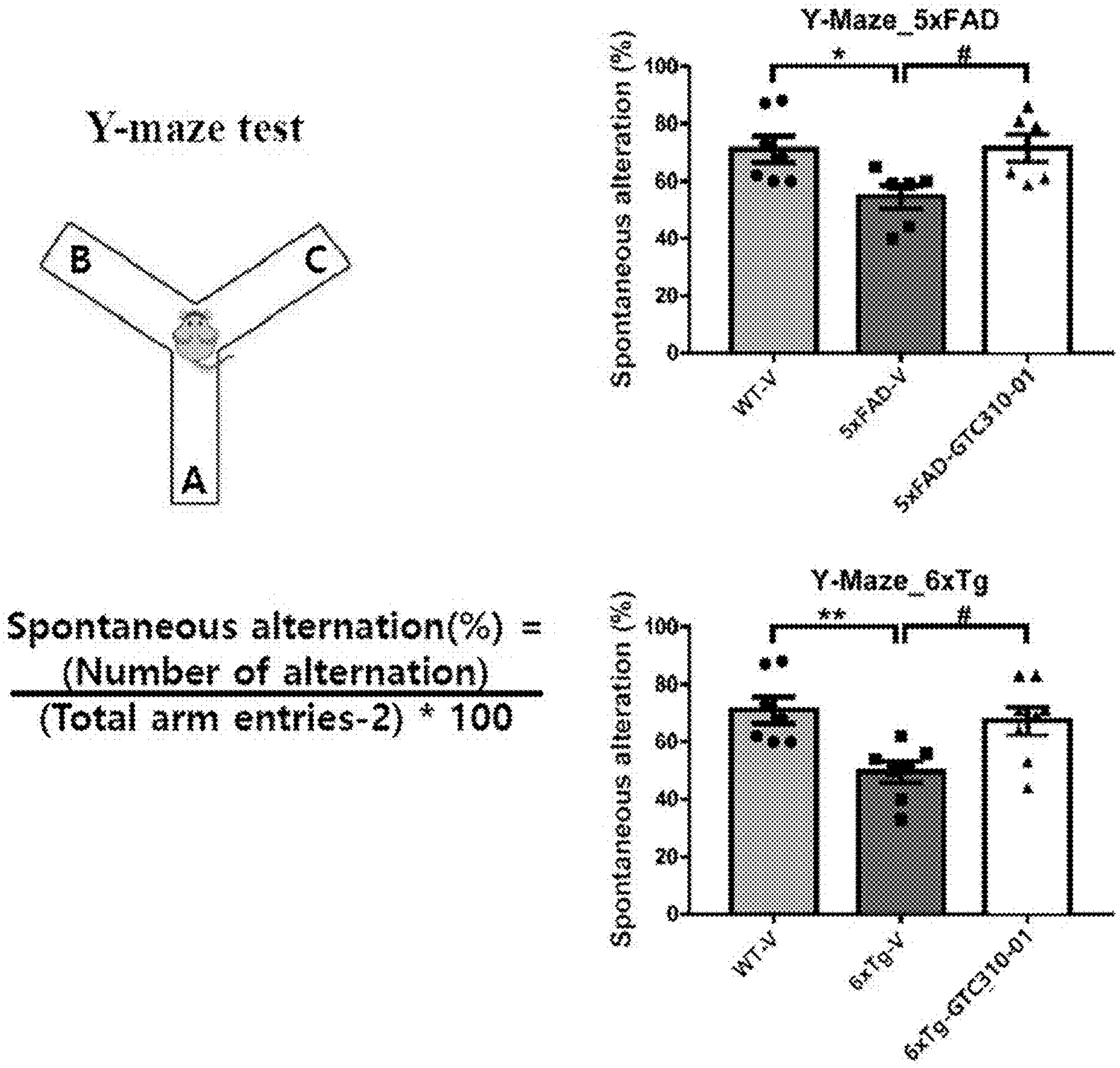
FIG. 18 illustrates a graph showing changes in spontaneous alternation (%) values as a result of Y-maze test after each treatment of Alzheimer's-induced 5×FAD mice and 6×Tg mice with the monoclonal antibody according to an embodiment of the present invention.

As shown in FIG. 18, in this experiment for measuring the relative frequency at which the test animal perceives the surrounding clues and sequentially enters the maze, it was found that in the case where the mice with induced Alzheimer's disease were administered with the GTC310-01 antibody according to the present invention, the mice had a spontaneous alteration value at a level similar to that of a normal control. Furthermore, mice of the 6×Tg model, which is more similar to the human disease model, had a spontaneous alteration value more similar to that of the normal control group than the 5×FAD mouse.

3. Novel Object Recognition

The novel object recognition test was performed to evaluate memory using two different objects in a 40 cm×40 cm acrylic cage. After causing the test animal to acclimatize to the inside of the acrylic cage, two objects were placed at certain locations and the animal was allowed to perceive the objects freely. Then, the time for exploring each object was measured. 24-hour delay was given to each individual, and only one object was changed to another at the same location. Here, in a case where the animal perceives the changed object as a novel object and spends a longer exploring time, it may be determined that the animal has better memory. In a case where the animal does not remember the objects that it explored 24 hours before, the animal fails to distinguish between the novel object and the old object, and thus there is a possibility that the animal explores equally both objects. The animal was allowed to explore freely for a total of 10 minutes, and the result was expressed as a preference index (which equals novel object exploring time/total exploring time) in FIG. 19. Here, the analysis was performed using SMART VIDEO TRACKING Software (Panlab, USA).

Figure 19:
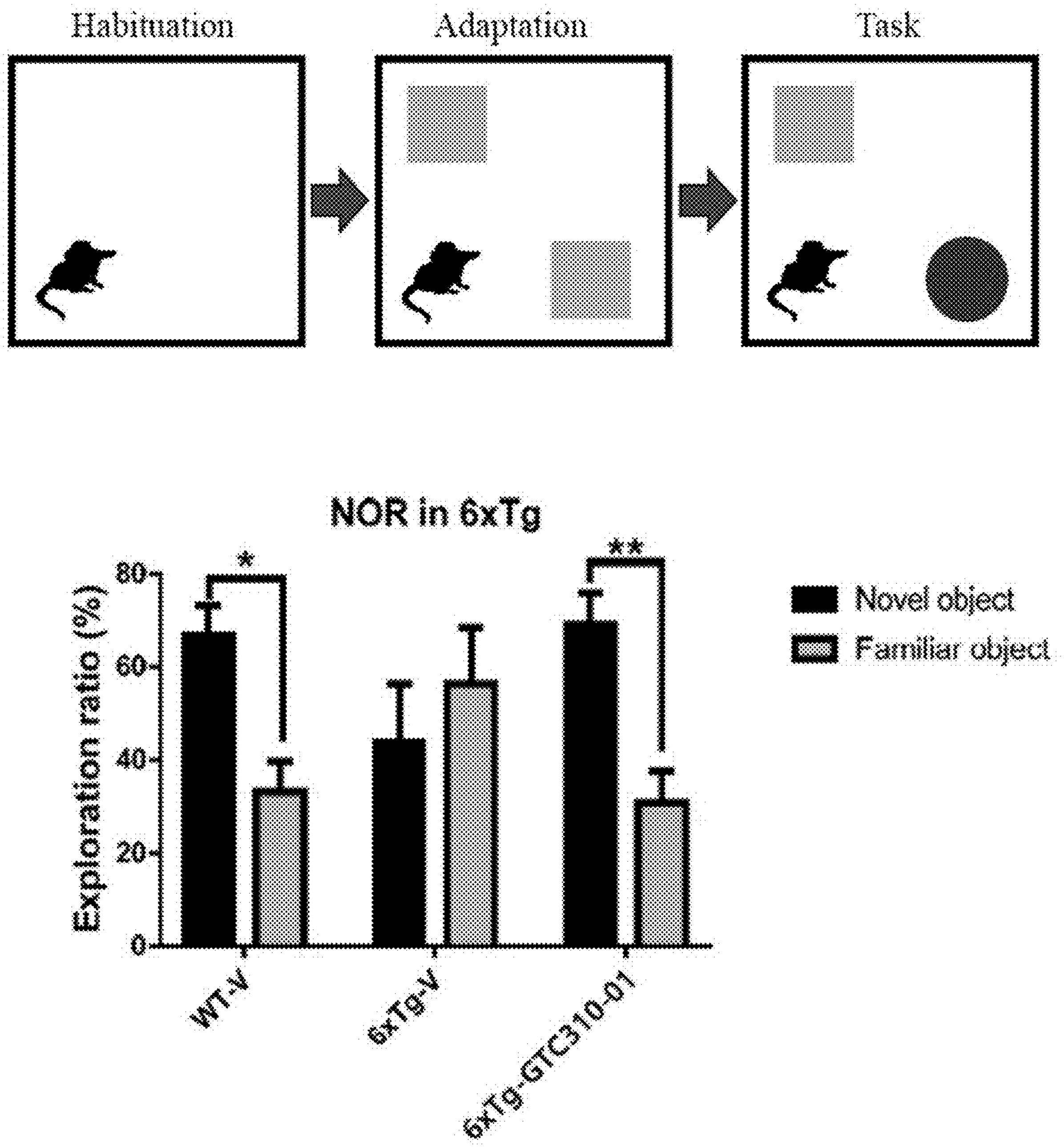
FIG. 19 illustrates a graph showing changes in preference values as a result of a novel object recognition experiment after each treatment of Alzheimer's-induced 6×Tg mice with the monoclonal antibody according to an embodiment of the present invention.

As shown in FIG. 19, the preference index for a new object was lower in the mice with induced Alzheimer's disease compared with the normal control. However, when the GTC310-01 antibody according to the present invention was administered, the preference value was higher than that of the normal control in the 6×Tg model, which is closer to the human disease model.

4. Passive Avoidance Test

Figure 20:
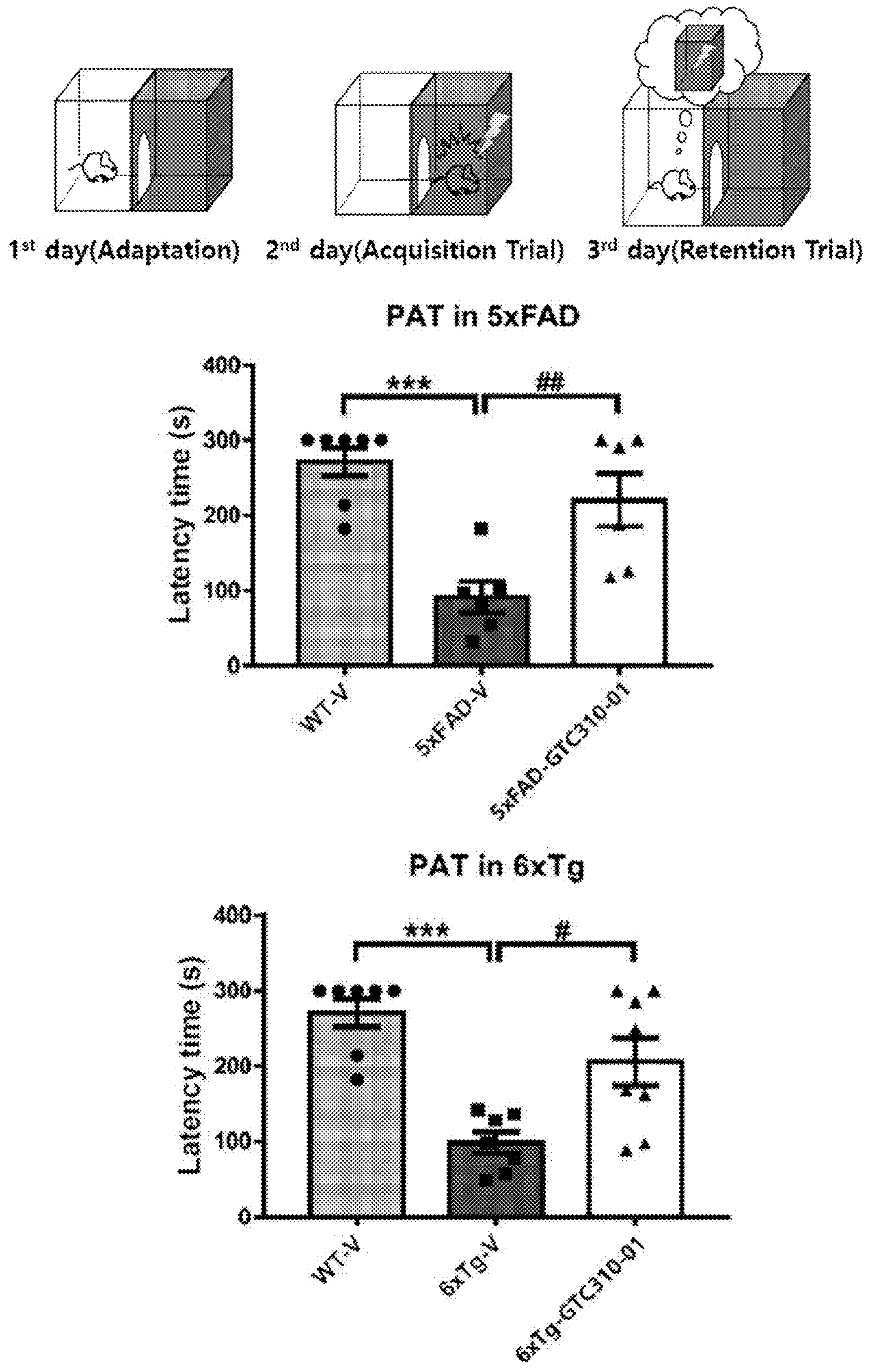
FIG. 20 illustrate a graph showing changes in retention time as a result of a passive avoidance experiment after each treatment of Alzheimer's-induced 5×FAD mice and 6×Tg mice with the monoclonal antibody according to an embodiment of the present invention.

The passive avoidance test experimental equipment is divided into two zones, a bright chamber with lighting and a dark chamber, and the floor is made of wire mesh. On the first day, the mice were allowed to freely move and adapted. The following day, each of the 5×FAD mice and 6×Tg mice were adapted in a lighted chamber without the lights on for 1 minutes, then the lights were turned on and the mice were adapted for 2 minutes, and as soon as the mice were moved to the dark chamber, an electric shock was applied at 0.5 mA for 1 second to conduct a learning test. A teat trial was conducted for each mouse on the day following the learning test. 5×FAD mice and 6×Tg mice were placed in the chamber with lights on, and the time taken for all four paws of the 5×FAD mice and 6×Tg mice to enter (latency time) was specified to within 300 seconds. As a result, as shown in FIG. 20, when the GTC310-01 antibody was administered to 5×FAD mice as well as 6×Tg mice, the recovery was close to that of the normal control group.

Although the present invention has been described in detail above, the scope of the present invention is not limited thereto. It will be obvious to those skilled in the art that various modifications and changes can be made without departing from the technical spirit of the present invention described in the claims.

INDUSTRIAL APPLICABILITY

The present invention relates to a novel binding molecule that is excellent for preventing, ameliorating or treating a brain and nervous system disease, and uses thereof to prevent or treat brain and nervous system diseases, particularly neurodegenerative diseases or neuroinflammatory diseases.

```
Sequence List Free Text
<110> Good T Cells, Inc.
<120> Novel binding molecule and use thereof
<130> POPB214473PCT
<160> 54
<170> KoPatentIn 3.0
<210> 1
<211> 759
<212> PRT
<213> Homo sapiens
<400> 1
Gly Pro Arg Ala Pro Cys Ala Ala Ala Cys Thr Cys Ala Gly Asp Ser
  1               5                  10                  15

Leu Asp Cys Gly Gly Arg Gly Leu Ala Ala Leu Pro Gly Asp Leu Pro
             20                  25                  30

Ser Trp Thr Arg Ser Leu Asn Leu Ser Tyr Asn Lys Leu Ser Glu Ile
         35                  40                  45

Asp Pro Ala Gly Phe Glu Asp Leu Pro Asn Leu Gln Glu Val Tyr Leu
     50                  55                  60

Asn Asn Asn Glu Leu Thr Ala Val Pro Ser Leu Gly Ala Ala Ser Ser
 65                  70                  75                  80
```

-continued

```
His Val Val Ser Leu Phe Leu Gln His Asn Lys Ile Arg Ser Val Glu
                85                  90                  95

Gly Ser Gln Leu Lys Ala Tyr Leu Ser Leu Glu Val Leu Asp Leu Ser
            100                 105                 110

Leu Asn Asn Ile Thr Glu Val Arg Asn Thr Cys Phe Pro His Gly Pro
        115                 120                 125

Pro Ile Lys Glu Leu Asn Leu Ala Gly Asn Arg Ile Gly Thr Leu Glu
    130                 135                 140

Leu Gly Ala Phe Asp Gly Leu Ser Arg Ser Leu Leu Thr Leu Arg Leu
145                 150                 155                 160

Ser Lys Asn Arg Ile Thr Gln Leu Pro Val Arg Ala Phe Lys Leu Pro
                165                 170                 175

Arg Leu Thr Gln Leu Asp Leu Asn Arg Asn Arg Ile Arg Leu Ile Glu
            180                 185                 190

Gly Leu Thr Phe Gln Gly Leu Asn Ser Leu Glu Val Leu Lys Leu Gln
        195                 200                 205

Arg Asn Asn Ile Ser Lys Leu Thr Asp Gly Ala Phe Trp Gly Leu Ser
    210                 215                 220

Lys Met His Val Leu His Leu Glu Tyr Asn Ser Leu Val Glu Val Asn
225                 230                 235                 240

Ser Gly Ser Leu Tyr Gly Leu Thr Ala Leu His Gln Leu His Leu Ser
                245                 250                 255

Asn Asn Ser Ile Ala Arg Ile His Arg Lys Gly Trp Ser Phe Cys Gln
            260                 265                 270

Lys Leu His Glu Leu Val Leu Ser Phe Asn Asn Leu Thr Arg Leu Asp
        275                 280                 285

Glu Glu Ser Leu Ala Glu Leu Ser Ser Leu Ser Val Leu Arg Leu Ser
    290                 295                 300

His Asn Ser Ile Ser His Ile Ala Glu Gly Ala Phe Lys Gly Leu Arg
305                 310                 315                 320

Ser Leu Arg Val Leu Asp Leu Asp His Asn Glu Ile Ser Gly Thr Ile
                325                 330                 335

Glu Asp Thr Ser Gly Ala Phe Ser Gly Leu Asp Ser Leu Ser Lys Leu
            340                 345                 350

Thr Leu Phe Gly Asn Lys Ile Lys Ser Val Ala Lys Arg Ala Phe Ser
        355                 360                 365

Gly Leu Glu Gly Leu Glu His Leu Asn Leu Gly Gly Asn Ala Ile Arg
    370                 375                 380

Ser Val Gln Phe Asp Ala Phe Val Lys Met Lys Asn Leu Lys Glu Leu
385                 390                 395                 400

His Ile Ser Ser Asp Ser Phe Leu Cys Asp Cys Gln Leu Lys Trp Leu
                405                 410                 415

Pro Pro Trp Leu Ile Gly Arg Met Leu Gln Ala Phe Val Thr Ala Thr
            420                 425                 430

Cys Ala His Pro Glu Ser Leu Lys Gly Gln Ser Ile Phe Ser Val Pro
        435                 440                 445

Pro Glu Ser Phe Val Cys Asp Asp Phe Leu Lys Pro Gln Ile Ile Thr
    450                 455                 460

Gln Pro Glu Thr Thr Met Ala Met Val Gly Lys Asp Ile Arg Phe Thr
465                 470                 475                 480

Cys Ser Ala Ala Ser Ser Ser Ser Ser Pro Met Thr Phe Ala Trp Lys
                485                 490                 495

Lys Asp Asn Glu Val Leu Thr Asn Ala Asp Met Glu Asn Phe Val His
            500                 505                 510
```

-continued

Val His Ala Gln Asp Gly Glu Val Met Glu Tyr Thr Thr Ile Leu His
515 520 525

Leu Arg Gln Val Thr Phe Gly His Glu Gly Arg Tyr Gln Cys Val Ile
530 535 540

Thr Asn His Phe Gly Ser Thr Tyr Ser His Lys Ala Arg Leu Thr Val
545 550 555 560

Asn Val Leu Pro Ser Phe Thr Lys Thr Pro His Asp Ile Thr Ile Arg
565 570 575

Thr Thr Thr Val Ala Arg Leu Glu Cys Ala Ala Thr Gly His Pro Asn
580 585 590

Pro Gln Ile Ala Trp Gln Lys Asp Gly Gly Thr Asp Phe Pro Ala Ala
595 600 605

Arg Glu Arg Arg Met His Val Met Pro Asp Asp Asp Val Phe Phe Ile
610 615 620

Thr Asp Val Lys Ile Asp Asp Ala Gly Val Tyr Ser Cys Thr Ala Gln
625 630 635 640

Asn Ser Ala Gly Ser Ile Ser Ala Asn Ala Thr Leu Thr Val Leu Glu
645 650 655

Thr Pro Ser Leu Val Val Pro Leu Glu Asp Arg Val Val Ser Val Gly
660 665 670

Glu Thr Val Ala Leu Gln Cys Lys Ala Thr Gly Asn Pro Pro Pro Arg
675 680 685

Ile Thr Trp Phe Lys Gly Asp Arg Pro Leu Ser Leu Thr Glu Arg His
690 695 700

His Leu Thr Pro Asp Asn Gln Leu Leu Val Val Gln Asn Val Val Ala
705 710 715 720

Glu Asp Ala Gly Arg Tyr Thr Cys Glu Met Ser Asn Thr Leu Gly Thr
725 730 735

Glu Arg Ala His Ser Gln Leu Ser Val Leu Pro Ala Ala Gly Cys Arg
740 745 750

Lys Asp Gly Thr Thr Val Gly
755

<210> 2
<211> 2397
<212> DNA
<213> *Homo sapiens*
<400> 2
ggcccgcggg cgccctgcgc ggccgcctgc acttgcgctg gggactcgct ggactgcggt 60
gggcgcgggc tggctgcgtt gcccggggac ctgccctcct ggacgcggag cctaaacctg 120
agttacaaca aactctctga gattgaccct gctggttttg aggacttgcc gaacctacag 180
gaagtgtacc tcaataataa tgagttgaca gcggtaccat ccctgggcgc tgcttcatca 240
catgtcgtct ctctctttct gcagcacaac aagattcgca gcgtggaggg gagccagctg 300
aaggcctacc tttccttaga agtgttagat ctgagtttga acaacatcac ggaagtgcgg 360
aacacctgct ttccacacgg accgcctata aaggagctca acctggcagg caatcggatt 420
ggcaccctgg agttgggagc atttgatggt ctgtcacggt cgctgctaac tcttcgcctg 480
agcaaaaaca ggatcaccca gcttcctgta agagcattca agctacccag gctgacacaa 540
ctggacctca atcggaacag gattcggctg atagagggcc tcaccttcca ggggctcaac 600
agcttggagg tgctgaagct tcagcgaaac aacatcagca aactgacaga tggggccttc 660
tggggactgt ccaagatgca tgtgctgcac ctggagtaca acagcctggt agaagtgaac 720
agcggctcgc tctacggcct cacggccctg catcagctcc acctcagcaa caattccatc 780
gctcgcattc accgcaaggg ctggagcttc tgccagaagc tgcatgagtt ggtcctgtcc 840

-continued

```
ttcaacaacc tgacacggct ggacgaggag agcctggccg agctgagcag cctgagtgtc  900
ctgcgtctca gccacaattc catcagccac attgcggagg gtgccttcaa gggactcagg  960
agcctgcgag tcttggatct ggaccataac gagatttcgg gcacaataga ggacacgagc 1020
ggcgccttct cagggctcga cagcctcagc aagctgactc tgtttggaaa caagatcaag 1080
tctgtggcta agagagcatt ctcggggctg gaaggcctgg agcacctgaa ccttggaggg 1140
aatgcgatca gatctgtcca gtttgatgcc tttgtgaaga tgaagaatct taaagagctc 1200
catatcagca gcgacagctt cctgtgtgac tgccagctga agtggctgcc cccgtggcta 1260
attggcagga tgctgcaggc ctttgtgaca gccacctgtg cccacccaga atcactgaag 1320
ggtcagagca ttttctctgt gccaccagag agtttcgtgt gcgatgactt cctgaagcca 1380
cagatcatca cccagccaga aaccaccatg gctatggtgg gcaaggacat ccggtttaca 1440
tgctcagcag ccagcagcag cagctccccc atgacctttg cctggaagaa agacaatgaa 1500
gtcctgacca atgcagacat ggagaacttt gtccacgtcc acgcgcagga cggggaagtg 1560
atggagtaca ccaccatcct gcacctccgt caggtcactt tcgggcacga gggccgctac 1620
caatgtgtca tcaccaacca ctttggctcc acctattcac ataaggccag gctcaccgtg 1680
aatgtgttgc catcattcac caaaacgccc cacgacataa ccatccggac caccaccgtg 1740
gcccgcctcg aatgtgctgc cacaggtcac ccaaaccctc agattgcctg gcagaaggat 1800
ggaggcacgg atttccccgc tgcccgtgag cgacgcatgc atgtcatgcc ggatgacgac 1860
gtgtttttca tcactgatgt gaaaatagat gacgcagggg tttacagctg tactgctcag 1920
aactcagccg gttctatttc agctaatgcc accctgactg tcctagagac cccatccttg 1980
gtggtcccct tggaagaccg tgtggtatct gtgggagaaa cagtggccct ccaatgcaaa 2040
gccacgggga accctccgcc ccgcatcacc tggttcaagg gggaccgccc gctgagcctc 2100
actgagcggc accacctgac ccctgacaac cagctcctgg tggttcagaa cgtggtggca 2160
gaggatgcgg gccgatatac ctgtgagatg tccaacaccc tgggcacgga gcgagctcac 2220
agccagctga gcgtcctgcc cgcagcaggc tgcaggaagg atgggaccac ggtaggcatc 2280
ttcaccattg ctgtcgtgag cagcatcgtc ctgacgtcac tggtctgggt gtgcatcatc 2340
taccagacca ggaagaagag tgaagagtac agtgtcacca acacagatga aaccgtc    2397
```

<210> 3
<211> 761
<212> PRT
<213> *Mus musculus*
<400> 3

```
Gln Ala Gly Pro Arg Ala Pro Cys Ala Ala Ala Cys Thr Cys Ala Gly
  1               5                  10                  15

Asp Ser Leu Asp Cys Ser Gly Arg Gly Leu Ala Thr Leu Pro Arg Asp
             20                  25                  30

Leu Pro Ser Trp Thr Arg Ser Leu Asn Leu Ser Tyr Asn Arg Leu Ser
         35                  40                  45

Glu Ile Asp Ser Ala Ala Phe Glu Asp Leu Thr Asn Leu Gln Glu Val
     50                  55                  60

Tyr Leu Asn Ser Asn Glu Leu Thr Ala Ile Pro Ser Leu Gly Ala Ala
 65                  70                  75                  80

Ser Ile Gly Val Val Ser Leu Phe Leu Gln His Asn Lys Ile Leu Ser
                 85                  90                  95

Val Asp Gly Ser Gln Leu Lys Ser Tyr Leu Ser Leu Glu Val Leu Asp
            100                 105                 110

Leu Ser Ser Asn Asn Ile Thr Glu Ile Arg Ser Ser Cys Phe Pro Asn
        115                 120                 125
```

-continued

```
Gly Leu Arg Ile Arg Glu Leu Asn Leu Ala Ser Asn Arg Ile Ser Ile
     130                 135                 140

Leu Glu Ser Gly Ala Phe Asp Gly Leu Ser Arg Ser Leu Leu Thr Leu
145                 150                 155                 160

Arg Leu Ser Lys Asn Arg Ile Thr Gln Leu Pro Val Lys Ala Phe Lys
                165                 170                 175

Leu Pro Arg Leu Thr Gln Leu Asp Leu Asn Arg Asn Arg Ile Arg Leu
            180                 185                 190

Ile Glu Gly Leu Thr Phe Gln Gly Leu Asp Ser Leu Glu Val Leu Arg
        195                 200                 205

Leu Gln Arg Asn Asn Ile Ser Arg Leu Thr Asp Gly Ala Phe Trp Gly
    210                 215                 220

Leu Ser Lys Met His Val Leu His Leu Glu Tyr Asn Ser Leu Val Glu
225                 230                 235                 240

Val Asn Ser Gly Ser Leu Tyr Gly Leu Thr Ala Leu His Gln Leu His
                245                 250                 255

Leu Ser Asn Asn Ser Ile Ser Arg Ile Gln Arg Asp Gly Trp Ser Phe
            260                 265                 270

Cys Gln Lys Leu His Glu Leu Ile Leu Ser Phe Asn Asn Leu Thr Arg
        275                 280                 285

Leu Asp Glu Glu Ser Leu Ala Glu Leu Ser Ser Leu Ser Ile Leu Arg
    290                 295                 300

Leu Ser His Asn Ala Ile Ser His Ile Ala Glu Gly Ala Phe Lys Gly
305                 310                 315                 320

Leu Lys Ser Leu Arg Val Leu Asp Leu Asp His Asn Glu Ile Ser Gly
                325                 330                 335

Thr Ile Glu Asp Thr Ser Gly Ala Phe Thr Gly Leu Asp Asn Leu Ser
            340                 345                 350

Lys Leu Thr Leu Phe Gly Asn Lys Ile Lys Ser Val Ala Lys Arg Ala
        355                 360                 365

Phe Ser Gly Leu Glu Ser Leu Glu His Leu Asn Leu Gly Glu Asn Ala
    370                 375                 380

Ile Arg Ser Val Gln Phe Asp Ala Phe Ala Lys Met Lys Asn Leu Lys
385                 390                 395                 400

Glu Leu Tyr Ile Ser Ser Glu Ser Phe Leu Cys Asp Cys Gln Leu Lys
                405                 410                 415

Trp Leu Pro Pro Trp Leu Met Gly Arg Met Leu Gln Ala Phe Val Thr
            420                 425                 430

Ala Thr Cys Ala His Pro Glu Ser Leu Lys Gly Gln Ser Ile Phe Ser
        435                 440                 445

Val Leu Pro Asp Ser Phe Val Cys Asp Asp Phe Pro Lys Pro Gln Ile
    450                 455                 460

Ile Thr Gln Pro Glu Thr Thr Met Ala Val Val Gly Lys Asp Ile Arg
465                 470                 475                 480

Phe Thr Cys Ser Ala Ala Ser Ser Ser Ser Ser Pro Met Thr Phe Ala
                485                 490                 495

Trp Lys Lys Asp Asn Glu Val Leu Ala Asn Ala Asp Met Glu Asn Phe
            500                 505                 510

Ala His Val Arg Ala Gln Asp Gly Glu Val Met Glu Tyr Thr Thr Ile
        515                 520                 525

Leu His Leu Arg His Val Thr Phe Gly His Glu Gly Arg Tyr Gln Cys
    530                 535                 540

Ile Ile Thr Asn His Phe Gly Ser Thr Tyr Ser His Lys Ala Arg Leu
545                 550                 555                 560
```

-continued

```
Thr Val Asn Val Leu Pro Ser Phe Thr Lys Ile Pro His Asp Ile Ala
                565                 570                 575

Ile Arg Thr Gly Thr Thr Ala Arg Leu Glu Cys Ala Ala Thr Gly His
            580                 585                 590

Pro Asn Pro Gln Ile Ala Trp Gln Lys Asp Gly Gly Thr Asp Phe Pro
        595                 600                 605

Ala Ala Arg Glu Arg Arg Met His Val Met Pro Asp Asp Asp Val Phe
    610                 615                 620

Phe Ile Thr Asp Val Lys Ile Asp Asp Met Gly Val Tyr Ser Cys Thr
625                 630                 635                 640

Ala Gln Asn Ser Ala Gly Ser Val Ser Ala Asn Ala Thr Leu Thr Val
                645                 650                 655

Leu Glu Thr Pro Ser Leu Ala Val Pro Leu Glu Asp Arg Val Val Thr
            660                 665                 670

Val Gly Glu Thr Val Ala Phe Gln Cys Lys Ala Thr Gly Ser Pro Thr
        675                 680                 685

Pro Arg Ile Thr Trp Leu Lys Gly Gly Arg Pro Leu Ser Leu Thr Glu
    690                 695                 700

Arg His His Phe Thr Pro Gly Asn Gln Leu Leu Val Val Gln Asn Val
705                 710                 715                 720

Met Ile Asp Asp Ala Gly Arg Tyr Thr Cys Glu Met Ser Asn Pro Leu
                725                 730                 735

Gly Thr Glu Arg Ala His Ser Gln Leu Ser Ile Leu Pro Thr Pro Gly
            740                 745                 750

Cys Arg Lys Asp Gly Thr Thr Val Gly
        755                 760
```

<210> 4
<211> 2283
<212> DNA
<213> *Mus musculus*
<400> 4

```
caggctggcc cgcgggcccc ctgcgcggcc gcctgcactt gcgccgggga ctcgctggac   60

tgcagtgggc gcgggctggc gacgctgccc cgggacctgc cctcctggac gcgcagccta  120

aacctgagtt ataacagact ctccgagatc gactctgctg cttttgagga cttgacgaat  180

ctgcaggaag tgtacctcaa cagcaatgag ctgacagcca taccatcact gggcgctgct  240

tccataggag ttgtctctct ctttttgcag cacaacaaga tccttagtgt ggatgggagc  300

cagctgaagt cgtacctgtc cttggaagtg ctggatctga gttccaacaa catcacggaa  360

attcggagct cctgtttccc gaacggcctg cgtataaggg aactcaactt ggcgagcaac  420

cgcatcagca tcctggagtc tggagcattt gatggtctgt cgcggtcact gctgactctc  480

cgtctgagca aaaacaggat cacccagctt cctgtgaaag cgttcaagct acccaggctg  540

acacaactag acctgaatcg gaatcggatt cggctgattg aaggcctcac gttccagggg  600

ctcgacagct tagaggtgct gaggcttcag aggaacaaca tcagcaggct gacggacggg  660

gccttctggg ggctgtctaa gatgcacgtg ctgcacctgg agtacaacag tctggtggaa  720

gtgaacagtg gctccctcta tggcctcaca gccctgcacc agctgcacct cagcaacaac  780

tccatctctc gaattcagcg tgatggctgg agcttctgcc aaaagctgca tgagttgatt  840

ctgtccttca acaacctcac gcggctggat gaggagagtc tagcggagtt gagcagcctc  900

agtatcctgc gcctcagtca caacgccatc agtcacattg ctgaaggcgc cttcaaggga  960

ctcaagagtc tgcgggtctt ggacctggac cataacgaga tctcgggtac aatcgaggat 1020

accagtggtg cctttacggg gcttgacaac ctcagcaagc tgactctgtt tggaaacaag 1080
```

-continued

```
atcaaatctg tggctaagag agccttctcg ggcctggaaa gcctggaaca cctgaacctt 1140

ggagagaatg caatcaggtc tgtccagttt gatgcctttg caaagatgaa gaaccttaaa 1200

gagctctaca tcagcagtga gagcttcctg tgtgactgcc agctcaagtg gctgccccca 1260

tggctaatgg gtaggatgct gcaggccttt gtgacagcca cctgtgccca tccagagtcg 1320

ctgaagggcc agagcatttt ctcagtgctg ccagacagct ttgtgtgtga tgactttcca 1380

aagccacaga tcatcaccca gcctgagacg accatggctg tggtgggcaa ggacatccgt 1440

ttcacatgct ccgcagccag cagcagcagc tcaccaatga ccttcgcctg gaagaaggac 1500

aatgaggtcc tggccaatgc agacatggag aactttgccc acgtccgtgc acaggacggc 1560

gaagtgatgg agtataccac tatcctgcac ctccgtcacg tcacctttgg gcacgagggc 1620

cgctaccagt gtatcatcac aaaccacttt ggctccacat actcccacaa agccaggctc 1680

actgtgaatg tgttgccatc attcactaaa ataccccatg acattgccat ccggactggc 1740

accacagccc gcctcgagtg tgctgccacg ggccacccta accctcagat tgcctggcag 1800

aaggatggag gcaccgattt cccggcagct cgtgagcgac gcatgcatgt tatgccagac 1860

gatgatgtgt tcttcatcac tgatgtgaaa atagacgaca tgggggtcta cagctgcact 1920

gcccagaact cggcaggctc ggtttcagcc aacgctaccc tcacagtctt agaaactcca 1980

tccttggcag tgcctctgga agaccgtgtg gtaactgtgg gagaaacagt ggccttccag 2040

tgcaaagcaa ccgggagccc cacaccacgc atcacctggc ttaagggagg tcgcccattg 2100

agcctcacag agcgccacca tttcactcca ggcaaccagc tgctggttgt tcagaatgtg 2160

atgatagacg atgcagggcg gtatacctgt gagatgtcta atcccctggg cactgagcga 2220

gcacatagcc agctgagcat tttacctacc cctggctgcc ggaaggatgg gaccaccgta 2280

ggc                                                               2283
```

```
<210> 5
<211> 5
<212> PRT
<213> Artificial Sequence
<220>
<223> Heavy chain CDR 1
<400> 5
Asn Tyr Ala Met Ser
 1               5

<210> 6
<211> 17
<212> PRT
<213> Artificial Sequence
<220>
<223> Heavy chain CDR 2
<400> 6
Val Ile Ser His Gly Gly Gly Ser Thr Tyr Tyr Ala Asp Ser Val Lys
 1                 5                       10                      15

Gly

<210> 7
<211> 18
<212> PRT
<213> Artificial Sequence
<220>
<223> Heavy chain CDR 3
<400> 7
Val Ile Ser Asn Cys His Leu Gly Val Cys Tyr Tyr Ser Asn Gly Met
 1                5                       10                      15

Asp Val

<210> 8
<211> 13
<212> PRT
<213> Artificial Sequence
<220>
```

-continued

<223> Light chain CDR 1
<400> 8
Ser Gly Ser Ser Ser Asn Ile Gly Asp Asn Tyr Val Ser
1 5 10

<210> 9
<211> 7
<212> PRT
<213> Artificial Sequence
<220>
*884<223> Light chain CDR 2
<400> 9
Asp Asn Asn Lys Arg Pro Ser
1 5

<210> 10
<211> 10
<212> PRT
<213> Artificial Sequence
<220>
<223> Light chain CDR 3
<400> 10
Trp Asp Gly Ser Leu Ser Ala Gly Arg Val
1 5 10

<210> 11
<211> 127
<212> PRT
<213> Artificial Sequence
<220>
<223> Heavy chain variable region
<400> 11
Glu Val Gln Leu Leu Glu Ser Gly Gly Gly Leu Val Gln Pro Gly Gly
1 5 10 15

*918
Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Val Ile Ser His Gly Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

*930
Leu Gln Met Asn Ser Leu Arg Ala Glu Asp Thr Ala Val Tyr Tyr Cys
85 90 95

Ala Arg Val Ile Ser Asn Cys His Leu Gly Val Cys Tyr Tyr Ser Asn
100 105 110

Gly Met Asp Val Trp Gly Gln Gly Thr Leu Val Thr Val Ser Ser
115 120 125

<210> 12
<211> 111
<212> PRT
<213> Artificial Sequence
<220>
<223> Light chain variable region
<400> 12
Gln Leu Val Leu Thr Gln Pro Pro Ser Val Ser Ala Ala Pro Gly Gln
1 5 10 15

*955
Arg Val Ser Ile Ser Cys Ser Gly Ser Ser Ser Asn Ile Gly Asp Asn
20 25 30

Tyr Val Ser Trp Tyr Gln Gln Val Pro Gly Ser Ala Pro Lys Leu Leu
35 40 45

Ile Tyr Asp Asn Asn Lys Arg Pro Ser Gly Ile Pro Asp Arg Phe Ser
50 55 60

Ala Ser Lys Ser Gly Thr Ser Ala Thr Leu Gly Ile Thr Gly Leu Gln
65 70 75 80

-continued

*967
Thr Gly Asp Glu Ala Asp Tyr Tyr Cys Ala Thr Trp Asp Gly Ser Leu
85 90 95

Ser Ala Gly Arg Val Phe Gly Gly Gly Thr Lys Leu Thr Val Leu
100 105 110

<210> 13
<211> 15
<212> DNA
<213> Artificial Sequence
<220>
<223> Heavy chain CDR 1
<400> 13
aactacgcca tgagc 15

<210> 14
<211> 51
<212> DNA
<213> Artificial Sequence
<220>
<223> Heavy chain CDR 2
<400> 14
gtgatctctc acggcggagg cagcacctac tacgccgatt ctgtgaaggg c 51

<210> 15
<211> 54
<212> DNA
<213> Artificial Sequence
<220>
<223> Heavy chain CDR 3
*1009
<400> 15
gtgatcagca actgccacct gggcgtgtgc tactacagca acggcatgga tgtg 54

<210> 16
<211> 39
<212> DNA
<213> Artificial Sequence
<220>
<223> Light chain CDR 1
*1022
<400> 16
agcggcagca gcagcaacat cggcgacaac tacgtgtcc 39

<210> 17
<211> 21
<212> DNA
<213> Artificial Sequence
<220>
<223> Light chain CDR 2
*1035
<400> 17
gacaacaaca agcggcccag c 21

<210> 18
<211> 30
<212> DNA
<213> Artificial Sequence
<220>
<223> Light chain CDR 3
*1048
<400> 18
tgggatggct ccctgagcgc cggaagagtt 30

<210> 19
<211> 381
<212> DNA
<213> Artificial Sequence
<220>
<223> Heavy chain variable region
<400> 19
gaagttcagc tgcttgagtc tggcggagga ctggttcaac ctggcggaag cctgagactg 60
tcttgtgccg ccagcggctt caccttcagc aactacgcca tgagctgggt ccgacaggcc 120
cctggaaaag gccttgaatg ggtgtccgtg atctctcacg gcggaggcag cacctactac 180
gccgattctg tgaagggcag attcaccatc agccgggaca acagcaagaa caccctgtac 240
ctgcagatga acagcctgag agccgaggac accgccgtgt actattgcgc cagagtgatc 300

-continued agcaactgcc acctgggcgt gtgctactac agcaacggca tggatgtgtg gggccagggc 360
acactggtta ccgttagttc t 381

<210> 20
<211> 333
<212> DNA
<213> Artificial Sequence
<220>
<223> Light chain variable region
<400> 20
caactggttc tgacacagcc tccaagcgtg tcagctgccc ctggacagag agtgtccatc 60
agctgtagcg gcagcagcag caacatcggc gacaactacg tgtcctggta tcagcaggtc 120
ccaggctctg cccctaagct gctgatctac gacaacaaca agcggcccag cggcatcccc 180
gatagatttt ctgccagcaa gagcggcacc agcgccacac tgggaattac aggactgcag 240
acaggcgacg aggccgacta ctattgtgcc acatgggatg gctccctgag cgccggaaga 300
gtttttggcg gaggcaccaa gctgaccgtg ctt 333

<210> 21
<211> 328
<212> PRT
<213> *Mus musculus*
<400> 21
Thr Thr Ala Pro Ser Val Tyr Pro Leu Ala Pro Val Cys Gly Asp Thr
1 5 10 15

Thr Gly Ser Ser Val Thr Leu Gly Cys Leu Val Lys Gly Tyr Phe Pro
20 25 30

Glu Pro Val Thr Leu Thr Trp Asn Ser Gly Ser Leu Ser Ser Gly Val
35 40 45

His Thr Phe Pro Ala Val Leu Gln Ser Asp Leu Tyr Thr Leu Ser Ser
50 55 60

Ser Val Thr Val Thr Ser Ser Thr Trp Pro Ser Gln Ser Ile Thr Cys
65 70 75 80

Asn Val Ala His Pro Ala Ser Ser Thr Lys Val Asp Lys Lys Ile Glu
85 90 95

Pro Arg Gly Pro Thr Ile Lys Pro Cys Pro Pro Cys Lys Cys Pro Ala
100 105 110

Pro Asn Leu Leu Gly Gly Pro Ser Val Phe Ile Phe Pro Pro Lys Ile
115 120 125

Lys Asp Val Leu Met Ile Ser Leu Ser Pro Ile Val Thr Cys Val Val
130 135 140

Val Asp Val Ser Glu Asp Asp Pro Asp Val Gln Ile Ser Trp Phe Val
145 150 155 160

Asn Asn Val Glu Val His Thr Ala Gln Thr Gln Thr His Arg Glu Asp
165 170 175

Tyr Asn Ser Thr Leu Arg Val Val Ser Ala Leu Pro Ile Gln His Gln
180 185 190

Asp Trp Met Ser Gly Lys Glu Phe Lys Cys Lys Val Asn Asn Lys Asp
195 200 205

Leu Pro Ala Pro Ile Glu Arg Thr Ile Ser Lys Pro Lys Gly Ser Val
210 215 220

Arg Ala Pro Gln Val Tyr Val Leu Pro Pro Pro Glu Glu Glu Met Thr
225 230 235 240

Lys Lys Gln Val Thr Leu Thr Cys Met Val Thr Asp Phe Met Pro Glu
245 250 255

Asp Ile Tyr Val Glu Trp Thr Asn Asn Gly Lys Thr Glu Leu Asn Tyr
260 265 270

Lys Asn Thr Glu Pro Val Leu Asp Ser Asp Gly Ser Tyr Phe Met Tyr

-continued 275 280 285

Ser Lys Leu Arg Val Glu Lys Lys Asn Trp Val Glu Arg Asn Ser Tyr
290 295 300

Ser Cys Ser Val Val His Glu Gly Leu His Asn His His Thr Thr Lys
305 310 315 320

Ser Phe Ser Arg Thr Pro Gly Lys
325

<210> 22
<211> 107
<212> PRT
<213> *Mus musculus*
<400> 22
Arg Thr Val Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

Thr Tyr Ser Met Ser Ser Thr Leu Thr Leu Thr Lys Asp Glu Tyr Glu
65 70 75 80

Arg His Asn Ser Tyr Thr Cys Glu Ala Thr His Lys Thr Ser Thr Ser
85 90 95

*1195
Pro Ile Val Lys Ser Phe Asn Arg Asn Glu Cys
100 105

<210> 23
<211> 330
<212> PRT
<213> *Homo sapiens*
<400> 23
Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

-continued

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> 24
<211> 330
<212> PRT
<213> *Homo sapiens*
<400> 24
Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

*1293
Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

-continued

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> 25
<211> 107
<212> PRT
<213> Homo sapiens
<400> 25
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> 26
<211> 107
<212> PRT
<213> Homo sapiens
<400> 26
Arg Ser Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

*1391
Pro Val Thr Lys Ser Phe Asn Arg Gly Glu Cys
            100                 105

<210> 27
<211> 326
<212> PRT
<213> Homo sapiens
<400> 27
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
```

-continued

```
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> 28
<211> 377
<212> PRT
<213> Homo sapiens
<400> 28
Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125
```

-continued

Cys Pro Glu Pro Lys Ser Cys Asp Thr Pro Pro Pro Cys Pro Arg Cys
130 135 140

Pro Glu Pro Lys Ser Cys Asp Thr Pro Pro Pro Cys Pro Arg Cys Pro
145 150 155 160

Ala Pro Glu Leu Leu Gly Gly Pro Ser Val Phe Leu Phe Pro Pro Lys
165 170 175

Pro Lys Asp Thr Leu Met Ile Ser Arg Thr Pro Glu Val Thr Cys Val
180 185 190

Val Val Asp Val Ser His Glu Asp Pro Glu Val Gln Phe Lys Trp Tyr
195 200 205

Val Asp Gly Val Glu Val His Asn Ala Lys Thr Lys Pro Arg Glu Glu
210 215 220

Gln Tyr Asn Ser Thr Phe Arg Val Val Ser Val Leu Thr Val Leu His
225 230 235 240

Gln Asp Trp Leu Asn Gly Lys Glu Tyr Lys Cys Lys Val Ser Asn Lys
245 250 255

Ala Leu Pro Ala Pro Ile Glu Lys Thr Ile Ser Lys Thr Lys Gly Gln
260 265 270

Pro Arg Glu Pro Gln Val Tyr Thr Leu Pro Pro Ser Arg Glu Glu Met
275 280 285

Thr Lys Asn Gln Val Ser Leu Thr Cys Leu Val Lys Gly Phe Tyr Pro
290 295 300

Ser Asp Ile Ala Val Glu Trp Glu Ser Ser Gly Gln Pro Glu Asn Asn
305 310 315 320

Tyr Asn Thr Thr Pro Pro Met Leu Asp Ser Asp Gly Ser Phe Phe Leu
325 330 335

Tyr Ser Lys Leu Thr Val Asp Lys Ser Arg Trp Gln Gln Gly Asn Ile
340 345 350

Phe Ser Cys Ser Val Met His Glu Ala Leu His Asn Arg Phe Thr Gln
355 360 365

Lys Ser Leu Ser Leu Ser Pro Gly Lys
370 375

<210> 29
<211> 327
<212> PRT
<213> *Homo sapiens*
<400> 29

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

-continued

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> 30
<211> 332
<212> PRT
<213> Artificial Sequence
<220>
<223> Heavy chain constant region
<400> 30
Ala Ser Ala Lys Thr Thr Ala Pro Ser Val Tyr Pro Leu Ala Pro Val
  1               5                  10                  15

Cys Gly Asp Thr Thr Gly Ser Ser Val Thr Leu Gly Cys Leu Val Lys
             20                  25                  30

Gly Tyr Phe Pro Glu Pro Val Thr Leu Thr Trp Asn Ser Gly Ser Leu
         35                  40                  45

Ser Ser Gly Val His Thr Phe Pro Ala Val Leu Gln Ser Asp Leu Tyr
     50                  55                  60

Thr Leu Ser Ser Ser Val Thr Val Thr Ser Ser Thr Trp Pro Ser Gln
 65                  70                  75                  80

Ser Ile Thr Cys Asn Val Ala His Pro Ala Ser Ser Thr Lys Val Asp
                 85                  90                  95

Lys Lys Ile Glu Pro Arg Gly Pro Thr Ile Lys Pro Cys Pro Pro Cys
            100                 105                 110

Lys Cys Pro Ala Pro Asn Leu Leu Gly Gly Pro Ser Val Phe Ile Phe
        115                 120                 125

Pro Pro Lys Ile Lys Asp Val Leu Met Ile Ser Leu Ser Pro Ile Val
    130                 135                 140

Thr Cys Val Val Val Asp Val Ser Glu Asp Asp Pro Asp Val Gln Ile
145                 150                 155                 160

Ser Trp Phe Val Asn Asn Val Glu Val His Thr Ala Gln Thr Gln Thr
                165                 170                 175

His Arg Glu Asp Tyr Asn Ser Thr Leu Arg Val Val Ser Ala Leu Pro
            180                 185                 190

Ile Gln His Gln Asp Trp Met Ser Gly Lys Glu Phe Lys Cys Lys Val
        195                 200                 205
```

-continued

```
Asn Asn Lys Asp Leu Pro Ala Pro Ile Glu Arg Thr Ile Ser Lys Pro
    210                 215                 220

Lys Gly Ser Val Arg Ala Pro Gln Val Tyr Val Leu Pro Pro Pro Glu
225                 230                 235                 240

Glu Glu Met Thr Lys Lys Gln Val Thr Leu Thr Cys Met Val Thr Asp
                245                 250                 255

Phe Met Pro Glu Asp Ile Tyr Val Glu Trp Thr Asn Asn Gly Lys Thr
            260                 265                 270

Glu Leu Asn Tyr Lys Asn Thr Glu Pro Val Leu Asp Ser Asp Gly Ser
        275                 280                 285

Tyr Phe Met Tyr Ser Lys Leu Arg Val Glu Lys Lys Asn Trp Val Glu
    290                 295                 300

Arg Asn Ser Tyr Ser Cys Ser Val Val His Glu Gly Leu His Asn His
305                 310                 315                 320

His Thr Thr Lys Ser Phe Ser Arg Thr Pro Gly Lys
                325                 330

<210> 31
<211> 107
<212> PRT
<213> Artificial Sequence
<220>
<223> Light chain constant region
<400> 31
Arg Thr Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> 32
<211> 245
<212> PRT
<213> Artificial Sequence
<220>
<223> Hybrid Fc Heavy region
<400> 32
Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

*1748
Thr Tyr Arg Val Val Ser Val Leu Thr Val Leu His Gln Asp Trp Leu
            100                 105                 110
```

-continued

```
Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245
```

<210> 33
<211> 990
<212> DNA
<213> *Homo sapiens*
<400> 33

```
gctagcacca agggcccatc ggtcttcccc ctggcgccct cctccaagag cacctctggg   60

ggcacagcgg ccctgggctg cctggtcaag gactacttcc ccgaaccggt gacggtgtcg  120

tggaactcag gggccctgac cagcggcgtg cacaccttcc cggctgtcct acagtcctca  180

ggactctact ccctcagcag cgtggtgacc gtgccctcca gcagcctggg cacccagacc  240

tacatctgca acgtgaatca caagcccagc aacaccaagg tggacaagaa agttgagccc  300

aaatcttgtg acaaaactca cacatgccca ccgtgcccag cacctgaact cctgggggga  360

ccgtcagtct tcctcttccc cccaaaaccc aaggacaccc tcatgatctc ccggacccct  420

gaggtcacat gcgtggtggt ggacgtgagc cacgaagacc ctgaggtcaa gttcaactgg  480

tacgtggacg gcgtggaggt gcataatgcc aagacaaagc cgcgggagga gcagtacaac  540

agcacgtacc gtgtggtcag cgtcctcacc gtcctgcacc aggactggct gaatggcaag  600

gagtacaagt gcaaggtctc caacaaagcc ctcccagccc ccatcgagaa aaccatctcc  660

aaagccaaag ggcagccccg agaaccacag gtgtacaccc tgcccccatc ccgggaggag  720

atgaccaaga accaggtcag cctgacctgc ctggtcaaag gcttctatcc cagcgacatc  780

gccgtggagt gggagagcaa tgggcagccg gagaacaact acaagaccac gcctcccgtg  840

ctggactccg acggctcctt cttcctctac agcaagctca ccgtggacaa gagcaggtgg  900

cagcagggga acgtcttctc atgctccgtg atgcatgagg ctctgcacaa ccactacacg  960

cagaagagcc tctccctgtc tccgggtaaa                                    990
```

<210> 34
<211> 321
<212> DNA
<213> *Homo sapiens*
<400> 34

```
agatctgtgg ctgcaccatc tgtcttcatc ttcccgccat ctgatgagca gttgaaatct   60

ggaactgcct ctgttgtgtg cctgctgaat aacttctatc ccagagaggc caaagtacag  120

tggaaggtgg ataacgccct ccaatcgggt aactcccagg agagtgtcac agagcaggac  180

agcaaggaca gcacctacag cctcagcagc accctgacgc tgagcaaagc agactacgag  240

aaacacaaag tctacgcctg cgaagtcacc catcagggcc tgagctcgcc cgtcacaaag  300
```

```
agcttcaaca ggggagagtg t                                            321

<210> 35
<211> 999
<212> DNA
<213> Artificial Sequence
<220>
<223> Heavy chain constant region
<400> 35
gctagcgcca aaacaacagc cccctccgta tacccccctag cccccgtatg cggcgacacc   60

accggctcct ccgtaaccct aggctgccta gtaaaaggct acttccccga acccgtaacc  120

ctaacctgga actccggctc cctatcctcc ggcgtacaca ccttccccgc cgtactacaa  180

tccgacctat acaccctatc ctcctccgta accgtaacct cctccacctg gccctcccaa  240

tccatcacct gcaacgtagc ccaccccgcc tcctccacca aagtagacaa aaaaatcgag  300

ccaaggggcc ccaccatcaa gccttgccct ccctgcaagt gccctgcccc caacctgctg  360

ggcggcccct ccgtgttcat cttccctcca aagatcaagg acgtgctgat gatctccctg  420

agccccatcg tgacctgcgt ggtggtggac gtgtccgagg acgaccctga cgtgcagatc  480

agctggttcg tgaacaacgt ggaggtgcac accgcccaga cccagaccca cagagaggac  540

tacaactcca ccctgagggt ggtgagcgcc ctgccaatcc agcaccagga ctggatgtcc  600

ggcaaggagt tcaagtgcaa ggtgaacaac aaggacctgc cagccccaat cgagaggacc  660

atcagcaagc ctaagggctc cgtgagggcc ccccaggtgt acgtgctgcc ccctcctgag  720

gaggagatga ccaagaagca ggtgaccctg acctgcatgg tgaccgactt catgcctgag  780

gacatctacg tggagtggac caacaacggc aagaccgagc tgaactacaa gaacaccgag  840

cctgtgctgg acagcgacgg cagctacttc atgtacagca agctgagggt ggagaagaag  900

aactgggtgg agagaaactc ctactcctgc tccgtggtgc acgagggcct gcacaaccac  960

cacaccacca agagcttctc cagaaccccc gggaagtga                         999

<210> 36
<211> 321
<212> DNA
<213> Artificial Sequence
<220>
<223> Light chain constant region
<400> 36
cgtacggatg ctgcaccaac tgtatccatc ttcccaccat ccagtgagca gttaacatct   60

ggaggtgcct cagtcgtgtg cttcttgaac aacttctacc ccaaagacat caatgtcaag  120

tggaagattg atggcagtga acgacaaaat ggcgtcctga acagttggac tgatcaggac  180

agcaaagaca gcacctacag catgagcagc accctcacgt tgaccaagga cgagtatgaa  240

cgacataaca gctatacctg tgaggccact cacaagacat caacttcacc cattgtcaag  300

agcttcaaca ggaatgagtg t                                            321

<210> 37
<211> 457
<212> PRT
<213> Artificial Sequence
<220>
<223> Heavy chain
<400> 37
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ile Ser Asn Cys His Leu Gly Val Cys Tyr Tyr Ser Asn
            100                 105                 110

Gly Met Asp Val Trp Gly Gln Gly Thr Leu Val Thr Val Ser Ser Ala
        115                 120                 125

Lys Thr Thr Ala Pro Ser Val Tyr Pro Leu Ala Pro Val Cys Gly Asp
    130                 135                 140

Thr Thr Gly Ser Ser Val Thr Leu Gly Cys Leu Val Lys Gly Tyr Phe
145                 150                 155                 160

Pro Glu Pro Val Thr Leu Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Thr Ser Ser Thr Trp Pro Ser Gln Ser Ile Thr
        195                 200                 205

Cys Asn Val Ala His Pro Ala Ser Ser Thr Lys Val Asp Lys Lys Ile
    210                 215                 220

Glu Pro Arg Gly Pro Thr Ile Lys Pro Cys Pro Pro Cys Lys Cys Pro
225                 230                 235                 240

Ala Pro Asn Leu Leu Gly Gly Pro Ser Val Phe Ile Phe Pro Pro Lys
                245                 250                 255

Ile Lys Asp Val Leu Met Ile Ser Leu Ser Pro Ile Val Thr Cys Val
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Asn Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
            340                 345                 350

Val Arg Ala Pro Gln Val Tyr Val Leu Pro Pro Pro Glu Glu Glu Met
        355                 360                 365

Thr Lys Lys Gln Val Thr Leu Thr Cys Met Val Thr Asp Phe Met Pro
    370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
                405                 410                 415

Tyr Ser Lys Leu Arg Val Glu Lys Lys Asn Trp Val Glu Arg Asn Ser
            420                 425                 430

Tyr Ser Cys Ser Val Val His Glu Gly Leu His Asn His His Thr Thr
        435                 440                 445

Lys Ser Phe Ser Arg Thr Pro Gly Lys
    450                 455
```

<210> 38
<211> 457
<212> PRT
<213> Artificial Sequence
<220>

-continued

<223> Heavy chain
*2013
<400> 38
Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Val Ile Ser His Gly Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Ile Ser Asn Cys His Leu Gly Val Cys Tyr Tyr Ser Asn
100 105 110

Gly Met Asp Val Trp Gly Gln Gly Thr Leu Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Leu Leu Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Asp Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

Pro Arg Glu Pro Gln Val Tyr Thr Leu Pro Pro Ser Arg Glu Glu Met
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

-continued

```
Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> 39
<211> 218
<212> PRT
<213> Artificial Sequence
<220>
<223> Light chain
*2111
<400> 39
Gln Leu Val Leu Thr Gln Pro Pro Ser Val Ser Ala Ala Pro Gly Gln
  1               5                  10                  15

Arg Val Ser Ile Ser Cys Ser Gly Ser Ser Ser Asn Ile Gly Asp Asn
             20                  25                  30

Tyr Val Ser Trp Tyr Gln Gln Val Pro Gly Ser Ala Pro Lys Leu Leu
          35                  40                  45

Ile Tyr Asp Asn Asn Lys Arg Pro Ser Gly Ile Pro Asp Arg Phe Ser
     50                  55                  60

Ala Ser Lys Ser Gly Thr Ser Ala Thr Leu Gly Ile Thr Gly Leu Gln
 65                  70                  75                  80

Thr Gly Asp Glu Ala Asp Tyr Tyr Cys Ala Thr Trp Asp Gly Ser Leu
                 85                  90                  95

Ser Ala Gly Arg Val Phe Gly Gly Gly Thr Lys Leu Thr Val Leu Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
         195                 200                 205

Ile Val Lys Ser Phe Asn Arg Asn Glu Cys
    210                 215

<210> 40
*2158<211> 218
<212> PRT
<213> Artificial Sequence
<220>
<223> Light chain
<400> 40
Gln Leu Val Leu Thr Gln Pro Pro Ser Val Ser Ala Ala Pro Gly Gln
  1               5                  10                  15

Arg Val Ser Ile Ser Cys Ser Gly Ser Ser Ser Asn Ile Gly Asp Asn
             20                  25                  30

Tyr Val Ser Trp Tyr Gln Gln Val Pro Gly Ser Ala Pro Lys Leu Leu
          35                  40                  45

Ile Tyr Asp Asn Asn Lys Arg Pro Ser Gly Ile Pro Asp Arg Phe Ser
     50                  55                  60

Ala Ser Lys Ser Gly Thr Ser Ala Thr Leu Gly Ile Thr Gly Leu Gln
 65                  70                  75                  80
```

-continued

```
Thr Gly Asp Glu Ala Asp Tyr Tyr Cys Ala Thr Trp Asp Gly Ser Leu
                85                  90                  95

Ser Ala Gly Arg Val Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> 41
<211> 1380
<212> DNA
<213> Artificial Sequence
<220>
<223> Heavy chain
<400> 41

```
gaagttcagc tgcttgagtc tggcggagga ctggttcaac ctggcggaag cctgagactg   60

tcttgtgccg ccagcggctt caccttcagc aactacgcca tgagctgggt ccgacaggcc  120

cctggaaaag gccttgaatg ggtgtccgtg atctctcacg gcggaggcag cacctactac  180

gccgattctg tgaagggcag attcaccatc agccgggaca acagcaagaa caccctgtac  240

ctgcagatga acagcctgag agccgaggac accgccgtgt actattgcgc cagagtgatc  300

agcaactgcc acctgggcgt gtgctactac agcaacggca tggatgtgtg gggccagggc  360

acactggtta ccgttagttc tgctagcgcc aaaacaacag ccccctccgt ataccccccta  420

gcccccgtat gcggcgacac caccggctcc tccgtaaccc taggctgcct agtaaaaggc  480

tacttccccg aacccgtaac cctaacctgg aactccggct ccctatcctc cggcgtacac  540

accttccccg ccgtactaca atccgaccta tacaccctat cctcctccgt aaccgtaacc  600

tcctccacct ggccctccca atccatcacc tgcaacgtag cccaccccgc ctcctccacc  660

aaagtagaca aaaaaatcga gccaaggggc cccaccatca agccttgccc tccctgcaag  720

tgccctgccc ccaacctgct gggcggcccc tccgtgttca tcttccctcc aaagatcaag  780

gacgtgctga tgatctccct gagccccatc gtgacctgcg tggtggtgga cgtgtccgag  840

gacgaccctg acgtgcagat cagctggttc gtgaacaacg tggaggtgca caccgcccag  900

acccagaccc acagagagga ctacaactcc accctgaggg tggtgagcgc cctgccaatc  960

cagcaccagg actggatgtc cggcaaggag ttcaagtgca aggtgaacaa caaggacctg 1020

ccagccccaa tcgagaggac catcagcaag cctaagggct ccgtgagggc cccccaggtg 1080

tacgtgctgc cccctcctga ggaggagatg accaagaagc aggtgaccct gacctgcatg 1140

gtgaccgact tcatgcctga ggacatctac gtggagtgga ccaacaacgg caagaccgag 1200

ctgaactaca agaacaccga gcctgtgctg gacagcgacg gcagctactt catgtacagc 1260

aagctgaggg tggagaagaa gaactgggtg gagagaaact cctactcctg ctccgtggtg 1320

cacgagggcc tgcacaacca ccacaccacc aagagcttct ccagaacccc cgggaagtga 1380
1380
```

-continued

<210> 42
<211> 1371
<212> DNA
<213> Artificial Sequence
<220>
<223> Heavy chain
<400> 42

```
gaagttcagc tgcttgagtc tggcggagga ctggttcaac ctggcggaag cctgagactg   60
tcttgtgccg ccagcggctt caccttcagc aactacgcca tgagctgggt ccgacaggcc  120
cctggaaaag gccttgaatg ggtgtccgtg atctctcacg gcggaggcag cacctactac  180
gccgattctg tgaagggcag attcaccatc agccgggaca acagcaagaa caccctgtac  240
ctgcagatga acagcctgag agccgaggac accgccgtgt actattgcgc cagagtgatc  300
agcaactgcc acctgggcgt gtgctactac agcaacggca tggatgtgtg gggccagggc  360
acactggtta ccgttagttc tgctagcacc aagggcccat cggtcttccc cctggcgccc  420
tcctccaaga gcacctctgg gggcacagcg gccctgggct gcctggtcaa ggactacttc  480
cccgaaccgg tgacggtgtc gtggaactca ggggccctga ccagcggcgt gcacaccttc  540
ccggctgtcc tacagtcctc aggactctac tccctcagca gcgtggtgac cgtgccctcc  600
agcagcctgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc 1020
cccatcgaga aaaccatctc caaagccaaa gggcagcccc gagaaccaca ggtgtacacc 1080
ctgcccccat cccgggagga gatgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta cagcaagctc 1260
accgtggaca agagcaggtg gcagcagggg aacgtcttct catgctccgt gatgcatgag 1320
gctctgcaca accactacac gcagaagagc ctctccctgt ctccgggtaa a          1371
```

<210> 43
<211> 654
<212> DNA
<213> Artificial Sequence
<220>
<223> Light chain
<400> 43

```
caactggttc tgacacagcc tccaagcgtg tcagctgccc ctggacagag agtgtccatc   60
agctgtagcg gcagcagcag caacatcggc gacaactacg tgtcctggta tcagcaggtc  120
ccaggctctg cccctaagct gctgatctac gacaacaaca agcggcccag cggcatcccc  180
gatagatttt ctgccagcaa gagcggcacc agcgccacac tgggaattac aggactgcag  240
acaggcgacg aggccgacta ctattgtgcc acatgggatg gctccctgag cgccggaaga  300
gtttttggcg gaggcaccaa gctgaccgtg cttcgtacgg atgctgcacc aactgtatcc  360
atcttcccac catccagtga gcagttaaca tctggaggtg cctcagtcgt gtgcttcttg  420
aacaacttct accccaaaga catcaatgtc aagtggaaga ttgatggcag tgaacgacaa  480
aatggcgtcc tgaacagttg gactgatcag gacagcaaag acagcaccta cagcatgagc  540
agcaccctca cgttgaccaa ggacgagtat gaacgacata acagctatac ctgtgaggcc  600
actcacaaga catcaacttc acccattgtc aagagcttca acaggaatga gtgt        654
```

<210> 44
<211> 654
<212> DNA
<213> Artificial Sequence
<220>
<223> Light chain
<400> 44
caactggttc tgacacagcc tccaagcgtg tcagctgccc ctggacagag agtgtccatc 60
agctgtagcg gcagcagcag caacatcggc gacaactacg tgtcctggta tcagcaggtc 120
ccaggctctg cccctaagct gctgatctac gacaacaaca agcggcccag cggcatcccc 180
gatagatttt ctgccagcaa gagcggcacc agcgccacac tgggaattac aggactgcag 240
acaggcgacg aggccgacta ctattgtgcc acatgggatg gctccctgag cgccggaaga 300
gtttttggcg gaggcaccaa gctgaccgtg cttagatctg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

<210> 45
<211> 24
<212> DNA
<213> Artificial Sequence
<220>
<223> mouse Lrig-1 forward primer
<400> 45
gacggaattc agtgaggaga acct 24

<210> 46
<211> 24
<212> DNA
<213> Artificial Sequence
<220>
<223> mouse Lrig-1 reverse primer
<400> 46
caactggtag tggcagcttg tagg 24

<210> 47
<211> 24
<212> DNA
<213> Artificial Sequence
<220>
<223> mouse Lrig-2 forward primer
<400> 47
tcacaaggaa cattgtctga acca 24

<210> 48
<211> 24
<212> DNA
<213> Artificial Sequence
<220>
<223> mouse Lrig-2 reverse primer
<400> 48
gcctgatcta acacatcctc ctca 24

<210> 49
<211> 24
<212> DNA
<213> Artificial Sequence
<220>
<223> mouse Lrig-3 forward primer
<400> 49
cagcaccttg agctgaacag aaac 24

<210> 50
<211> 24
<212> DNA
<213> Artificial Sequence
<220>
<223> mouse Lrig-3 reverse primer -continued

```
<400> 50
ccagcctttg gtaatctcgg ttag                                        24

<210> 51
<211> 24
<212> DNA
<213> Artificial Sequence
<220>
<223> mouse FOXP3 forward primer
<400> 51
ctttcaccta tcccaccctt atcc                                        24

<210> 52
<211> 24
<212> DNA
<213> Artificial Sequence
<220>
<223> mouse FOXP3 reverse primer
<400> 52
attcatctac ggtccacact gctc                                        24

<210> 53
<211> 20
<212> DNA
<213> Artificial Sequence
<220>
<223> ACTG1 forward primer
<400> 53
ggcgtcatgg tgggcatggg                                             20

<210> 54
<211> 20
<212> DNA
<213> Artificial Sequence
<220>
<223> ACTG1 reverse primer
<400> 54
atggcgtggg gaagggcgta                                             20
```

SEQUENCE LISTING

```
<160> NUMBER OF SEQ ID NOS: 56

<210> SEQ ID NO 1
<211> LENGTH: 759
<212> TYPE: PRT
<213> ORGANISM: Homo sapiens

<400> SEQUENCE: 1

Gly Pro Arg Ala Pro Cys Ala Ala Ala Cys Thr Cys Ala Gly Asp Ser
1               5                   10                  15

Leu Asp Cys Gly Gly Arg Gly Leu Ala Ala Leu Pro Gly Asp Leu Pro
            20                  25                  30

Ser Trp Thr Arg Ser Leu Asn Leu Ser Tyr Asn Lys Leu Ser Glu Ile
        35                  40                  45

Asp Pro Ala Gly Phe Glu Asp Leu Pro Asn Leu Gln Glu Val Tyr Leu
    50                  55                  60

Asn Asn Asn Glu Leu Thr Ala Val Pro Ser Leu Gly Ala Ala Ser Ser
65                  70                  75                  80

His Val Val Ser Leu Phe Leu Gln His Asn Lys Ile Arg Ser Val Glu
                85                  90                  95

Gly Ser Gln Leu Lys Ala Tyr Leu Ser Leu Glu Val Leu Asp Leu Ser
            100                 105                 110

Leu Asn Asn Ile Thr Glu Val Arg Asn Thr Cys Phe Pro His Gly Pro
        115                 120                 125

Pro Ile Lys Glu Leu Asn Leu Ala Gly Asn Arg Ile Gly Thr Leu Glu
    130                 135                 140
```

```
Leu Gly Ala Phe Asp Gly Leu Ser Arg Ser Leu Leu Thr Leu Arg Leu
145                 150                 155                 160

Ser Lys Asn Arg Ile Thr Gln Leu Pro Val Arg Ala Phe Lys Leu Pro
                165                 170                 175

Arg Leu Thr Gln Leu Asp Leu Asn Arg Asn Arg Ile Arg Leu Ile Glu
            180                 185                 190

Gly Leu Thr Phe Gln Gly Leu Asn Ser Leu Glu Val Leu Lys Leu Gln
        195                 200                 205

Arg Asn Asn Ile Ser Lys Leu Thr Asp Gly Ala Phe Trp Gly Leu Ser
    210                 215                 220

Lys Met His Val Leu His Leu Glu Tyr Asn Ser Leu Val Glu Val Asn
225                 230                 235                 240

Ser Gly Ser Leu Tyr Gly Leu Thr Ala Leu His Gln Leu His Leu Ser
                245                 250                 255

Asn Asn Ser Ile Ala Arg Ile His Arg Lys Gly Trp Ser Phe Cys Gln
            260                 265                 270

Lys Leu His Glu Leu Val Leu Ser Phe Asn Asn Leu Thr Arg Leu Asp
        275                 280                 285

Glu Glu Ser Leu Ala Glu Leu Ser Ser Leu Ser Val Leu Arg Leu Ser
    290                 295                 300

His Asn Ser Ile Ser His Ile Ala Glu Gly Ala Phe Lys Gly Leu Arg
305                 310                 315                 320

Ser Leu Arg Val Leu Asp Leu Asp His Asn Glu Ile Ser Gly Thr Ile
                325                 330                 335

Glu Asp Thr Ser Gly Ala Phe Ser Gly Leu Asp Ser Leu Ser Lys Leu
            340                 345                 350

Thr Leu Phe Gly Asn Lys Ile Lys Ser Val Ala Lys Arg Ala Phe Ser
        355                 360                 365

Gly Leu Glu Gly Leu Glu His Leu Asn Leu Gly Gly Asn Ala Ile Arg
    370                 375                 380

Ser Val Gln Phe Asp Ala Phe Val Lys Met Lys Asn Leu Lys Glu Leu
385                 390                 395                 400

His Ile Ser Ser Asp Ser Phe Leu Cys Asp Cys Gln Leu Lys Trp Leu
                405                 410                 415

Pro Pro Trp Leu Ile Gly Arg Met Leu Gln Ala Phe Val Thr Ala Thr
            420                 425                 430

Cys Ala His Pro Glu Ser Leu Lys Gly Gln Ser Ile Phe Ser Val Pro
        435                 440                 445

Pro Glu Ser Phe Val Cys Asp Asp Phe Leu Lys Pro Gln Ile Ile Thr
    450                 455                 460

Gln Pro Glu Thr Thr Met Ala Met Val Gly Lys Asp Ile Arg Phe Thr
465                 470                 475                 480

Cys Ser Ala Ala Ser Ser Ser Ser Ser Pro Met Thr Phe Ala Trp Lys
                485                 490                 495

Lys Asp Asn Glu Val Leu Thr Asn Ala Asp Met Glu Asn Phe Val His
            500                 505                 510

Val His Ala Gln Asp Gly Glu Val Met Glu Tyr Thr Thr Ile Leu His
        515                 520                 525

Leu Arg Gln Val Thr Phe Gly His Glu Gly Arg Tyr Gln Cys Val Ile
    530                 535                 540

Thr Asn His Phe Gly Ser Thr Tyr Ser His Lys Ala Arg Leu Thr Val
545                 550                 555                 560
```

```
Asn Val Leu Pro Ser Phe Thr Lys Thr Pro His Asp Ile Thr Ile Arg
                565                 570                 575

Thr Thr Thr Val Ala Arg Leu Glu Cys Ala Ala Thr Gly His Pro Asn
            580                 585                 590

Pro Gln Ile Ala Trp Gln Lys Asp Gly Gly Thr Asp Phe Pro Ala Ala
        595                 600                 605

Arg Glu Arg Arg Met His Val Met Pro Asp Asp Asp Val Phe Phe Ile
    610                 615                 620

Thr Asp Val Lys Ile Asp Asp Ala Gly Val Tyr Ser Cys Thr Ala Gln
625                 630                 635                 640

Asn Ser Ala Gly Ser Ile Ser Ala Asn Ala Thr Leu Thr Val Leu Glu
                645                 650                 655

Thr Pro Ser Leu Val Val Pro Leu Glu Asp Arg Val Val Ser Val Gly
            660                 665                 670

Glu Thr Val Ala Leu Gln Cys Lys Ala Thr Gly Asn Pro Pro Pro Arg
        675                 680                 685

Ile Thr Trp Phe Lys Gly Asp Arg Pro Leu Ser Leu Thr Glu Arg His
    690                 695                 700

His Leu Thr Pro Asp Asn Gln Leu Leu Val Val Gln Asn Val Val Ala
705                 710                 715                 720

Glu Asp Ala Gly Arg Tyr Thr Cys Glu Met Ser Asn Thr Leu Gly Thr
                725                 730                 735

Glu Arg Ala His Ser Gln Leu Ser Val Leu Pro Ala Ala Gly Cys Arg
            740                 745                 750

Lys Asp Gly Thr Thr Val Gly
        755
```

<210> SEQ ID NO 2
<211> LENGTH: 2397
<212> TYPE: DNA
<213> ORGANISM: Homo sapiens

<400> SEQUENCE: 2

```
ggcccgcggg cgccctgcgc ggccgcctgc acttgcgctg gggactcgct ggactgcggt     60

gggcgcgggc tggctgcgtt gcccggggac ctgccctcct ggacgcggag cctaaacctg    120

agttacaaca aactctctga gattgaccct gctggttttg aggacttgcc gaacctacag    180

gaagtgtacc tcaataataa tgagttgaca gcggtaccat ccctgggcgc tgcttcatca    240

catgtcgtct ctctctttct gcagcacaac aagattcgca gcgtggaggg gagccagctg    300

aaggcctacc tttccttaga agtgttagat ctgagtttga acaacatcac ggaagtgcgg    360

aacacctgct ttccacacgg accgcctata aaggagctca acctggcagg caatcggatt    420

ggcaccctgg agttgggagc atttgatggt ctgtcacggt cgctgctaac tcttcgcctg    480

agcaaaaaca ggatcaccca gcttcctgta agagcattca agctacccag gctgacacaa    540

ctggacctca atcggaacag gattcggctg atagagggcc tcaccttcca ggggctcaac    600

agcttggagg tgctgaagct tcagcgaaac aacatcagca aactgacaga tggggccttc    660

tggggactgt ccaagatgca tgtgctgcac ctggagtaca acagcctggt agaagtgaac    720

agcggctcgc tctacggcct cacggccctg catcagctcc acctcagcaa caattccatc    780

gctcgcattc accgcaaggg ctggagcttc tgccagaagc tgcatgagtt ggtcctgtcc    840

ttcaacaacc tgacacggct ggacgaggag agcctggccg agctgagcag cctgagtgtc    900

ctgcgtctca gccacaattc catcagccac attgcggagg gtgccttcaa gggactcagg    960
```

-continued

```
agcctgcgag tcttggatct ggaccataac gagatttcgg gcacaataga ggacacgagc   1020

ggcgccttct cagggctcga cagcctcagc aagctgactc tgtttggaaa caagatcaag   1080

tctgtggcta agagagcatt ctcggggctg gaaggcctgg agcacctgaa ccttggaggg   1140

aatgcgatca gatctgtcca gtttgatgcc tttgtgaaga tgaagaatct taaagagctc   1200

catatcagca gcgacagctt cctgtgtgac tgccagctga agtggctgcc cccgtggcta   1260

attggcagga tgctgcaggc ctttgtgaca gccacctgtg cccacccaga atcactgaag   1320

ggtcagagca ttttctctgt gccaccagag agtttcgtgt gcgatgactt cctgaagcca   1380

cagatcatca cccagccaga aaccaccatg gctatggtgg gcaaggacat ccggtttaca   1440

tgctcagcag ccagcagcag cagctccccc atgacctttg cctggaagaa agacaatgaa   1500

gtcctgacca atgcagacat ggagaacttt gtccacgtcc acgcgcagga cggggaagtg   1560

atggagtaca ccaccatcct gcacctccgt caggtcactt tcgggcacga gggccgctac   1620

caatgtgtca tcaccaacca ctttggctcc acctattcac ataaggccag gctcaccgtg   1680

aatgtgttgc catcattcac caaaacgccc cacgacataa ccatccggac caccaccgtg   1740

gcccgcctcg aatgtgctgc cacaggtcac ccaaaccctc agattgcctg gcagaaggat   1800

ggaggcacgg atttccccgc tgcccgtgag cgacgcatgc atgtcatgcc ggatgacgac   1860

gtgtttttca tcactgatgt gaaaatagat gacgcagggg tttacagctg tactgctcag   1920

aactcagccg gttctatttc agctaatgcc accctgactg tcctagagac cccatccttg   1980

gtggtcccct tggaagaccg tgtggtatct gtgggagaaa cagtggccct ccaatgcaaa   2040

gccacgggga accctccgcc ccgcatcacc tggttcaagg gggaccgccc gctgagcctc   2100

actgagcggc accacctgac ccctgacaac cagctcctgg tggttcagaa cgtggtggca   2160

gaggatgcgg gccgatatac ctgtgagatg tccaacaccc tgggcacgga gcgagctcac   2220

agccagctga gcgtcctgcc cgcagcaggc tgcaggaagg atgggaccac ggtaggcatc   2280

ttcaccattg ctgtcgtgag cagcatcgtc ctgacgtcac tggtctgggt gtgcatcatc   2340

taccagacca ggaagaagag tgaagagtac agtgtcacca acacagatga aaccgtc      2397
```

<210> SEQ ID NO 3
<211> LENGTH: 761
<212> TYPE: PRT
<213> ORGANISM: Mus musculus

<400> SEQUENCE: 3

```
Gln Ala Gly Pro Arg Ala Pro Cys Ala Ala Ala Cys Thr Cys Ala Gly
1               5                   10                  15

Asp Ser Leu Asp Cys Ser Gly Arg Gly Leu Ala Thr Leu Pro Arg Asp
            20                  25                  30

Leu Pro Ser Trp Thr Arg Ser Leu Asn Leu Ser Tyr Asn Arg Leu Ser
        35                  40                  45

Glu Ile Asp Ser Ala Ala Phe Glu Asp Leu Thr Asn Leu Gln Glu Val
    50                  55                  60

Tyr Leu Asn Ser Asn Glu Leu Thr Ala Ile Pro Ser Leu Gly Ala Ala
65                  70                  75                  80

Ser Ile Gly Val Val Ser Leu Phe Leu Gln His Asn Lys Ile Leu Ser
                85                  90                  95

Val Asp Gly Ser Gln Leu Lys Ser Tyr Leu Ser Leu Glu Val Leu Asp
            100                 105                 110

Leu Ser Ser Asn Asn Ile Thr Glu Ile Arg Ser Ser Cys Phe Pro Asn
        115                 120                 125
```

```
Gly Leu Arg Ile Arg Glu Leu Asn Leu Ala Ser Asn Arg Ile Ser Ile
    130                 135                 140

Leu Glu Ser Gly Ala Phe Asp Gly Leu Ser Arg Ser Leu Leu Thr Leu
145                 150                 155                 160

Arg Leu Ser Lys Asn Arg Ile Thr Gln Leu Pro Val Lys Ala Phe Lys
                165                 170                 175

Leu Pro Arg Leu Thr Gln Leu Asp Leu Asn Arg Asn Arg Ile Arg Leu
            180                 185                 190

Ile Glu Gly Leu Thr Phe Gln Gly Leu Asp Ser Leu Glu Val Leu Arg
        195                 200                 205

Leu Gln Arg Asn Asn Ile Ser Arg Leu Thr Asp Gly Ala Phe Trp Gly
    210                 215                 220

Leu Ser Lys Met His Val Leu His Leu Glu Tyr Asn Ser Leu Val Glu
225                 230                 235                 240

Val Asn Ser Gly Ser Leu Tyr Gly Leu Thr Ala Leu His Gln Leu His
                245                 250                 255

Leu Ser Asn Asn Ser Ile Ser Arg Ile Gln Arg Asp Gly Trp Ser Phe
            260                 265                 270

Cys Gln Lys Leu His Glu Leu Ile Leu Ser Phe Asn Asn Leu Thr Arg
        275                 280                 285

Leu Asp Glu Glu Ser Leu Ala Glu Leu Ser Ser Leu Ser Ile Leu Arg
    290                 295                 300

Leu Ser His Asn Ala Ile Ser His Ile Ala Glu Gly Ala Phe Lys Gly
305                 310                 315                 320

Leu Lys Ser Leu Arg Val Leu Asp Leu Asp His Asn Glu Ile Ser Gly
                325                 330                 335

Thr Ile Glu Asp Thr Ser Gly Ala Phe Thr Gly Leu Asp Asn Leu Ser
            340                 345                 350

Lys Leu Thr Leu Phe Gly Asn Lys Ile Lys Ser Val Ala Lys Arg Ala
        355                 360                 365

Phe Ser Gly Leu Glu Ser Leu Glu His Leu Asn Leu Gly Glu Asn Ala
    370                 375                 380

Ile Arg Ser Val Gln Phe Asp Ala Phe Ala Lys Met Lys Asn Leu Lys
385                 390                 395                 400

Glu Leu Tyr Ile Ser Ser Glu Ser Phe Leu Cys Asp Cys Gln Leu Lys
                405                 410                 415

Trp Leu Pro Pro Trp Leu Met Gly Arg Met Leu Gln Ala Phe Val Thr
            420                 425                 430

Ala Thr Cys Ala His Pro Glu Ser Leu Lys Gly Gln Ser Ile Phe Ser
        435                 440                 445

Val Leu Pro Asp Ser Phe Val Cys Asp Asp Phe Pro Lys Pro Gln Ile
    450                 455                 460

Ile Thr Gln Pro Glu Thr Thr Met Ala Val Val Gly Lys Asp Ile Arg
465                 470                 475                 480

Phe Thr Cys Ser Ala Ala Ser Ser Ser Ser Ser Pro Met Thr Phe Ala
                485                 490                 495

Trp Lys Lys Asp Asn Glu Val Leu Ala Asn Ala Asp Met Glu Asn Phe
            500                 505                 510

Ala His Val Arg Ala Gln Asp Gly Glu Val Met Glu Tyr Thr Thr Ile
        515                 520                 525

Leu His Leu Arg His Val Thr Phe Gly His Glu Gly Arg Tyr Gln Cys
    530                 535                 540
```

```
Ile Ile Thr Asn His Phe Gly Ser Thr Tyr Ser His Lys Ala Arg Leu
545                 550                 555                 560

Thr Val Asn Val Leu Pro Ser Phe Thr Lys Ile Pro His Asp Ile Ala
                565                 570                 575

Ile Arg Thr Gly Thr Thr Ala Arg Leu Glu Cys Ala Ala Thr Gly His
            580                 585                 590

Pro Asn Pro Gln Ile Ala Trp Gln Lys Asp Gly Gly Thr Asp Phe Pro
        595                 600                 605

Ala Ala Arg Glu Arg Arg Met His Val Met Pro Asp Asp Asp Val Phe
    610                 615                 620

Phe Ile Thr Asp Val Lys Ile Asp Asp Met Gly Val Tyr Ser Cys Thr
625                 630                 635                 640

Ala Gln Asn Ser Ala Gly Ser Val Ser Ala Asn Ala Thr Leu Thr Val
                645                 650                 655

Leu Glu Thr Pro Ser Leu Ala Val Pro Leu Glu Asp Arg Val Val Thr
            660                 665                 670

Val Gly Glu Thr Val Ala Phe Gln Cys Lys Ala Thr Gly Ser Pro Thr
        675                 680                 685

Pro Arg Ile Thr Trp Leu Lys Gly Gly Arg Pro Leu Ser Leu Thr Glu
    690                 695                 700

Arg His His Phe Thr Pro Gly Asn Gln Leu Leu Val Val Gln Asn Val
705                 710                 715                 720

Met Ile Asp Asp Ala Gly Arg Tyr Thr Cys Glu Met Ser Asn Pro Leu
                725                 730                 735

Gly Thr Glu Arg Ala His Ser Gln Leu Ser Ile Leu Pro Thr Pro Gly
            740                 745                 750

Cys Arg Lys Asp Gly Thr Thr Val Gly
        755                 760
```

<210> SEQ ID NO 4
<211> LENGTH: 2283
<212> TYPE: DNA
<213> ORGANISM: Mus musculus

<400> SEQUENCE: 4

```
caggctggcc cgcgggcccc ctgcgcggcc gcctgcactt gcgccgggga ctcgctggac     60

tgcagtgggc gcgggctggc gacgctgccc cgggacctgc cctcctggac gcgcagccta    120

aacctgagtt ataacagact ctccgagatc gactctgctg cttttgagga cttgacgaat    180

ctgcaggaag tgtacctcaa cagcaatgag ctgacagcca taccatcact gggcgctgct    240

tccataggag ttgtctctct ctttttgcag cacaacaaga tccttagtgt ggatgggagc    300

cagctgaagt cgtacctgtc cttggaagtg ctggatctga gttccaacaa catcacggaa    360

attcggagct cctgtttccc gaacggcctg cgtataaggg aactcaactt ggcgagcaac    420

cgcatcagca tcctggagtc tggagcattt gatggtctgt cgcggtcact gctgactctc    480

cgtctgagca aaaacaggat cacccagctt cctgtgaaag cgttcaagct acccaggctg    540

acacaactag acctgaatcg gaatcggatt cggctgattg aaggcctcac gttccagggg    600

ctcgacagct tagaggtgct gaggcttcag aggaacaaca tcagcaggct gacggacggg    660

gccttctggg ggctgtctaa gatgcacgtg ctgcacctgg agtacaacag tctggtggaa    720

gtgaacagtg gctccctcta tggcctcaca gccctgcacc agctgcacct cagcaacaac    780

tccatctctc gaattcagcg tgatggctgg agcttctgcc aaaagctgca tgagttgatt    840

ctgtccttca acaacctcac gcggctggat gaggagagtc tagcggagtt gagcagcctc    900
```

```
agtatcctgc gcctcagtca caacgccatc agtcacattg ctgaaggcgc cttcaaggga    960

ctcaagagtc tgcgggtctt ggacctggac cataacgaga tctcgggtac aatcgaggat   1020

accagtggtg cctttacggg gcttgacaac ctcagcaagc tgactctgtt tggaaacaag   1080

atcaaatctg tggctaagag agccttctcg ggcctggaaa gcctggaaca cctgaacctt   1140

ggagagaatg caatcaggtc tgtccagttt gatgcctttg caaagatgaa gaaccttaaa   1200

gagctctaca tcagcagtga gagcttcctg tgtgactgcc agctcaagtg gctgccccca   1260

tggctaatgg gtaggatgct gcaggccttt gtgacagcca cctgtgccca tccagagtcg   1320

ctgaagggcc agagcatttt ctcagtgctg ccagacagct ttgtgtgtga tgactttcca   1380

aagccacaga tcatcaccca gcctgagacg accatggctg tggtgggcaa ggacatccgt   1440

ttcacatgct ccgcagccag cagcagcagc tcaccaatga ccttcgcctg gaagaaggac   1500

aatgaggtcc tggccaatgc agacatggag aactttgccc acgtccgtgc acaggacggc   1560

gaagtgatgg agtataccac tatcctgcac ctccgtcacg tcacctttgg gcacgagggc   1620

cgctaccagt gtatcatcac aaaccacttt ggctccacat actcccacaa agccaggctc   1680

actgtgaatg tgttgccatc attcactaaa ataccccatg acattgccat ccggactggc   1740

accacagccc gcctcgagtg tgctgccacg ggccacccta accctcagat tgcctggcag   1800

aaggatggag gcaccgattt cccggcagct cgtgagcgac gcatgcatgt tatgccagac   1860

gatgatgtgt tcttcatcac tgatgtgaaa atagacgaca tgggggtcta cagctgcact   1920

gcccagaact cggcaggctc ggtttcagcc aacgctaccc tcacagtctt agaaactcca   1980

tccttggcag tgcctctgga agaccgtgtg gtaactgtgg gagaaacagt ggccttccag   2040

tgcaaagcaa ccgggagccc cacaccacgc atcacctggc ttaagggagg tcgcccattg   2100

agcctcacag agcgccacca tttcactcca ggcaaccagc tgctggttgt tcagaatgtg   2160

atgatagacg atgcagggcg gtatacctgt gagatgtcta atcccctggg cactgagcga   2220

gcacatagcc agctgagcat tttacctacc cctggctgcc ggaaggatgg gaccaccgta   2280

ggc                                                                 2283
```

<210> SEQ ID NO 5
<211> LENGTH: 5
<212> TYPE: PRT
<213> ORGANISM: Artificial Sequence
<220> FEATURE:
<223> OTHER INFORMATION: Heavy chain CDR 1

<400> SEQUENCE: 5

```
Asn Tyr Ala Met Ser
1               5
```

<210> SEQ ID NO 6
<211> LENGTH: 17
<212> TYPE: PRT
<213> ORGANISM: Artificial Sequence
<220> FEATURE:
<223> OTHER INFORMATION: Heavy chain CDR 2

<400> SEQUENCE: 6

```
Val Ile Ser His Gly Gly Gly Ser Thr Tyr Tyr Ala Asp Ser Val Lys
1               5                   10                  15

Gly
```

<210> SEQ ID NO 7

<211> LENGTH: 18
<212> TYPE: PRT
<213> ORGANISM: Artificial Sequence
<220> FEATURE:
<223> OTHER INFORMATION: Heavy chain CDR 3

<400> SEQUENCE: 7

Val Ile Ser Asn Cys His Leu Gly Val Cys Tyr Tyr Ser Asn Gly Met
1 5 10 15

Asp Val

<210> SEQ ID NO 8
<211> LENGTH: 13
<212> TYPE: PRT
<213> ORGANISM: Artificial Sequence
<220> FEATURE:
<223> OTHER INFORMATION: Light chain CDR 1

<400> SEQUENCE: 8

Ser Gly Ser Ser Ser Asn Ile Gly Asp Asn Tyr Val Ser
1 5 10

<210> SEQ ID NO 9
<211> LENGTH: 7
<212> TYPE: PRT
<213> ORGANISM: Artificial Sequence
<220> FEATURE:
<223> OTHER INFORMATION: Light chain CDR 2

<400> SEQUENCE: 9

Asp Asn Asn Lys Arg Pro Ser
1 5

<210> SEQ ID NO 10
<211> LENGTH: 10
<212> TYPE: PRT
<213> ORGANISM: Artificial Sequence
<220> FEATURE:
<223> OTHER INFORMATION: Light chain CDR 3

<400> SEQUENCE: 10

Trp Asp Gly Ser Leu Ser Ala Gly Arg Val
1 5 10

<210> SEQ ID NO 11
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 11

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Val Ile Ser His Gly Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Arg Val Ile Ser Asn Cys His Leu Gly Val Cys Tyr Tyr Ser Asn
            100                 105                 110

Gly Met Asp Val Trp Gly Gln Gly Thr Leu Val Thr Val Ser Ser
        115                 120                 125


<210> SEQ ID NO 12
<211> LENGTH: 111
<212> TYPE: PRT
<213> ORGANISM: Artificial Sequence
<220> FEATURE:
<223> OTHER INFORMATION: Light chain variable region

<400> SEQUENCE: 12

Gln Leu Val Leu Thr Gln Pro Pro Ser Val Ser Ala Ala Pro Gly Gln
1               5                   10                  15

Arg Val Ser Ile Ser Cys Ser Gly Ser Ser Ser Asn Ile Gly Asp Asn
            20                  25                  30

Tyr Val Ser Trp Tyr Gln Gln Val Pro Gly Ser Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Gly Ser Leu
                85                  90                  95

Ser Ala Gly Arg Val Phe Gly Gly Gly Thr Lys Leu Thr Val Leu
            100                 105                 110


<210> SEQ ID NO 13
<211> LENGTH: 15
<212> TYPE: DNA
<213> ORGANISM: Artificial Sequence
<220> FEATURE:
<223> OTHER INFORMATION: Heavy chain CDR 1

<400> SEQUENCE: 13

aactacgcca tgagc                                                   15


<210> SEQ ID NO 14
<211> LENGTH: 51
<212> TYPE: DNA
<213> ORGANISM: Artificial Sequence
<220> FEATURE:
<223> OTHER INFORMATION: Heavy chain CDR 2

<400> SEQUENCE: 14

gtgatctctc acggcggagg cagcacctac tacgccgatt ctgtgaaggg c           51


<210> SEQ ID NO 15
<211> LENGTH: 54
<212> TYPE: DNA
<213> ORGANISM: Artificial Sequence
<220> FEATURE:
<223> OTHER INFORMATION: Heavy chain CDR 3

<400> SEQUENCE: 15

gtgatcagca actgccacct gggcgtgtgc tactacagca acggcatgga tgtg        54


<210> SEQ ID NO 16
<211> LENGTH: 39
<212> TYPE: DNA
<213> ORGANISM: Artificial Sequence
```

<220> FEATURE:
<223> OTHER INFORMATION: Light chain CDR 1

<400> SEQUENCE: 16
agcggcagca gcagcaacat cggcgacaac tacgtgtcc 39

<210> SEQ ID NO 17
<211> LENGTH: 21
<212> TYPE: DNA
<213> ORGANISM: Artificial Sequence
<220> FEATURE:
<223> OTHER INFORMATION: Light chain CDR 2

<400> SEQUENCE: 17
gacaacaaca agcggcccag c 21

<210> SEQ ID NO 18
<211> LENGTH: 30
<212> TYPE: DNA
<213> ORGANISM: Artificial Sequence
<220> FEATURE:
<223> OTHER INFORMATION: Light chain CDR 3

<400> SEQUENCE: 18
tgggatggct ccctgagcgc cggaagagtt 30

<210> SEQ ID NO 19
<211> LENGTH: 381
<212> TYPE: DNA
<213> ORGANISM: Artificial Sequence
<220> FEATURE:
<223> OTHER INFORMATION: Heavy chain variable region

<400> SEQUENCE: 19
gaagttcagc tgcttgagtc tggcggagga ctggttcaac ctggcggaag cctgagactg 60
tcttgtgccg ccagcggctt caccttcagc aactacgcca tgagctgggt ccgacaggcc 120
cctggaaaag gccttgaatg ggtgtccgtg atctctcacg gcggaggcag cacctactac 180
gccgattctg tgaagggcag attcaccatc agccgggaca acagcaagaa caccctgtac 240
ctgcagatga acagcctgag agccgaggac accgccgtgt actattgcgc cagagtgatc 300
agcaactgcc acctgggcgt gtgctactac agcaacggca tggatgtgtg gggccagggc 360
acactggtta ccgttagttc t 381

<210> SEQ ID NO 20
<211> LENGTH: 333
<212> TYPE: DNA
<213> ORGANISM: Artificial Sequence
<220> FEATURE:
<223> OTHER INFORMATION: Light chain variable region

<400> SEQUENCE: 20
caactggttc tgacacagcc tccaagcgtg tcagctgccc ctggacagag agtgtccatc 60
agctgtagcg gcagcagcag caacatcggc gacaactacg tgtcctggta tcagcaggtc 120
ccaggctctg cccctaagct gctgatctac gacaacaaca agcggcccag cggcatcccc 180
gatagatttt ctgccagcaa gagcggcacc agcgccacac tgggaattac aggactgcag 240
acaggcgacg aggccgacta ctattgtgcc acatgggatg gctccctgag cgccggaaga 300
gtttttggcg gaggcaccaa gctgaccgtg ctt 333

<210> SEQ ID NO 21

```
<211> LENGTH: 328
<212> TYPE: PRT
<213> ORGANISM: Mus musculus

<400> SEQUENCE: 21

Thr Thr Ala Pro Ser Val Tyr Pro Leu Ala Pro Val Cys Gly Asp Thr
1               5                   10                  15

Thr Gly Ser Ser Val Thr Leu Gly Cys Leu Val Lys Gly Tyr Phe Pro
            20                  25                  30

Glu Pro Val Thr Leu Thr Trp Asn Ser Gly Ser Leu Ser Ser Gly Val
        35                  40                  45

His Thr Phe Pro Ala Val Leu Gln Ser Asp Leu Tyr Thr Leu Ser Ser
    50                  55                  60

Ser Val Thr Val Thr Ser Ser Thr Trp Pro Ser Gln Ser Ile Thr Cys
65                  70                  75                  80

Asn Val Ala His Pro Ala Ser Ser Thr Lys Val Asp Lys Lys Ile Glu
                85                  90                  95

Pro Arg Gly Pro Thr Ile Lys Pro Cys Pro Pro Cys Lys Cys Pro Ala
            100                 105                 110

Pro Asn Leu Leu Gly Gly Pro Ser Val Phe Ile Phe Pro Pro Lys Ile
        115                 120                 125

Lys Asp Val Leu Met Ile Ser Leu Ser Pro Ile Val Thr Cys Val Val
    130                 135                 140

Val Asp Val Ser Glu Asp Asp Pro Asp Val Gln Ile Ser Trp Phe Val
145                 150                 155                 160

Asn Asn Val Glu Val His Thr Ala Gln Thr Gln Thr His Arg Glu Asp
                165                 170                 175

Tyr Asn Ser Thr Leu Arg Val Val Ser Ala Leu Pro Ile Gln His Gln
            180                 185                 190

Asp Trp Met Ser Gly Lys Glu Phe Lys Cys Lys Val Asn Asn Lys Asp
        195                 200                 205

Leu Pro Ala Pro Ile Glu Arg Thr Ile Ser Lys Pro Lys Gly Ser Val
    210                 215                 220

Arg Ala Pro Gln Val Tyr Val Leu Pro Pro Pro Glu Glu Glu Met Thr
225                 230                 235                 240

Lys Lys Gln Val Thr Leu Thr Cys Met Val Thr Asp Phe Met Pro Glu
                245                 250                 255

Asp Ile Tyr Val Glu Trp Thr Asn Asn Gly Lys Thr Glu Leu Asn Tyr
            260                 265                 270

Lys Asn Thr Glu Pro Val Leu Asp Ser Asp Gly Ser Tyr Phe Met Tyr
        275                 280                 285

Ser Lys Leu Arg Val Glu Lys Lys Asn Trp Val Glu Arg Asn Ser Tyr
    290                 295                 300

Ser Cys Ser Val Val His Glu Gly Leu His Asn His His Thr Thr Lys
305                 310                 315                 320

Ser Phe Ser Arg Thr Pro Gly Lys
                325


<210> SEQ ID NO 22
<211> LENGTH: 107
<212> TYPE: PRT
<213> ORGANISM: Mus musculus

<400> SEQUENCE: 22

Arg Thr Val Ala Ala Pro Thr Val Ser Ile Phe Pro Pro Ser Ser Glu
1               5                   10                  15
```

```
Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 23
<211> LENGTH: 330
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 24
<211> LENGTH: 330
<212> TYPE: PRT
<213> ORGANISM: Homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                 330


<210> SEQ ID NO 25
<211> LENGTH: 107
<212> TYPE: PRT
<213> ORGANISM: Homo sapiens

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 26
<211> LENGTH: 107
<212> TYPE: PRT
<213> ORGANISM: Homo sapiens

<400> SEQUENCE: 26

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 27
<211> LENGTH: 326
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 28
<211> LENGTH: 377
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95
```

```
Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 29
<211> LENGTH: 327
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 30
<211> LENGTH: 332
<212> TYPE: PRT
<213> ORGANISM: Artificial Sequence
<220> FEATURE:
<223> OTHER INFORMATION: Heavy chain constant region

<400> SEQUENCE: 30

Ala Ser Ala Lys Thr Thr Ala Pro Ser Val Tyr Pro Leu Ala Pro Val
1               5                   10                  15

Cys Gly Asp Thr Thr Gly Ser Ser Val Thr Leu Gly Cys Leu Val Lys
            20                  25                  30

Gly Tyr Phe Pro Glu Pro Val Thr Leu Thr Trp Asn Ser Gly Ser Leu
        35                  40                  45

Ser Ser Gly Val His Thr Phe Pro Ala Val Leu Gln Ser Asp Leu Tyr
    50                  55                  60

Thr Leu Ser Ser Ser Val Thr Val Thr Ser Ser Thr Trp Pro Ser Gln
65                  70                  75                  80

Ser Ile Thr Cys Asn Val Ala His Pro Ala Ser Ser Thr Lys Val Asp
                85                  90                  95

Lys Lys Ile Glu Pro Arg Gly Pro Thr Ile Lys Pro Cys Pro Pro Cys
            100                 105                 110

Lys Cys Pro Ala Pro Asn Leu Leu Gly Gly Pro Ser Val Phe Ile Phe
        115                 120                 125
```

```
Pro Pro Lys Ile Lys Asp Val Leu Met Ile Ser Leu Ser Pro Ile Val
    130                 135                 140

Thr Cys Val Val Val Asp Val Ser Glu Asp Asp Pro Asp Val Gln Ile
145                 150                 155                 160

Ser Trp Phe Val Asn Asn Val Glu Val His Thr Ala Gln Thr Gln Thr
                165                 170                 175

His Arg Glu Asp Tyr Asn Ser Thr Leu Arg Val Val Ser Ala Leu Pro
            180                 185                 190

Ile Gln His Gln Asp Trp Met Ser Gly Lys Glu Phe Lys Cys Lys Val
        195                 200                 205

Asn Asn Lys Asp Leu Pro Ala Pro Ile Glu Arg Thr Ile Ser Lys Pro
    210                 215                 220

Lys Gly Ser Val Arg Ala Pro Gln Val Tyr Val Leu Pro Pro Pro Glu
225                 230                 235                 240

Glu Glu Met Thr Lys Lys Gln Val Thr Leu Thr Cys Met Val Thr Asp
                245                 250                 255

Phe Met Pro Glu Asp Ile Tyr Val Glu Trp Thr Asn Asn Gly Lys Thr
            260                 265                 270

Glu Leu Asn Tyr Lys Asn Thr Glu Pro Val Leu Asp Ser Asp Gly Ser
        275                 280                 285

Tyr Phe Met Tyr Ser Lys Leu Arg Val Glu Lys Lys Asn Trp Val Glu
    290                 295                 300

Arg Asn Ser Tyr Ser Cys Ser Val Val His Glu Gly Leu His Asn His
305                 310                 315                 320

His Thr Thr Lys Ser Phe Ser Arg Thr Pro Gly Lys
                325                 330


<210> SEQ ID NO 31
<211> LENGTH: 107
<212> TYPE: PRT
<213> ORGANISM: Artificial Sequence
<220> FEATURE:
<223> OTHER INFORMATION: Light chain constant region

<400> SEQUENCE: 31

Arg Thr Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 32
<211> LENGTH: 245
<212> TYPE: PRT
<213> ORGANISM: Artificial Sequence
<220> FEATURE:
<223> OTHER INFORMATION: Hybrid Fc Heavy region
```

<400> SEQUENCE: 32

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 33
<211> LENGTH: 990
<212> TYPE: DNA
<213> ORGANISM: Homo sapiens

<400> SEQUENCE: 33
gctagcacca agggcccatc ggtcttcccc ctggcgccct cctccaagag cacctctggg 60
ggcacagcgg ccctgggctg cctggtcaag gactacttcc ccgaaccggt gacggtgtcg 120
tggaactcag gggccctgac cagcggcgtg cacaccttcc cggctgtcct acagtcctca 180
ggactctact ccctcagcag cgtggtgacc gtgccctcca gcagcctggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 34
<211> LENGTH: 321
<212> TYPE: DNA
<213> ORGANISM: Homo sapiens

<400> SEQUENCE: 34
agatctgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 35
<211> LENGTH: 999
<212> TYPE: DNA
<213> ORGANISM: Artificial Sequence
<220> FEATURE:
<223> OTHER INFORMATION: Heavy chain constant region

<400> SEQUENCE: 35
gctagcgcca aaacaacagc cccctccgta taccccctag cccccgtatg cggcgacacc 60
accggctcct ccgtaaccct aggctgccta gtaaaaggct acttccccga acccgtaacc 120
ctaacctgga actccggctc cctatcctcc ggcgtacaca ccttccccgc cgtactacaa 180
tccgacctat acaccctatc ctcctccgta accgtaacct cctccacctg gccctcccaa 240
tccatcacct gcaacgtagc ccaccccgcc tcctccacca aagtagacaa aaaaatcgag 300
ccaaggggcc ccaccatcaa gccttgccct ccctgcaagt gccctgcccc caacctgctg 360
ggcggcccct ccgtgttcat cttccctcca aagatcaagg acgtgctgat gatctccctg 420
agccccatcg tgacctgcgt ggtggtggac gtgtccgagg acgaccctga cgtgcagatc 480
agctggttcg tgaacaacgt ggaggtgcac accgcccaga cccagaccca cagagaggac 540
tacaactcca ccctgagggt ggtgagcgcc ctgccaatcc agcaccagga ctggatgtcc 600
ggcaaggagt tcaagtgcaa ggtgaacaac aaggacctgc cagccccaat cgagaggacc 660
atcagcaagc ctaagggctc cgtgagggcc ccccaggtgt acgtgctgcc ccctcctgag 720
gaggagatga ccaagaagca ggtgaccctg acctgcatgg tgaccgactt catgcctgag 780
gacatctacg tggagtggac caacaacggc aagaccgagc tgaactacaa gaacaccgag 840
cctgtgctgg acagcgacgg cagctacttc atgtacagca agctgagggt ggagaagaag 900
aactgggtgg agagaaactc ctactcctgc tccgtggtgc acgagggcct gcacaaccac 960
cacaccacca agagcttctc cagaaccccc gggaagtga 999

<210> SEQ ID NO 36

<211> LENGTH: 321
<212> TYPE: DNA
<213> ORGANISM: Artificial Sequence
<220> FEATURE:
<223> OTHER INFORMATION: Light chain constant region

<400> SEQUENCE: 36
cgtacggatg ctgcaccaac tgtatccatc ttcccaccat ccagtgagca gttaacatct 60
ggaggtgcct cagtcgtgtg cttcttgaac aacttctacc ccaaagacat caatgtcaag 120
tggaagattg atggcagtga acgacaaaat ggcgtcctga acagttggac tgatcaggac 180
agcaaagaca gcacctacag catgagcagc accctcacgt tgaccaagga cgagtatgaa 240
cgacataaca gctatacctg tgaggccact cacaagacat caacttcacc cattgtcaag 300
agcttcaaca ggaatgagtg t 321

<210> SEQ ID NO 37
<211> LENGTH: 457
<212> TYPE: PRT
<213> ORGANISM: Artificial Sequence
<220> FEATURE:
<223> OTHER INFORMATION: Heavy chain

<400> SEQUENCE: 37

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Val Ile Ser His Gly Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Ile Ser Asn Cys His Leu Gly Val Cys Tyr Tyr Ser Asn
100 105 110

Gly Met Asp Val Trp Gly Gln Gly Thr Leu Val Thr Val Ser Ser Ala
115 120 125

Lys Thr Thr Ala Pro Ser Val Tyr Pro Leu Ala Pro Val Cys Gly Asp
130 135 140

Thr Thr Gly Ser Ser Val Thr Leu Gly Cys Leu Val Lys Gly Tyr Phe
145 150 155 160

Pro Glu Pro Val Thr Leu Thr Trp Asn Ser Gly Ser Leu Ser Ser Gly
165 170 175

Val His Thr Phe Pro Ala Val Leu Gln Ser Asp Leu Tyr Thr Leu Ser
180 185 190

Ser Ser Val Thr Val Thr Ser Ser Thr Trp Pro Ser Gln Ser Ile Thr
195 200 205

Cys Asn Val Ala His Pro Ala Ser Ser Thr Lys Val Asp Lys Lys Ile
210 215 220

Glu Pro Arg Gly Pro Thr Ile Lys Pro Cys Pro Pro Cys Lys Cys Pro
225 230 235 240

Ala Pro Asn Leu Leu Gly Gly Pro Ser Val Phe Ile Phe Pro Pro Lys
245 250 255

Ile Lys Asp Val Leu Met Ile Ser Leu Ser Pro Ile Val Thr Cys Val

```
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Asn Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
            340                 345                 350

Val Arg Ala Pro Gln Val Tyr Val Leu Pro Pro Pro Glu Glu Glu Met
        355                 360                 365

Thr Lys Lys Gln Val Thr Leu Thr Cys Met Val Thr Asp Phe Met Pro
    370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
                405                 410                 415

Tyr Ser Lys Leu Arg Val Glu Lys Lys Asn Trp Val Glu Arg Asn Ser
            420                 425                 430

Tyr Ser Cys Ser Val Val His Glu Gly Leu His Asn His His Thr Thr
        435                 440                 445

Lys Ser Phe Ser Arg Thr Pro Gly Lys
    450                 455


<210> SEQ ID NO 38
<211> LENGTH: 457
<212> TYPE: PRT
<213> ORGANISM: Artificial Sequence
<220> FEATURE:
<223> OTHER INFORMATION: Heavy chain

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ile Ser Asn Cys His Leu Gly Val Cys Tyr Tyr Ser Asn
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

```
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455


<210> SEQ ID NO 39
<211> LENGTH: 218
<212> TYPE: PRT
<213> ORGANISM: Artificial Sequence
<220> FEATURE:
<223> OTHER INFORMATION: Light chain

<400> SEQUENCE: 39

Gln Leu Val Leu Thr Gln Pro Pro Ser Val Ser Ala Ala Pro Gly Gln
1               5                   10                  15

Arg Val Ser Ile Ser Cys Ser Gly Ser Ser Ser Asn Ile Gly Asp Asn
            20                  25                  30

Tyr Val Ser Trp Tyr Gln Gln Val Pro Gly Ser Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
```

```
65                  70                  75                  80

Thr Gly Asp Glu Ala Asp Tyr Tyr Cys Ala Thr Trp Asp Gly Ser Leu
                85                  90                  95

Ser Ala Gly Arg Val Phe Gly Gly Gly Thr Lys Leu Thr Val Leu Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 40
<211> LENGTH: 218
<212> TYPE: PRT
<213> ORGANISM: Artificial Sequence
<220> FEATURE:
<223> OTHER INFORMATION: Light chain

<400> SEQUENCE: 40

Gln Leu Val Leu Thr Gln Pro Pro Ser Val Ser Ala Ala Pro Gly Gln
1               5                   10                  15

Arg Val Ser Ile Ser Cys Ser Gly Ser Ser Ser Asn Ile Gly Asp Asn
            20                  25                  30

Tyr Val Ser Trp Tyr Gln Gln Val Pro Gly Ser Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Gly Ser Leu
                85                  90                  95

Ser Ala Gly Arg Val Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

210 215

<210> SEQ ID NO 41
<211> LENGTH: 1380
<212> TYPE: DNA
<213> ORGANISM: Artificial Sequence
<220> FEATURE:
<223> OTHER INFORMATION: Heavy chain

<400> SEQUENCE: 41
gaagttcagc tgcttgagtc tggcggagga ctggttcaac ctggcggaag cctgagactg 60
tcttgtgccg ccagcggctt caccttcagc aactacgcca tgagctgggt ccgacaggcc 120
cctggaaaag gccttgaatg ggtgtccgtg atctctcacg gcggaggcag cacctactac 180
gccgattctg tgaagggcag attcaccatc agccgggaca acagcaagaa caccctgtac 240
ctgcagatga acagcctgag agccgaggac accgccgtgt actattgcgc cagagtgatc 300
agcaactgcc acctgggcgt gtgctactac agcaacggca tggatgtgtg gggccagggc 360
acactggtta ccgttagttc tgctagcgcc aaaacaacag ccccctccgt atacccccta 420
gcccccgtat gcggcgacac caccggctcc tccgtaaccc taggctgcct agtaaaaggc 480
tacttccccg aacccgtaac cctaacctgg aactccggct ccctatcctc cggcgtacac 540
accttccccg ccgtactaca atccgaccta tacaccctat cctcctccgt aaccgtaacc 600
tcctccacct ggccctccca atccatcacc tgcaacgtag cccaccccgc ctcctccacc 660
aaagtagaca aaaaaatcga gccaaggggc cccaccatca agccttgccc tccctgcaag 720
tgccctgccc ccaacctgct gggcggcccc tccgtgttca tcttccctcc aaagatcaag 780
gacgtgctga tgatctccct gagccccatc gtgacctgcg tggtggtgga cgtgtccgag 840
gacgaccctg acgtgcagat cagctggttc gtgaacaacg tggaggtgca caccgcccag 900
acccagaccc acagagagga ctacaactcc accctgaggg tggtgagcgc cctgccaatc 960
cagcaccagg actggatgtc cggcaaggag ttcaagtgca aggtgaacaa caaggacctg 1020
ccagccccaa tcgagaggac catcagcaag cctaagggct ccgtgagggc cccccaggtg 1080
tacgtgctgc cccctcctga ggaggagatg accaagaagc aggtgaccct gacctgcatg 1140
gtgaccgact tcatgcctga ggacatctac gtggagtgga ccaacaacgg caagaccgag 1200
ctgaactaca agaacaccga gcctgtgctg gacagcgacg gcagctactt catgtacagc 1260
aagctgaggg tggagaagaa gaactgggtg gagagaaact cctactcctg ctccgtggtg 1320
cacgagggcc tgcacaacca ccacaccacc aagagcttct ccagaacccc cgggaagtga 1380

<210> SEQ ID NO 42
<211> LENGTH: 1371
<212> TYPE: DNA
<213> ORGANISM: Artificial Sequence
<220> FEATURE:
<223> OTHER INFORMATION: Heavy chain

<400> SEQUENCE: 42
gaagttcagc tgcttgagtc tggcggagga ctggttcaac ctggcggaag cctgagactg 60
tcttgtgccg ccagcggctt caccttcagc aactacgcca tgagctgggt ccgacaggcc 120
cctggaaaag gccttgaatg ggtgtccgtg atctctcacg gcggaggcag cacctactac 180
gccgattctg tgaagggcag attcaccatc agccgggaca acagcaagaa caccctgtac 240
ctgcagatga acagcctgag agccgaggac accgccgtgt actattgcgc cagagtgatc 300
agcaactgcc acctgggcgt gtgctactac agcaacggca tggatgtgtg gggccagggc 360

```
acactggtta ccgttagttc tgctagcacc aagggcccat cggtcttccc cctggcgccc    420

tcctccaaga gcacctctgg gggcacagcg gccctgggct gcctggtcaa ggactacttc    480

cccgaaccgg tgacggtgtc gtggaactca ggggccctga ccagcggcgt gcacaccttc    540

ccggctgtcc tacagtcctc aggactctac tccctcagca gcgtggtgac cgtgccctcc    600

agcagcctgg gcacccagac ctacatctgc aacgtgaatc acaagcccag caacaccaag    660

gtggacaaga aagttgagcc caaatcttgt gacaaaactc acacatgccc accgtgccca    720

gcacctgaac tcctgggggg accgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccagcc   1020

cccatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta cagcaagctc   1260

accgtggaca agagcaggtg gcagcagggg aacgtcttct catgctccgt gatgcatgag   1320

gctctgcaca accactacac gcagaagagc ctctccctgt ctccgggtaa a            1371
```

<210> SEQ ID NO 43
<211> LENGTH: 654
<212> TYPE: DNA
<213> ORGANISM: Artificial Sequence
<220> FEATURE:
<223> OTHER INFORMATION: Light chain

<400> SEQUENCE: 43

```
caactggttc tgacacagcc tccaagcgtg tcagctgccc ctggacagag agtgtccatc     60

agctgtagcg gcagcagcag caacatcggc gacaactacg tgtcctggta tcagcaggtc    120

ccaggctctg cccctaagct gctgatctac gacaacaaca agcggcccag cggcatcccc    180

gatagatttt ctgccagcaa gagcggcacc agcgccacac tgggaattac aggactgcag    240

acaggcgacg aggccgacta ctattgtgcc acatgggatg gctccctgag cgccggaaga    300

gtttttggcg gaggcaccaa gctgaccgtg cttcgtacgg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgt          654
```

<210> SEQ ID NO 44
<211> LENGTH: 654
<212> TYPE: DNA
<213> ORGANISM: Artificial Sequence
<220> FEATURE:
<223> OTHER INFORMATION: Light chain

<400> SEQUENCE: 44

```
caactggttc tgacacagcc tccaagcgtg tcagctgccc ctggacagag agtgtccatc     60
```

-continued

```
agctgtagcg gcagcagcag caacatcggc gacaactacg tgtcctggta tcagcaggtc    120

ccaggctctg cccctaagct gctgatctac gacaacaaca agcggcccag cggcatcccc    180

gatagatttt ctgccagcaa gagcggcacc agcgccacac tgggaattac aggactgcag    240

acaggcgacg aggccgacta ctattgtgcc acatgggatg gctccctgag cgccggaaga    300

gtttttggcg gaggcaccaa gctgaccgtg cttagatctg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

<210> SEQ ID NO 45
<211> LENGTH: 24
<212> TYPE: DNA
<213> ORGANISM: Artificial Sequence
<220> FEATURE:
<223> OTHER INFORMATION: mouse Lrig-1 forward primer

<400> SEQUENCE: 45

```
gacggaattc agtgaggaga acct                                             24
```

<210> SEQ ID NO 46
<211> LENGTH: 24
<212> TYPE: DNA
<213> ORGANISM: Artificial Sequence
<220> FEATURE:
<223> OTHER INFORMATION: mouse Lrig-1 reverse primer

<400> SEQUENCE: 46

```
caactggtag tggcagcttg tagg                                             24
```

<210> SEQ ID NO 47
<211> LENGTH: 24
<212> TYPE: DNA
<213> ORGANISM: Artificial Sequence
<220> FEATURE:
<223> OTHER INFORMATION: mouse Lrig-2 forward primer

<400> SEQUENCE: 47

```
tcacaaggaa cattgtctga acca                                             24
```

<210> SEQ ID NO 48
<211> LENGTH: 24
<212> TYPE: DNA
<213> ORGANISM: Artificial Sequence
<220> FEATURE:
<223> OTHER INFORMATION: mouse Lrig-2 reverse primer

<400> SEQUENCE: 48

```
gcctgatcta acacatcctc ctca                                             24
```

<210> SEQ ID NO 49
<211> LENGTH: 24
<212> TYPE: DNA
<213> ORGANISM: Artificial Sequence
<220> FEATURE:
<223> OTHER INFORMATION: mouse Lrig-3 forward primer

<400> SEQUENCE: 49

```
cagcaccttg agctgaacag aaac                                             24
```

<210> SEQ ID NO 50
<211> LENGTH: 24
<212> TYPE: DNA
<213> ORGANISM: Artificial Sequence
<220> FEATURE:
<223> OTHER INFORMATION: mouse Lrig-3 reverse primer

<400> SEQUENCE: 50
ccagcctttg gtaatctcgg ttag 24

<210> SEQ ID NO 51
<211> LENGTH: 24
<212> TYPE: DNA
<213> ORGANISM: Artificial Sequence
<220> FEATURE:
<223> OTHER INFORMATION: mouse FOXP3 forward primer

<400> SEQUENCE: 51
ctttcaccta tcccaccctt atcc 24

<210> SEQ ID NO 52
<211> LENGTH: 24
<212> TYPE: DNA
<213> ORGANISM: Artificial Sequence
<220> FEATURE:
<223> OTHER INFORMATION: mouse FOXP3 reverse primer

<400> SEQUENCE: 52
attcatctac ggtccacact gctc 24

<210> SEQ ID NO 53
<211> LENGTH: 20
<212> TYPE: DNA
<213> ORGANISM: Artificial Sequence
<220> FEATURE:
<223> OTHER INFORMATION: ACTG1 forward primer

<400> SEQUENCE: 53
ggcgtcatgg tgggcatggg 20

<210> SEQ ID NO 54
<211> LENGTH: 20
<212> TYPE: DNA
<213> ORGANISM: Artificial Sequence
<220> FEATURE:
<223> OTHER INFORMATION: ACTG1 reverse primer

<400> SEQUENCE: 54
atggcgtggg gaagggcgta 20

<210> SEQ ID NO 55
<211> LENGTH: 455
<212> TYPE: PRT
<213> ORGANISM: Artificial Sequence
<220> FEATURE:
<223> OTHER INFORMATION: synthetic

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45
```

```
Ser Val Ile Ser His Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ile Ser Asn Cys His Leu Gly Val Cys Tyr Tyr Ser Asn
            100                 105                 110

Gly Met Asp Val Trp Gly Gln Gly Thr Leu Val Thr Val Ser Ser Thr
        115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Thr Ser Ser Thr Trp Pro Ser Gln Ser Ile Thr Cys Asn
        195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Leu Leu Gly Gly Pro Ser Val Phe Ile Phe Pro Pro Lys Ile Lys
                245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ala Pro Ile Glu Arg Thr Ile Ser Lys Pro Lys Gly Ser Val Arg
            340                 345                 350

Ala Pro Gln Val Tyr Val Leu Pro Pro Pro Glu Glu Glu Met Thr Lys
        355                 360                 365

Lys Gln Val Thr Leu Thr Cys Met Val Thr Asp Phe Met Pro Glu Asp
    370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Lys Asn Trp Val Glu Arg Asn Ser Tyr Ser
            420                 425                 430

Cys Ser Val Val His Glu Gly Leu His Asn His His Thr Thr Lys Ser
        435                 440                 445

Phe Ser Arg Thr Pro Gly Lys
    450                 455
```

```
<210> SEQ ID NO 56
<211> LENGTH: 217
<212> TYPE: PRT
<213> ORGANISM: Artificial Sequence
<220> FEATURE:
<223> OTHER INFORMATION: synthetic

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Tyr Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Arg Thr
            100                 105                 110

Val Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215
```

The invention claimed is:

1. A binding molecule comprising:

a heavy chain variable region comprising a heavy chain CDR1 consisting of the amino acid sequence of SEQ ID NO: 5, a heavy chain CDR2 consisting of the amino acid sequence of SEQ ID NO: 6, and a heavy chain CDR3 consisting of the amino acid sequence of SEQ ID NO: 7; and a light chain variable region comprising a light chain CDR1 consisting of the amino acid sequence represented by of SEQ ID NO: 8, a light chain CDR2 consisting of the amino acid sequence of SEQ ID NO: 9, and a light chain CDR3 consisting of the amino acid sequence of SEQ ID NO: 10.

2. The binding molecule according to claim 1, wherein the binding molecule comprises a heavy chain variable region consisting of the amino acid sequence of SEQ ID NO: 11, and a light chain variable region consisting of the amino acid sequence of SEQ ID NO: 12.

3. The binding molecule according to claim 1, wherein the binding molecule further comprises a fragment crystallization region (Fc region) or a constant region.

4. The binding molecule according to claim 1, wherein the Fc region is the Fc region of an IgA, IgD, IgE, IgM, IgG1, IgG2, IgG3, or IgG4 antibody, or a hybrid Fc region.

5. The binding molecule according to claim 3, wherein the binding molecule further comprises a heavy chain constant region consisting of the amino acid sequence selected from the group consisting of SEQ ID NOs: 21, 23, 24, 27, 28, 29, 30 and 32.

6. The binding molecule according to claim 3, wherein the binding molecule further comprises a light chain constant region consisting of the amino acid sequence selected from the group consisting of SEQ ID NOs: 22, 25, 26, and 31.

7. The binding molecule according to claim 1, wherein the binding molecule comprises a heavy chain consisting of the amino acid sequence of SEQ ID NO: 37 or 38, and a light chain consisting of the amino acid sequence of SEQ ID NO: 39 or 40.

8. The binding molecule according to claim 1, wherein the binding molecule is an antibody or an antigen-binding fragment thereof.

9. The binding molecule according to claim 8, wherein the antibody is a chimeric antibody, a humanized antibody, a bivalent, a bispecific molecule, a minibody, a domain antibody, a bispecific antibody, an antibody mimetic, a diabody, a triabody, a tetrabody, or an antigen-binding fragment thereof.

10. A nucleic acid molecule encoding the binding molecule of claim 1.

11. An expression vector into which the nucleic acid molecule of claim 10 is inserted.

12. A host cell line transfected with the expression vector of claim 11.

13. An antibody-drug conjugate (ADC) comprising an antibody and a drug, wherein the antibody comprises:

a heavy chain variable region comprising a heavy chain CDR1 consisting of the amino acid sequence of SEQ ID NO: 5, a heavy chain CDR2 consisting of the amino acid sequence of SEQ ID NO: 6, and a heavy chain CDR3 consisting of the amino acid sequence of SEQ ID NO: 7; and a light chain variable region comprising a light chain CDR1 consisting of the amino acid sequence of SEQ ID NO: 8, a light chain CDR2 consisting of the amino acid sequence of SEQ ID NO: 9, and a light chain CDR3 consisting of the amino acid sequence of SEQ ID NO: 10.

14. A chimeric antigen receptor (CAR) comprising an antigen-specific binding domain, a linking domain, and a CD3 zeta (ζ) signaling domain, wherein the antigen-specific binding domain comprises:

a heavy chain variable region comprising a heavy chain CDR1 consisting of the amino acid sequence of SEQ ID NO: 5, a heavy chain CDR2 consisting of the amino acid sequence of SEQ ID NO: 6, and a heavy chain CDR3 consisting of the amino acid sequence of SEQ ID NO: 7; and a light chain variable region comprising a light chain CDR1 consisting of the amino acid sequence of SEQ ID NO: 8, a light chain CDR2 consisting of the amino acid sequence of SEQ ID NO: 9, and a light chain CDR3 consisting of the amino acid sequence of SEQ ID NO: 10.

15. A method for treating a neurodegenerative or neuroinflammatory disease by administering the binding molecule of claim 1 as an active ingredient into a subject.

16. A method for treating a neurodegenerative or neuroinflammatory disease by administering the antibody-drug conjugate (ADC) of claim 13 as an active ingredient into a subject.

17. A method for treating a neurodegenerative or neuroinflammatory disease by administering the chimeric antigen receptor (CAR) of claim 14 as an active ingredient into a subject.

18. A method for treating Alzheimer's Disease by administering the binding molecule of claim 1 as an active ingredient into a subject.

19. A method for treating Alzheimer's Disease by administering the antibody-drug conjugate (ADC) of claim 13 as an active ingredient into a subject.

20. A method for treating Alzheimer's Disease by administering the chimeric antigen receptor (CAR) of claim 14 as an active ingredient into a subject.

* * * * *